United States Patent
Liu et al.

(10) Patent No.: US 11,357,427 B2
(45) Date of Patent: **\*Jun. 14, 2022**

(54) SYSTEMS AND METHODS FOR ANALYZING, INTERPRETING, AND ACTING ON CONTINUOUS GLUCOSE MONITORING DATA

(71) Applicant: Welldoc, Inc., Columbia, MD (US)

(72) Inventors: Shiping Liu, Columbia, MD (US); Mansur Shomali, Columbia, MD (US); Abhimanyu Kumbara, Columbia, MD (US); Anand Iyer, Columbia, MD (US); Malinda Peeples, Columbia, MD (US); Michelle Dugas, Columbia, MD (US); Kenyon Crowley, Columbia, MD (US); Guodong Gao, Columbia, MD (US)

(73) Assignee: Welldoc, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/474,807

(22) Filed: Sep. 14, 2021

(65) Prior Publication Data

US 2021/0401333 A1    Dec. 30, 2021

Related U.S. Application Data

(63) Continuation of application No. 17/206,858, filed on Mar. 19, 2021, now Pat. No. 11,147,480.
(Continued)

(51) Int. Cl.
*A61B 5/145* (2006.01)
*G16H 50/30* (2018.01)
(Continued)

(52) U.S. Cl.
CPC ........ *A61B 5/14532* (2013.01); *A61B 5/1118* (2013.01); *A61B 5/48* (2013.01);
(Continued)

(58) Field of Classification Search
None
See application file for complete search history.

(56) References Cited

U.S. PATENT DOCUMENTS 6,256,613 B1    7/2001    Falchuk et al.
7,935,307 B2    5/2011    Angelides
(Continued)

FOREIGN PATENT DOCUMENTS

CA    3105740 A1    1/2020
CA    3111924 A1    3/2020
(Continued)

*Primary Examiner* — Michael R Bloch
(74) *Attorney, Agent, or Firm* — Bookoff McAndrews, PLLC

(57) ABSTRACT

Methods and devices include automated coaching for management of glucose states by receiving a user's glucose levels using a continuous glucose monitoring (CGM) device, determining a time in range (TIR) value, determining a TIR state, receiving a glucose variability (GV) value, determining a GV state, determining a starting state based on the TIR state and the GV state, determining that the starting state corresponds to a non-ideal state, generating an optimized pathway to reach an ideal state based on one or more account vectors such as addressing self-management behavior including food, activity, and medication use. The optimized pathway may further be based on computer detection and classification of significant events of interest over time.

20 Claims, 29 Drawing Sheets

Related U.S. Application Data

(60) Provisional application No. 63/135,818, filed on Jan. 11, 2021, provisional application No. 62/992,385, filed on Mar. 20, 2020, provisional application No. 62/992,409, filed on Mar. 20, 2020.

(51) Int. Cl.
*G16H 20/00* (2018.01)
*G06N 20/00* (2019.01)
*A61B 5/00* (2006.01)
*G16H 10/40* (2018.01)
*A61B 5/11* (2006.01)

(52) U.S. Cl.
CPC .......... *A61B 5/7264* (2013.01); *A61B 5/7267* (2013.01); *A61B 5/7275* (2013.01); *A61B 5/7282* (2013.01); *A61B 5/7475* (2013.01); *G06N 20/00* (2019.01); *G16H 10/40* (2018.01); *G16H 20/00* (2018.01); *G16H 50/30* (2018.01); *A61B 5/0022* (2013.01)

(56) References Cited

U.S. PATENT DOCUMENTS

| | | |
|---|---|---|
| 8,568,309 B2 | 10/2013 | Angelides |
| 8,812,244 B2 | 8/2014 | Angelides |
| 10,595,754 B2 | 3/2020 | Pushpala et al. |
| 2007/0173761 A1 | 7/2007 | Kanderian, Jr. et al. |
| 2008/0071580 A1* | 3/2008 | Marcus ............... G16H 15/00 705/3 |
| 2008/0125636 A1* | 5/2008 | Ward ................ A61B 5/4833 600/365 |
| 2008/0269714 A1 | 10/2008 | Mastrototaro et al. |
| 2008/0306770 A1* | 12/2008 | Sysko ................ G16H 20/17 705/3 |
| 2009/0105568 A1* | 4/2009 | Bugler ................ A61B 5/742 600/347 |
| 2010/0106000 A1* | 4/2010 | Thomas ............... A61B 5/743 600/365 |
| 2011/0093249 A1* | 4/2011 | Holmes ............... G16H 50/50 703/6 |
| 2012/0232520 A1* | 9/2012 | Sloan ................. G16Z 99/00 604/504 |
| 2012/0246106 A1* | 9/2012 | Atlas ................. G16H 20/17 706/52 |
| 2013/0117040 A1 | 5/2013 | James et al. |
| 2014/0073892 A1* | 3/2014 | Randloev ........... A61B 5/7275 600/365 |
| 2014/0222454 A1 | 8/2014 | Duffy et al. |
| 2015/0079561 A1 | 3/2015 | Petakov et al. |
| 2016/0029931 A1 | 2/2016 | Salas-Boni et al. |
| 2016/0029966 A1 | 2/2016 | Salas-Boni et al. |
| 2017/0076630 A1 | 3/2017 | Angelides et al. |
| 2017/0220751 A1* | 8/2017 | Davis ................. G06N 5/048 |
| 2017/0329917 A1* | 11/2017 | McRaith .............. G16H 10/20 |
| 2018/0042559 A1* | 2/2018 | Cabrera, Jr. ......... G16H 70/40 |
| 2019/0008461 A1* | 1/2019 | Gupta ................ G16H 10/40 |
| 2019/0142314 A1* | 5/2019 | Masciotti ............ A61B 5/7435 600/365 |
| 2019/0192768 A1* | 6/2019 | Gupta ............... A61M 5/14276 |
| 2019/0320976 A1* | 10/2019 | Roslin ................ G16H 50/20 |
| 2020/0375549 A1* | 12/2020 | Wexler ............... G16H 50/70 |
| 2020/0383648 A1 | 12/2020 | Bridgewater et al. |
| 2020/0388393 A1 | 12/2020 | Boulos et al. |
| 2020/0388403 A1 | 12/2020 | Boulos et al. |
| 2021/0128833 A1 | 5/2021 | Debong et al. |

FOREIGN PATENT DOCUMENTS

| | | |
|---|---|---|
| CN | 112655045 A | 4/2021 |
| EP | 3651164 A1 | 5/2020 |
| JP | 2018032438 A | 3/2018 |
| JP | 2020091885 A | 6/2020 |
| WO | 2013184896 A1 | 12/2013 |
| WO | 2014145335 A1 | 9/2014 |
| WO | 2015153127 A1 | 10/2015 |
| WO | 2020094765 A1 | 5/2020 |
| WO | 2020243576 A1 | 12/2020 |
| WO | 2020247032 A1 | 12/2020 |

* cited by examiner

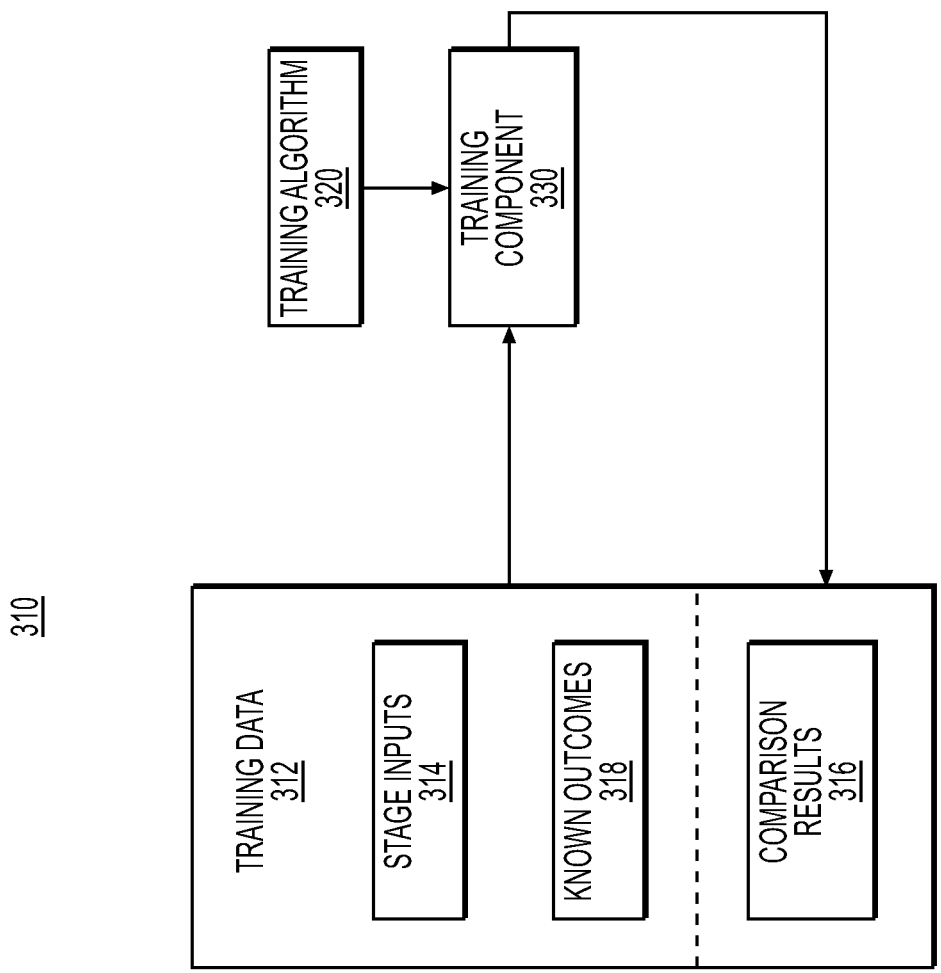

406   NAME _____
      MRN _____

| GLUCOSE STATISTICS AND TARGETS | |
|---|---|
| 26 FEB 2019-10 MAR 2019 | 13 DAYS |
| % TIME CGM IS ACTIVE | 99.9% |

| GLUCOSE RANGES | TARGETS [% OF READINGS (TIME/DAY)] |
|---|---|
| TARGET RANGE 70-180 mg/dL | GREATER THAN 70% (16h 48min) |
| BELOW 70 mg/dL | LESS THAN 4% (58min) |
| BELOW 54 mg/dL | LESS THAN 1% (14min) |
| ABOVE 250 mg/dL | LESS THAN 5% (1h 12min) |
| EACH 5% INCREASE IN TIME IN RANGE (70/180 mg/dL) IS CLINICALLY BENEFICIAL | |

| | |
|---|---|
| AVERAGE GLUCOSE | 173 mg/dL |
| GLUCOSE MANAGEMENT INDICATOR (GMI) | 7.6% |
| GLUCOSE VARIABILITY | 49.5% |
| DEFINED AS PERCENT COEFFICIENT OF VARIATION (%CV): TARGET ≤30% | |

408

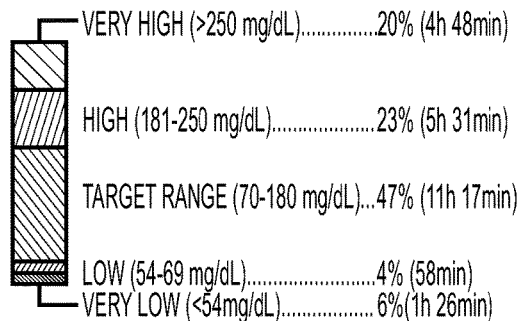

TIME IN RANGES
- VERY HIGH (>250 mg/dL) .............. 20% (4h 48min)
- HIGH (181-250 mg/dL) .................. 23% (5h 31min)
- TARGET RANGE (70-180 mg/dL) ... 47% (11h 17min)
- LOW (54-69 mg/dL) ......................... 4% (58min)
- VERY LOW (<54mg/dL) .................. 6% (1h 26min)

414

AMBULATORY GLUCOSE PROFILE (AGP)

AGP IS A SUMMARY OF GLUCOSE VALUES FROM THE REPORT PERIOD, WITH MEDIAN (50%) AND OTHER PERCENTILES SHOWN AS IF OCCURRING IN A SINGLE DAY

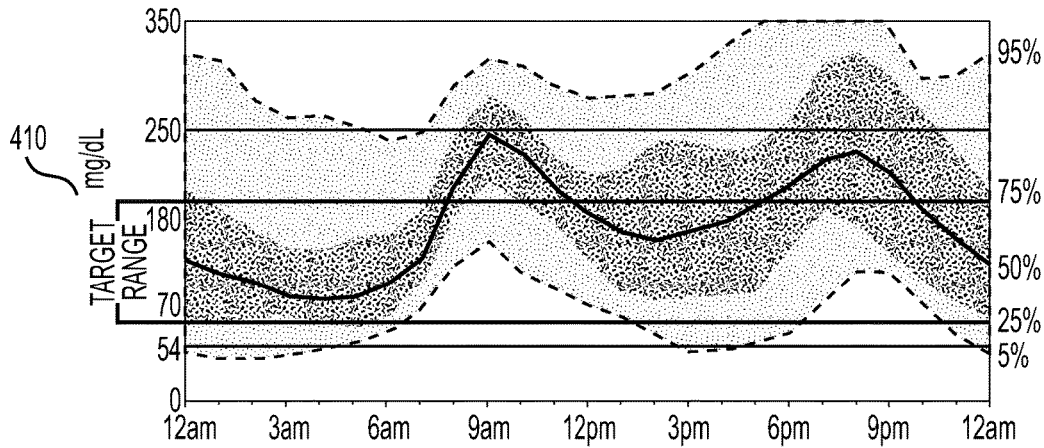

410

DAILY GLUCOSE PROFILES

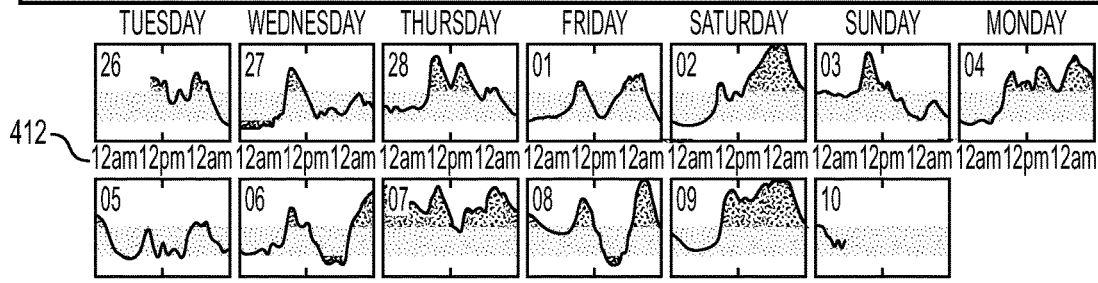

412

EACH DAILY PROFILE REPRESENTS A MIDNIGHT TO MIDNIGHT PERIOD.
PATENTS PENDING-HEALTHPARTNERS INSTITUTE DBA INTERNATIONAL DIABETES CENTER-ALL RIGHTS RESERVED. 2019

CAPTŪRAGPV4.0

FIG. 4B

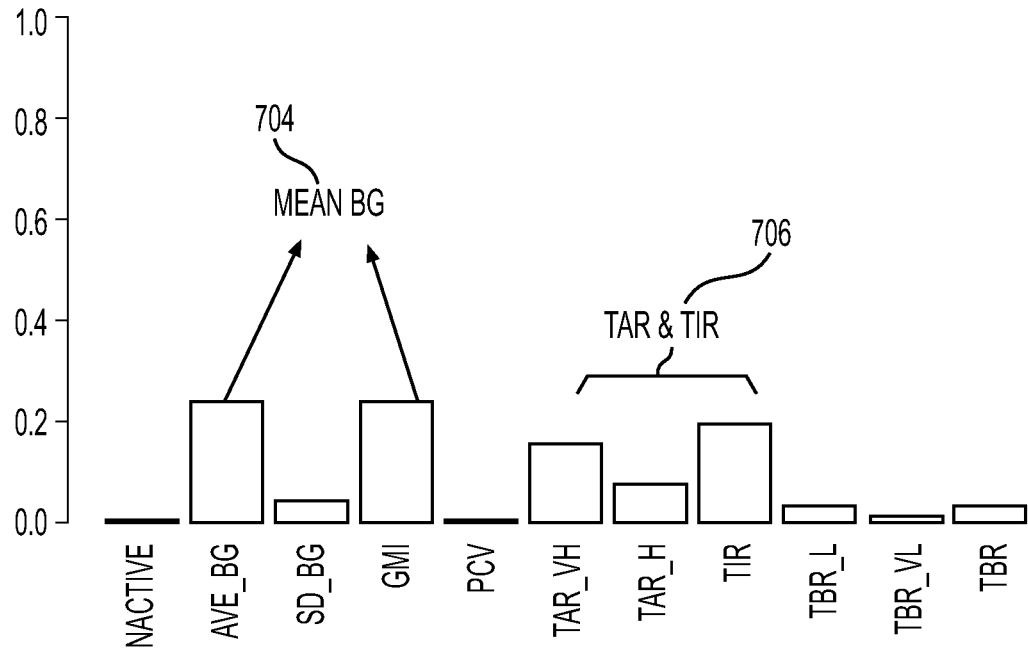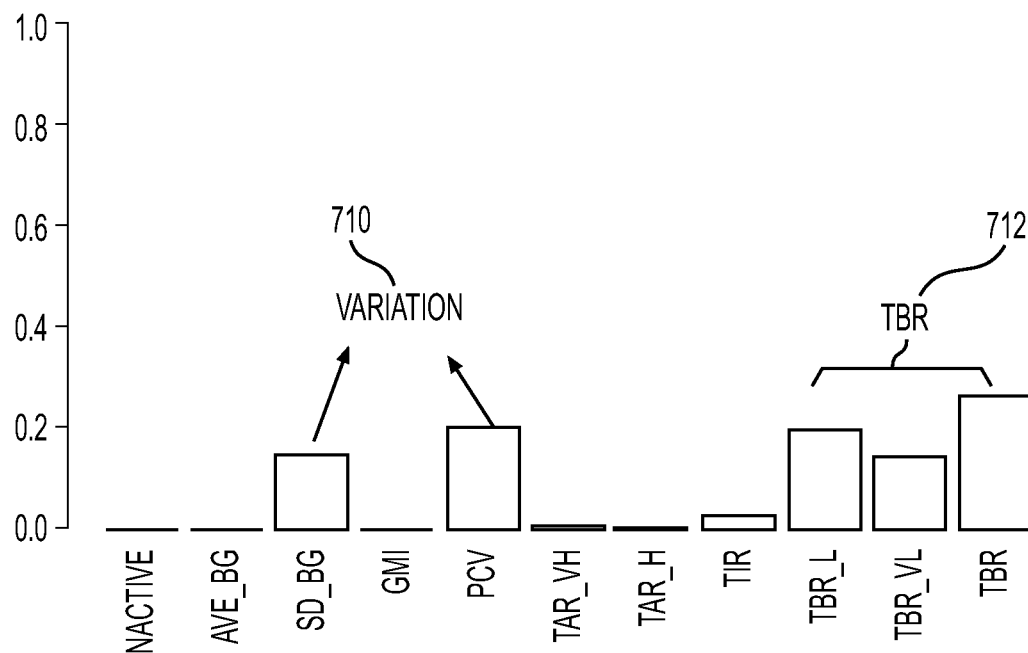
FIG. 7A

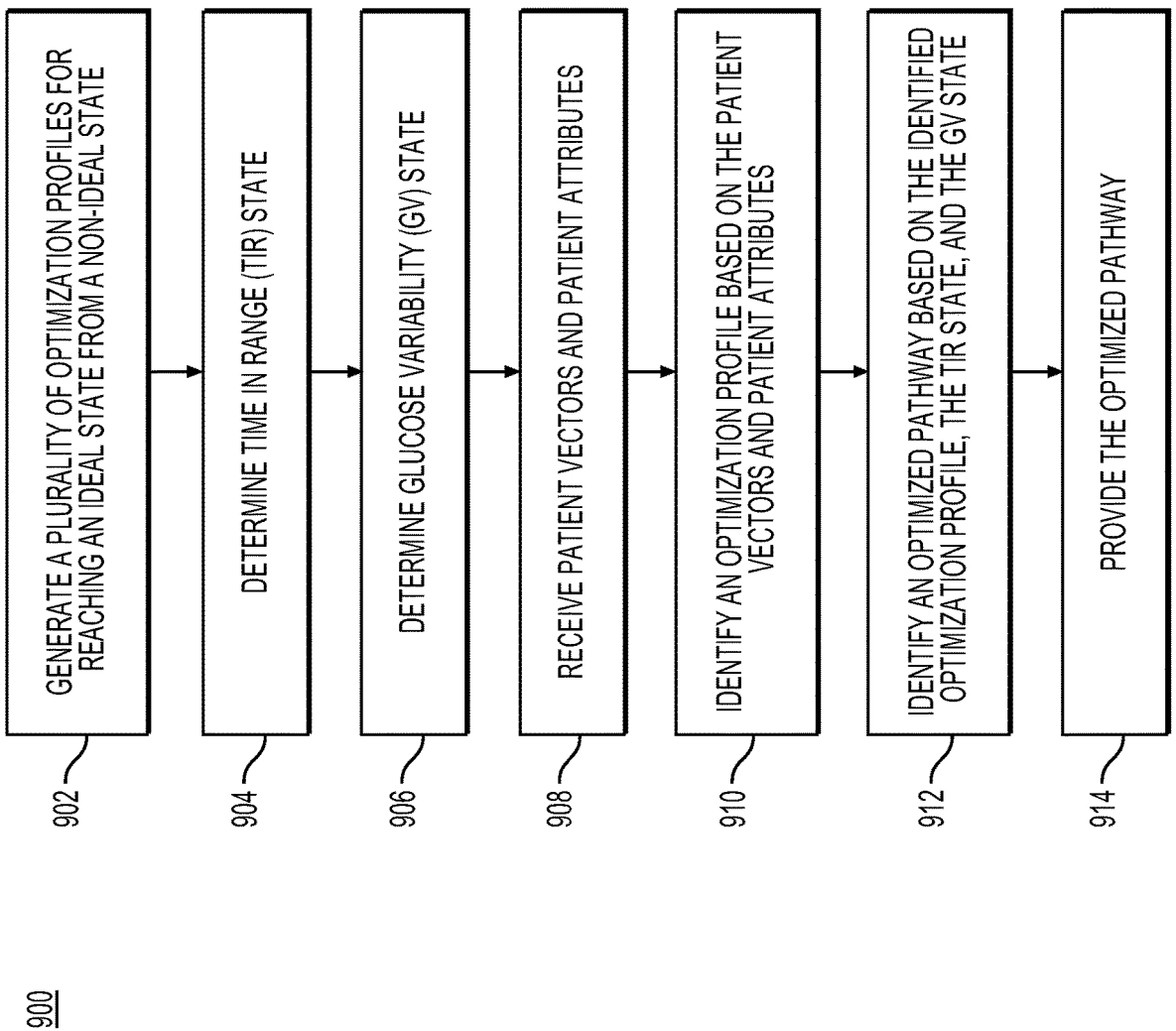

SYSTEMS AND METHODS FOR ANALYZING, INTERPRETING, AND ACTING ON CONTINUOUS GLUCOSE MONITORING DATA

RELATED APPLICATIONS

This application is a continuation of U.S. application Ser. No. 17/206,858, filed Mar. 19, 2021, which claims the benefit of priority to 1) U.S. Provisional Application No. 63/135,818, filed on Jan. 11, 2021, 2) U.S. Provisional Application No. 62/992,385, filed on Mar. 20, 2020, and 3) U.S. Provisional Application No. 62/992,409, filed on Mar. 20, 2020, each of which are incorporated herein by reference in its entirety.

TECHNICAL FIELD

The present disclosure relates generally to obtaining and processing data to generate optimized pathways to improve the health of a user, and, in some embodiments, specifically toward optimizing glucose states of a user via a mobile application.

INTRODUCTION

Increased healthcare costs have limited user access to appropriate care. At the same time, healthcare companies have increased provider workloads and limited physician-user interactions. Diabetes treatment often relies on sporadic readings (e.g., glucose readings) that do not provide ample data to effectively provide treatment options. Such readings are often used in isolation such that changes are recommended based on just a few readings. Any medical, dietary, and/or lifestyle changes recommended as a result of a given reading are therefore limited given the sparse data received via the sporadic readings.

The present disclosure is directed to addressing one or more of the above-referenced challenges. The introduction provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

This disclosure is directed to a computer-implemented method for managing glucose states of a user and includes receiving the user's glucose levels using a continuous glucose monitoring (CGM) device, determining a time in range (TIR) value of the user's glucose level, wherein the TIR value is based on an amount of time the user's glucose level is within a threshold band over a base time period, determining a TIR state based on the TIR value, receiving a glucose variability (GV) value based at least on the user's glucose level, wherein the GV value is one of a standard deviation (SD) or a coefficient of variance (CV), wherein a CV indicates a variability of the user's glucose level in view of a standard deviation of the glucose level over the base time period, determining a GV state based on the GV value, determining a starting state based on the TIR state and the GV state, determining that the starting state corresponds to a non-ideal state, generating an optimized pathway to reach an ideal state based on one or more account vectors, the optimized pathway comprising one or more adjustments to the one or more account vectors, and providing the optimized pathway to the user.

The threshold band may be between approximately 70 mg/dL and 180 mg/dL, the base time period may be 24 hours. The CV value may determined by dividing the standard deviation of the glucose level by a mean of the glucose level over the base time period. The TIR state may be a binary state selected form one of a good TIR state or a bad TIR state. The good TIR state may correspond to a TIR value of greater than a TIR threshold. The GV state may be a binary state selected form one of a good GV state or a bad GV state. The good GV state may correspond to a GV value of greater than a GV threshold. The account vectors may comprise one or more of glucose levels, medications, food consumption, exercise value, psycho-social parameters, or social-determinant parameters. The account vector may comprise glucose levels based on one or more CGM events classified based on a severity score. The optimized pathway is further based on a user attribute, the user attribute selected from one or more of a social attribute, medical attribute, user preference, metabolic attribute, or user demographic. The optimized pathway may comprise an increase in one or more state improving habits and/or a decrease in one or more state worsening habits.

This disclosure is directed to a computer-implemented method for managing glucose states of a user and includes generating a plurality of optimization profiles for reaching an ideal state from a non-ideal state, the ideal state corresponding to a good time in range (TIR) state and good a glucose variability (GV) state and the non-ideal state comprising at least one of a bad TIR state or a bad GV state, determining a current TIR state based on a TIR value of the user's glucose level, wherein the TIR value is based on an amount of time the user's glucose level is within a threshold band over a base time period and the current TIR state is one of a good TIR state or a bad TIR state, determining a current GV state being based on a GV value associated with the user's glucose level, wherein the GV value indicates a standard deviation (SD) of glucose levels or a coefficient of variance (CV), wherein the CV is variability of the user's glucose level in view of a standard deviation of the glucose level over the base time period, receiving one or more account vectors for the user, identifying one of the optimization profiles based on the one or more account vectors, the TIR state, and the CV state, identifying an optimized pathway based on the identified optimization profile, the optimized pathway comprising one or more adjustments to the one or more account vectors, and providing the optimized pathway to the user.

The plurality of optimization profiles may be generated by a machine learning model configured to receive account vectors as inputs and output one or more adjustments to the received account vectors. The plurality of optimization profiles may be further generated by associating the one or more adjustments to the received account vectors with one or more TIR states or GV states. Each of the plurality of optimization profiles may correspond to a potential TIR state, a potential GV state, and the one or more potential account vectors. One or more user attribute may be received and one of the optimization profiles may be identified further based on the one or more user attributes. The CV value may be determined by dividing the standard deviation of the glucose level by the mean of the glucose level over the base time period.

This disclosure is also directed to a system for managing glucose levels of a user, the system including a memory having processor-readable instructions stored therein, a processor configured to access the memory and execute the processor-readable instructions, which, when executed by the processor configures the processor to perform a method. The method includes electronically receiving the user's glucose levels using a continuous glucose monitoring (CGM) device configured to obtain glucose values using a component that penetrates a skin of the user, determining a time in range (TIR) value of the user's glucose level, wherein the TIR value is based on an amount of time the user's glucose level is within a threshold band over a base time period wherein the threshold band is between approximately 70 mg/dL and 180 mg/dL and the base time period is 24 hours, determining a TIR state based on the TIR value, wherein the TIR state is selected form a good TIR state or a bad TIR state, receiving a glucose variability (GV) value based at least on the user's glucose level, wherein the GV value is one of a standard deviation or a coefficient of variance (CV), wherein a CV indicates a variability of the user's glucose level in view of a standard deviation of the glucose level over the base time period, determining a GV state based on the GV value, wherein the GV state is one of a good GV state or a bad GV state, determining a starting state based on the TIR state and the GV state, determining that the starting state corresponds to a non-ideal state, detecting a CGM event based on the user's glucose levels, characterizing the CGM event based on one or more of a multi-parameter CGM classification or a severity and CGM event trace shape characterization, wherein the multi-parameter CGM classification comprises a glucose level at the beginning of the CGM event, a severity, and a glucose at the end of the CGM event, generating an optimized pathway to reach an ideal state based on one or more account vectors and the characterizing the CGM event, the optimized pathway comprising one or more adjustments to the one or more account vectors, and providing the optimized pathway to the user. Providing the optimized pathway to the user may include providing context based instructions to the user based on the optimized pathway.

BRIEF DESCRIPTION OF THE DRAWINGS

The accompanying drawings, which are incorporated in and constitute a part of this specification, illustrate examples of the disclosure and together with the description, serve to explain the principles of the disclosure.

FIG. 3B is a schematic illustration of training an exemplary machine learning model, according to an example of the present disclosure.

FIG. 4B is a continuous glucose monitoring (CGM) report, according to an example of the present disclosure.

FIG. 7A shows a mean glucose and range chart and a variation of glucose and range chart, according to another example of the present disclosure.

FIG. 9 is another flowchart of a health management method, according to an example of the present disclosure.

An Appendix is provided herewith and includes a description with examples of the present disclosure including experimental results.

DETAILED DESCRIPTION

Reference will now be made in detail to examples of the disclosure, which are illustrated in the accompanying drawings. Wherever possible, the same reference numbers will be used throughout the drawings to refer to the same or like parts.

In the discussion that follows, relative terms such as "about," "substantially," "approximately," etc. are used to indicate a possible variation of ±10% in a stated numeric value. It should be noted that the description set forth herein is merely illustrative in nature and is not intended to limit the examples of the subject matter, or the application and uses of such examples. Any implementation described herein as exemplary is not to be construed as preferred or advantageous over other implementations. Rather, as alluded to above, the term "exemplary" is used in the sense of example or "illustrative," rather than "ideal." The terms "comprise," "include," "have," "with," and any variations thereof are used synonymously to denote or describe a non-exclusive inclusion. As such, a process, method, article, or apparatus that uses such terms does not include only those steps, structure or elements but may include other steps, structures or elements not expressly listed or inherent to such process, method, article, or apparatus. Further, the terms "first," "second," and the like, herein do not denote any order, quantity, or importance, but rather are used to distinguish one element from another. Moreover, the terms "a" and "an" herein do not denote a limitation of quantity, but rather denote the presence of at least one of the referenced item.

Healthcare and Computing Environment

Figure 1:
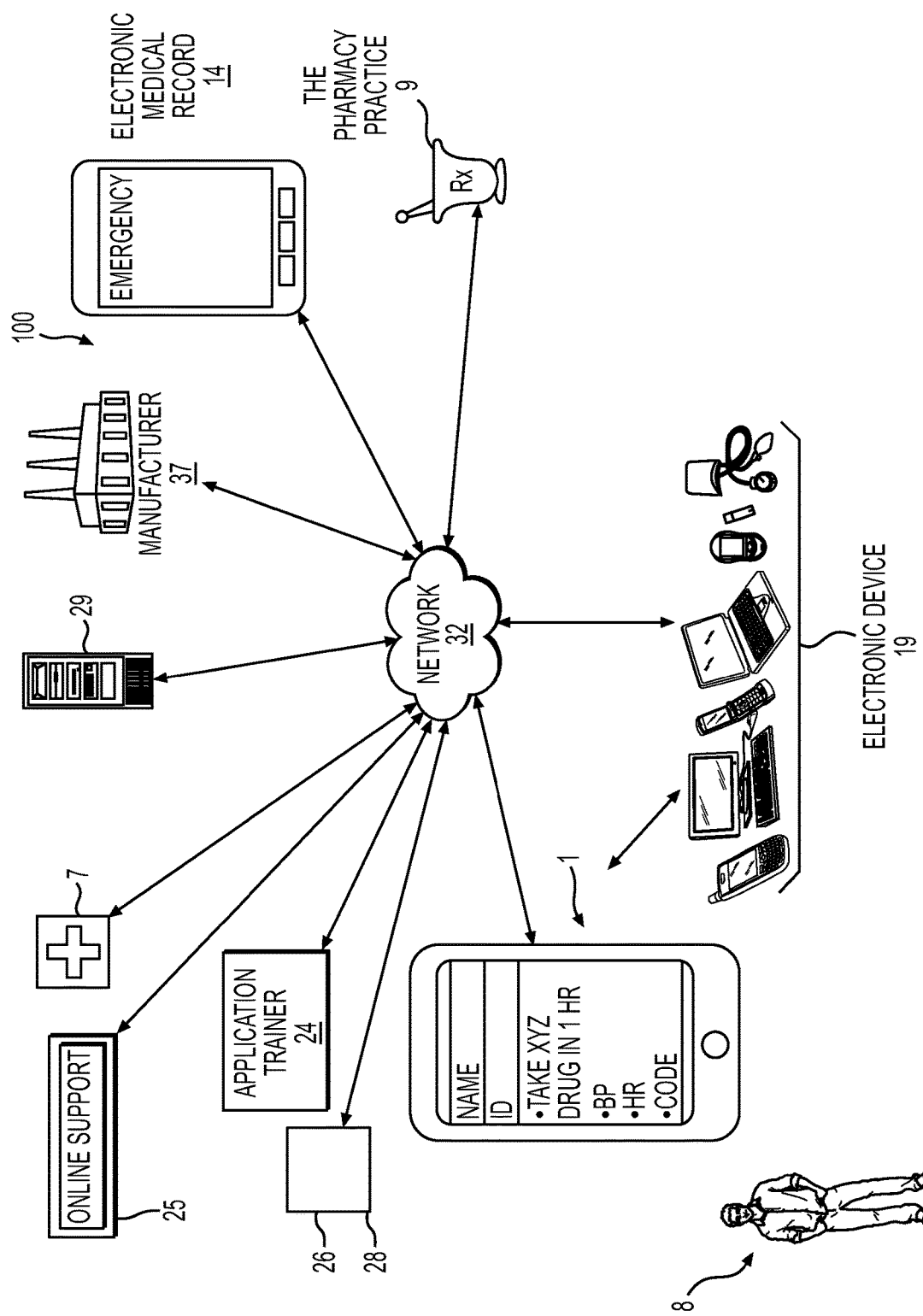
FIG. 1 is a schematic illustration of a health management system, according to an example of the present disclosure.

FIG. 1 is a block diagram of a health management system 100, according to an example of the present disclosure. A user (e.g., a patient, consumer, or the like) 8 having an electronic device 19, such as a mobile device, computer, medical device, or any other electronic device configured to access an electronic network 32, such as the Internet, may communicate with or otherwise access a mobile health (mHealth) application 1. In some examples, network 32 may include wireless or wired links, such as mobile telephone networks, Wi-Fi, LANs, WANs, Bluetooth, near-field communication (NFC), or other suitable forms of network communication. Multiple electronic devices 19 may be configured to access electronic network 32. A user 8 may access mHealth application 1 with a single account linked to multiple electronic devices 19 (e.g., via one or more of a mobile phone, a tablet, and a laptop computer). Electronic device 19 also may include, but is not limited to, mobile health devices, a desktop computer or workstation, a laptop computer, a mobile handset, a personal digital assistant (PDA), a cellular telephone, a network appliance, a camera, a smart phone, a smart watch, an enhanced general packet radio service (EGPRS) mobile phone, a media player, a navigation device, a game console, a set-top box, a biometric sensing device with communication capabilities, a smart TV, or any combination of these or other types of computing devices having at least one processor, a local memory, a display (e.g., a monitor or touchscreen display), one or more user input devices, and a network communication interface. The electronic device 19 may include any type or combination of input/output devices, such as a display monitor, keyboard, touchpad, accelerometer, gyroscope, mouse, touchscreen, camera, a projector, a touch panel, a pointing device, a scrolling device, a button, a switch, a motion sensor, an audio sensor, a pressure sensor, a thermal sensor, and/or microphone. Electronic devices 19 also may communicate with each other by any suitable wired or wireless means (e.g., via Wi-Fi, radio frequency (RF), infrared (IR), Bluetooth, Near Field Communication, or any other suitable means) to send and receive information.

mHealth application 1 may be in communication with other entities or networks to send and receive information. In some examples, mHealth application 1 may communicate with one or more applications associated with the user 8 such as, e.g., exercise tracking (e.g., step tracking) applications and/or other health-related applications. mHealth application 1 may be able to import data from the other applications to analyze and use in generating treatment plans for the user 8. For example, mHealth application 1 may import activity tracking data from another application and use that data to identify patterns between user 8 exercise and glucose values collected prior to the use of mHealth application 1. mHealth application 1 also may import any other suitable data from other mobile health applications such as, e.g., blood pressure, BMI, A1C, exercise type, exercise duration, exercise distance, calories burned, total steps, exercise date, exercise start and stop times, and sleep. mHealth application 1 also may export data to other mobile applications, including, e.g., other mobile health applications having social or interactive features. A healthcare provider 7, such as a physician, may prescribe the application. However, it is also contemplated that mHealth application 1 may not require a prescription, e.g., that it may be a commercially available consumer application accessible without a prescription from a digital distribution platform for computer software. mHealth application 1 may be tailored to a specific user 8 and may be activated in person by the user 8 by visiting a pharmacy 9 or other authorized entity. For example, the user 8 may receive an access code from the pharmacy that authorizes access to mHealth application 1. The user 8 may receive training on using mHealth application 1 by a mHealth support system 25 and/or application trainer 24. mHealth application 1 may include programming 28 of various forms, such as machine learning programming algorithms 26. The user treatment plan may include a prescription (e.g., for a drug, device, and/or therapy), which may be dispensed by the pharmacy 9. The pharmacy 9 may allow the refill of the prescribed product/therapy after receiving authorization based on the user's compliance with his/her healthcare treatment plan. The authorization may be received by the pharmacy 9 by a communication from the application 1, via, e.g., the network 32 and various servers 29. Use of the drug or other medical product/therapy also may be sent to the manufacturer 37 over the network 32 to inform the manufacturer 37 of the amount of medical product or therapy being used by user 8. This information may assist the manufacturer 37 in assessing demand and planning supply of the medical product or therapy. The healthcare provider 7 also may receive a report based on the user information received by the application 1, and may update the user treatment plan based on this information. The user's electronic medical record (EMR) 14 also may be automatically updated via the network 32 based on the user information, which may include electronically transmitted user 8 feedback on the application, received by mHealth application 1. Healthcare provider 7 may be any suitable healthcare provider including, e.g., a doctor, specialist, nurse, educator, social worker, MA, PA, or the like.

Figure 2:
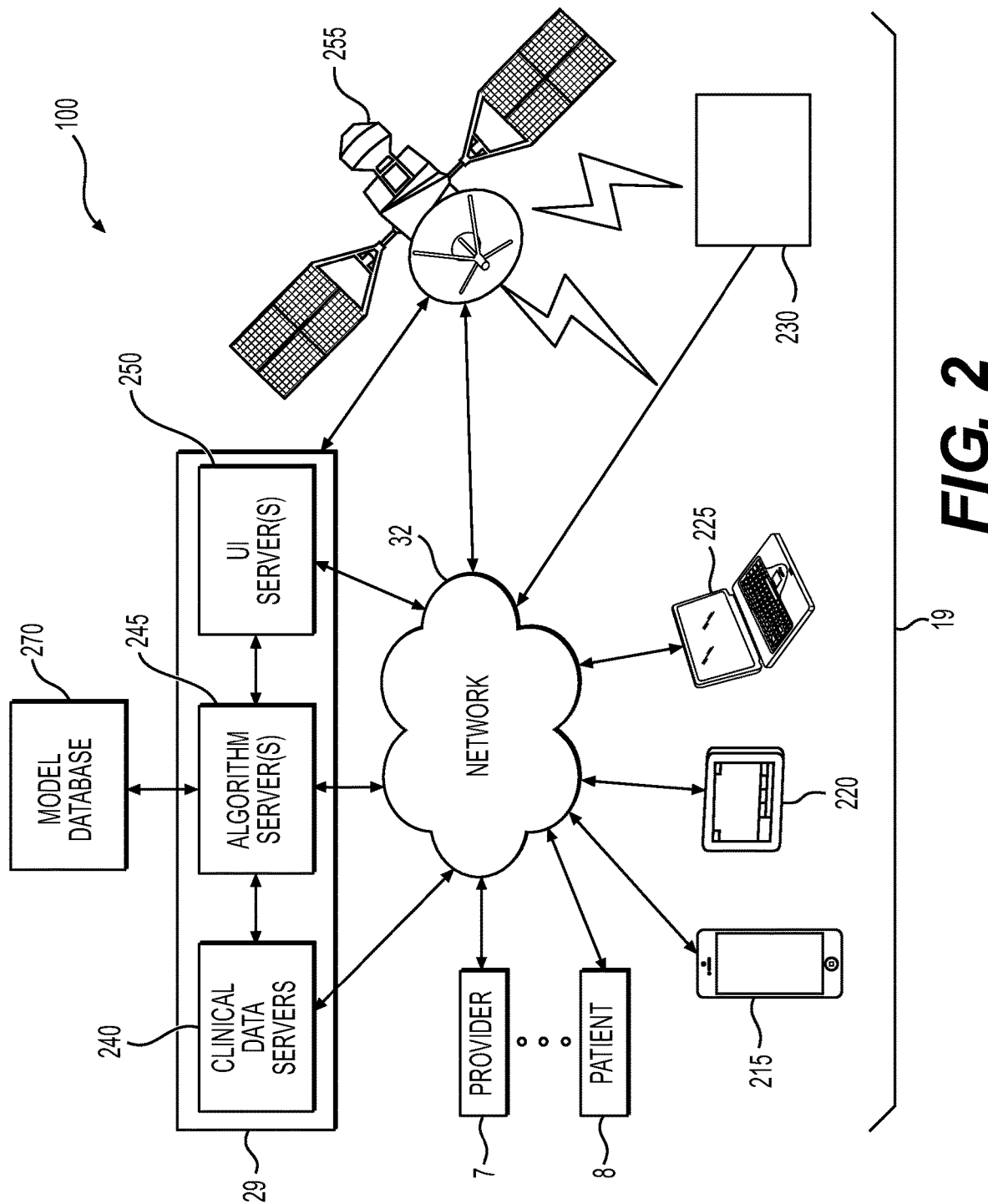
FIG. 2 is a schematic illustration of a portion of the health management system of FIG. 1.

FIG. 2 is a schematic diagram of additional aspects of system 100. For example, the system 100 may access decision models stored on a decision model database 270 via network 32. The retrieved decision models may be used for display and/or processing by one or more electronic devices 19, such as a mobile device 215, a tablet device 220, a computer (e.g., a laptop or desktop) 225, a kiosk 230 (e.g., at a kiosk, pharmacy, clinic, or hospital having medical and/or prescription information), and/or any device connected to network 32.

In the example shown in FIG. 2, mobile device 215, tablet 220, and computer 225 each may be equipped with or include, for example, a GPS receiver for obtaining and reporting location information, e.g., GPS data, via network 32 to and from any of servers 29 and/or one or more GPS satellites 255.

Each of electronic devices 19, including mobile device 215, tablet device 220, computer 225, and/or kiosk 230, may be configured to send and receive data (e.g., clinical information) to and from a system of servers 29 over network 32. Each of devices 19 may receive information, such as clinical data via the network 32 from servers 29. Servers 29 may include clinical data servers 240, algorithm servers 245, user interface (UI) servers 250, and/or any other suitable servers. Electronic device 19 may include a user interface that is in data communication with UI server 250 via network 32. Each server may access the decision model database 270 to retrieve decision models. Each server may include memory, a processor, and/or a database. For example, the clinical data server 240 may have a processor configured to retrieve clinical data from a provider's database and/or a patient's electronic medical record. The algorithm server 245 may have a database that includes various algorithms, and a processor configured to process the clinical data. The UI server 250 may be configured to receive and process user 8 input, such as clinical decision preferences. The satellite 255 may be configured to send and receive information between servers 29 and devices 19.

The clinical data server 240 may receive clinical data, such as data regarding the user from the electronic device 19 via the network 32 or indirectly via the UI server 250. The clinical data server 240 may save the information in memory, such as a computer readable memory.

The clinical data server 240 also may be in communication with one or more other servers, such as the algorithm server 245 and/or external servers. The servers 29 may include data about provider preferences, and/or user 8 health history. In addition, the clinical data server 240 may include data from other users. The algorithm server 245 may include machine learning, and/or other suitable algorithms. The algorithm server 245 also may be in communication with other external servers and may be updated as desired. For example, the algorithm server 245 may be updated with new algorithms, more powerful programming, and/or more data. The clinical data server 240 and/or the algorithm server 245 may process the information and transmit data to the model database 270 for processing. In one example, algorithm server(s) 245 may obtain a pattern definition in a simple format, predict several time steps in the future by using models, e.g., Markov models, Gaussian, Bayesian, PCA (principal component analysis), multi-variate linear or non-linear regression, and/or classification models such as linear discriminant functions, nonlinear discriminant functions, synthetic discriminant functions random forest algorithms and the like, optimize results based on its predictions, detect transition between patterns, obtain abstract data and extract information to infer higher levels of knowledge, combine higher and lower levels of information to understand about the user 8 and clinical behaviors, infer from multi-temporal (e.g., different time scales) data and associated information, use variable order Markov models, and/or reduce noise over time by employing slope-based and curve smoothing algorithms, clustering algorithms, such as k-means clustering.

Each server in the system of servers 29, including clinical data server 240, algorithm server 245, and UI server 250, may represent any of various types of servers including, but not limited to, a web server, an application server, a proxy server, a network server, or a server farm. Each server in the system of servers 29 may be implemented using, for example, any general-purpose computer capable of serving data to other computing devices including, but not limited to, devices 19 or any other computing device (not shown) via network 32. Such a general-purpose computer can include, but is not limited to, a server device having a processor and memory for executing and storing instructions. The memory may include any type of random access memory (RAM) or read-only memory (ROM) embodied in a physical storage medium, such as magnetic storage including floppy disk, hard disk, or magnetic tape; semiconductor storage such as solid-state disk (SSD) or flash memory; optical disc storage; or magneto-optical disc storage. Software may include one or more applications and an operating system. Hardware can include, but is not limited to, a processor, memory, and graphical UI display. Each server also may have multiple processors and multiple shared or separate memory components that are configured to function together within, for example, a clustered computing environment or server farm.

Figure 3A:
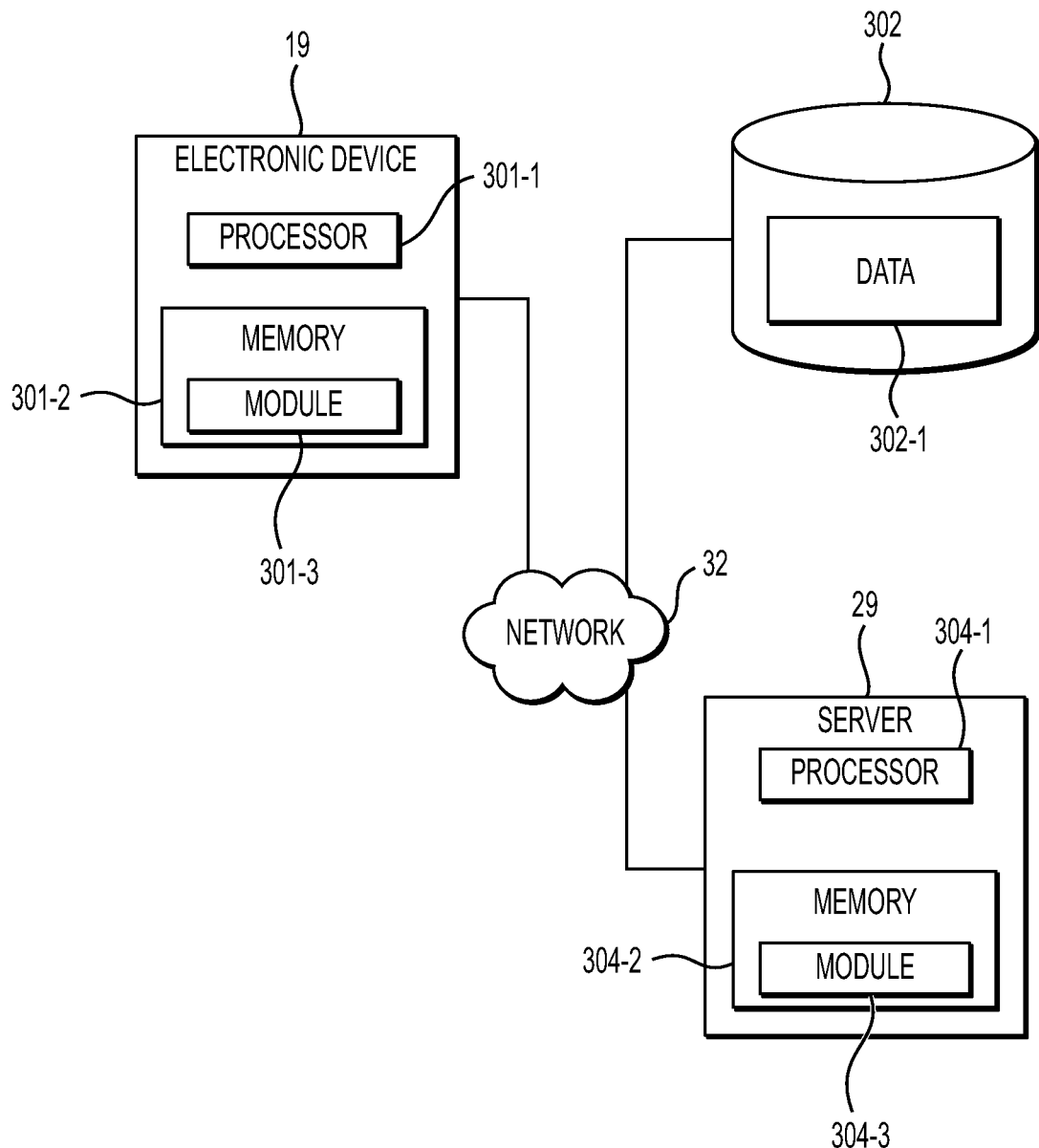
FIG. 3A is a schematic illustration of another portion of the health management system of FIG. 1.

FIG. 3A is another representation of a portion of system 100 showing additional details of electronic device 19 and a server 29. Electronic device 19 and server 29 each may contain one or more processors, such as processors 301-1 and 304-1. Processors 301-1 and 304-1 each may be a central processing unit, a microprocessor, a general purpose processor, an application specific processor, or any device that executes instructions. Electronic device 19 and server 29 also may include one or more memories, such as memories 301-2 and 304-2 that store one or more software modules. Memories 301-2 and 304-2 may be implemented using any computer-readable storage medium, such as hard drives, CDs, DVDs, flash memory, RAM, ROM, etc. Memory 301-2 may store a module 301-3, which may be executed by processor 301-1. Similarly, memory 304-2 may store a module 304-3, which may be executed by processor 304-1.

Electronic device 19 may further comprise one or more UIs. The UI may allow one or more interfaces to present information to a user 8, such as a plan or intervention. The UI may be web-based, such as a web page, or a stand-alone application. The UI also may be configured to accept information about a user 8, such as data inputs and user feedback. The user 8 may manually enter the information, or it may be entered automatically. In an example, the user 8 (or the user's caretaker) may enter information such as when medication was taken or what food and drink the user 8 consumed. Electronic device 19 also may include testing equipment (not shown) or an interface for receiving information from testing equipment. Testing equipment may include, for example, a blood glucose meter, glucose meter, heart rate monitor, weight scale, blood pressure cuff, or the like. The electronic device 19 also may include one or more sensors (not shown), such as a camera, microphone, or accelerometer, for collecting feedback from a user 8. In one example, the device may include a glucose meter for reading and automatically reporting the user's glucose levels.

Electronic device 19 also may include a presentation layer. The presentation layer may be a web browser, application, messaging interface (e.g., e-mail, instant message, SMS, etc.), etc. The electronic device 19 may present notifications, alerts, reading materials, references, guides, reminders, or suggestions to a user 8 via presentation layer. For example, the presentation layer may present articles that are determined to be relevant to the user 8, reminders to purchase medications, tutorials on topics (e.g., a tutorial on carbohydrates), testimonials from others with similar symptoms, and/or one or more goals (e.g., a carbohydrate counting goal). The presentation layer also may present information such as a tutorial (e.g., a user guide or instructional video) and/or enable communications between the healthcare provider, and the user 8, e.g., patient. The communications between the healthcare provider, and the user 8, e.g., patient, may be via electronic messaging (e.g., e-mail or SMS), voice, or real-time video. One or more of these items may be presented based on a treatment plan or an updated treatment plan, as described later. The presentation layer also may be used to receive feedback from a user.

The system 100 also may include one or more databases, such as a database 302. Database 302 may be implemented using any database technology known to one of ordinary skill in the art, such as relational database technology or object-oriented database technology. Database 302 may store data 302-1. Data 302-1 may include a knowledge base for making inferences, statistical models, and/or user information. Data 302-1, or portions thereof, may be alternatively or simultaneously stored in server 29 or electronic device 19.

System 100 can be used for a wide range of applications, including, for example, addressing a user's healthcare, maintaining a user's finances, and monitoring and tracking a user's nutrition and/or sleep. In some implementations of system 100, any received data may be stored in the databases in an encrypted form to increase security of the data against unauthorized access and complying with HIPAA privacy, and/or other legal, healthcare, financial, or other regulations.

For any server or server systems 29 depicted in system 100, the server or server system may include one or more databases. In an example, databases may be any type of data store or recording medium that may be used to store any type of data. For example, database 302 may store data received by or processed by server 29 including information related to a user's treatment plan, including timings and dosages associated with each prescribed medication of a treatment plan. Database 302 also may store information related to the user 8 including their literacy level related to each of a plurality of prescribed medications.

As further disclosed herein, one or more components of the disclosed subject matter may be implemented using a machine learning model. FIG. 3B shows an example training module 310 to train one or more of the machine learning models disclosed herein. It will be understood that a different training module may be used to train each of the machine learning models disclosed herein and/or a single training module 310 may be used to train two or more machine learning models.

As shown in FIG. 3B, training data 312 may include one or more of stage inputs 314 and known outcomes 318 related to a machine learning model to be trained. The stage inputs 314 may be from any applicable source including a healthcare provider 7, one or more servers 29, electronic devices 19, EMR 14, an output from a step (e.g., one or more outputs from a step from flowchart 500 of FIG. 5A or flowchart 900 of FIG. 9, time in range (TIR) values, time above range (TAR) values, time below range (TBR) values, severity score, continuous glucose monitoring (CGM) classification, etc.). The known outcomes 318 may be included for machine learning models generated based on supervised or semi-supervised training. An unsupervised machine learning model may not be trained using known outcomes 318. Known outputs 318 may include known or desired outputs for future inputs similar to or in the same category as stage inputs 314 that do not have corresponding known outputs.

The training data 312 and a training algorithm 320 may be provided to a training component 330 that may apply the training data 312 to the training algorithm 320 to generate a machine learning model. According to an implementation, the training component 330 may be provided comparison results 316 that compare a previous output of the corresponding machine learning model to apply the previous result to re-train the machine learning model. The comparison result 316 may be used by the training component 330 to update the corresponding machine learning model. The training algorithm 320 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

Health Conditions

Diabetes mellitus (commonly referred to as diabetes) may be a chronic, lifelong metabolic disease (or condition) in which a patient's body is unable to produce any or enough insulin, or is unable to use the insulin it does produce (insulin resistance), leading to elevated levels of glucose in the patient's blood. The three most identifiable types of diagnosed diabetes include: pre-diabetes, type 1 diabetes, and type 2 diabetes. Pre-diabetes is a condition in which blood sugar is high, but not high enough to be type 2 diabetes. Type 2 diabetes is a chronic condition that affects the way the body processes blood sugar. Lastly, type 1 diabetes is a chronic condition in which the pancreas produces little or no insulin.

Diabetes generally is diagnosed in several ways. Diagnosing diabetes may require repeated testing on multiple days to confirm the positive diagnosis of a types of diabetes. Some health parameters that doctors or other suitable healthcare providers use when confirming a diabetes diagnosis include glycated hemoglobin (A1C) levels in the blood, fasting plasma glucose (FPG) levels, oral glucose tolerance tests, and/or random plasma glucose tests. Commonly, a healthcare provider is interested in a patient's A1C level to assist in the diagnosis of diabetes. Glycated hemoglobin is a form of hemoglobin that is measured primarily to identify the three-month average plasma glucose concentration that may be used by doctors and/or other suitable healthcare providers include weight, age, nutritional intake, exercise activity, cholesterol levels, triglyceride levels, obesity, tobacco use, and family history.

Once a diagnosis of a type of diabetes is confirmed by a doctor or other suitable healthcare provider, the patient may undergo treatment to manage their diabetes. Patients having their diabetes tracked or monitored by a doctor or other healthcare provider may be treated by a combination of controlling their blood sugar through diet, exercise, oral medications, and/or insulin treatment. Regular screening for complications is also required for some patients. Depending on how long a patient has been diagnosed with diabetes, mHealth application 1 may suggest a specific treatment plan to manage their condition(s). Oral medications typically include pills taken by mouth to decrease the production of glucose by the liver and make muscle more sensitive to insulin. In other instances, where the diabetes is more severe, additional medication may be required for treating the patient's diabetes, including injections. An injection of basal insulin, also known as background insulin, may be used by healthcare providers to keep glucose levels at consistent levels during periods of fasting. When fasting, the patient's body steadily releases glucose into the blood to supply the cells with energy. An injection of basal insulin is therefore needed to keep glucose levels under control, and to allow the cells to take in glucose for energy. Basal insulin is usually taken once or twice a day depending on the type of insulin. Basal insulin acts over a relatively long period of time and therefore is considered long acting insulin or intermediate insulin. In contrast, a bolus insulin may be used to act quickly. For example, a bolus of insulin that may be specifically taken at meal times to keep glucose levels under control following a meal. In some instances, when a doctor or healthcare provider generates a treatment plan to manage a patient's diabetes, the doctor creates a basal-bolus dose regimen involving, e.g., taking a number of injections throughout the day. A basal-bolus regimen, which may include an injection at each meal, attempts to roughly emulate how a non-diabetic person's body delivers insulin. A basal-bolus regimen may be applicable to people with type 1 and type 2 diabetes. In addition to the basal-bolus regimen requiring injections of insulin, the treatment plan may be augmented with the use of prescribed oral medications. A patient's adherence to a treatment plan may be important in managing the disease state of the patient. In instances where the patient has been diagnosed with diabetes for more than six months, for example, a very specific treatment regimen must be followed by the patient to achieve healthy, or favorable, levels of glucose. Ultimately, weekly patterns of these medication types of treatments may be important in managing diabetes. A mHealth application 1 may recommend treatment plans to help patients manage their diabetes.

Exemplary Methods

Diabetes is a chronic condition that results in a patient unable to keep glucose within a normal or recommended target range. Such fluctuating glucose levels (i.e., outside the normal or recommended target range) can lead to significant health complications. Developing meaningful insights is difficult with sporadic blood glucose monitoring (BGM), where only a handful of intermittent readings in a week may not serve a basis to understand patterns, and any underlying causes for those patterns (e.g., determining a rising BGM based on a meal type).

Continuous glucose monitoring (CGM) provides the possibility for dense data (e.g., data based on a collection frequency of every 5 minutes or less) to be automatically gathered through wearable sensors (e.g., sub-cutaneous sensors) that provide a periodic glucose value (e.g., a user 8's glucose levels). CGM can improve diabetes care by providing a continuous (e.g., every five minutes or less) or semi-continuous (e.g., more than every five minutes) readout of glucose data to user 8 or other entities (e.g., healthcare provider 7) so that the user 8 or other entities can be more aware of the user 8's glucose levels at all times of the day. Such data may allow a healthcare provider 7 to adjust treatment plans for user 8 more optimally.

A CGM monitor may be a continuous analyte sensor system that includes any sensor configuration that provides an output signal indicative of a concentration of an analyte. The CGM monitor may sense the concentration of the analyte to determine, for example, glucose values, based on a bodily fluid (e.g., interstitial fluid). The bodily fluid may be accessed through a user's skin. The output signal, which may be in the form of, for example, sensor data, such as a raw data stream, filtered data, smoothed data, and/or otherwise transformed sensor data, may be sent to a receiver, which may be connected to the CGM monitor via a wired or wireless connection and may be local or remote from the sensor. According to implementations, the CGM monitor may include a transcutaneous glucose sensor, a subcutaneous glucose sensor, a continuous refillable subcutaneous glucose sensor, a continuous intravascular glucose sensor, or the like. The CGM monitor may be a compact medical system with one or more sensors that is inserted onto a user 8's abdomen and that includes a small cannula that penetrates the user 8's skin. An adhesive patch may hold the monitor in place. The sensor may sense glucose readings in interstitial fluid on a continuous or semi-continuous basis.

A transmitter may be connected to the sensor to allow the CGM monitor to send the glucose readings wirelessly to a monitoring device. The monitoring device may be a CGM monitor specific monitoring device, may be a third party device, an electronic device 19, or any other applicable device. The monitoring device may be a dedicated monitoring device or an electronic device 19 that provides one or more functions in addition to the CGM monitoring. An application or other software may be used to facilitate the analysis and/or display of the glucose readings and associated data via the monitoring device. The monitoring device may be used to analyze and/or view the data associated with the glucose readings. Alternatively, or in addition, the CGM monitor may include a display to view glucose readings and/or associated data. The CGM monitor and/or external device may be configured to generate and/or provide alerts based on the glucose data (e.g., if blood sugar levels are too high or too low, or showing an unfavorable trend).

By using CGM data, a time in range (TIR) value can be determined where a TIR value is based on an amount of time a user 8's glucose level is within a threshold band over a base time period. The threshold band may be pre-determined, be user specific, or may be dynamically determined.

The threshold band may be a pre-determined value based on, for example, a cohort of patients. The lifestyle, habits, medical test results for each of the patients in a cohort may be used to determine the pre-determined value. For example, one or more cohorts of patients may be determined based on the patient's lifestyle, habits, demographics, or the like, and a threshold band may be generated for each of the one or more cohorts. The threshold band may be determined based on optimal results (e.g., preferred A1C values) based on an analysis of glucose levels over a period of time. For example, a machine learning model may be generated using training module 310. The machine learning model may be trained using the glucose levels of a cohort of patients as stage inputs 314 and may receive the corresponding A1C values as known outcomes 318. The training machine learning model may receive, as inputs, data (e.g., A1C values) of a cohort of patients and may output a threshold band (i.e., with an upper glucose limit and a lower glucose limit) of glucose levels for that cohort of patients. Alternatively, the threshold band may be a pre-determined value for a general population such that it is not cohort specific. According to implementations, a TIR threshold band is between approximately 70 mg/dL and approximately 180 mg/dL. A TIR value may be the amount of time that user 8's glucose level is within the TIR threshold band for a base period of time. According to implementations of the disclosed subject matter, the base period of time may be 24 hours though it will be understood that more granular changes in TIR values may be determined based on reducing the base period of time to be less than 24 hours and broader changes may be determined based on increasing the base period of time to be greater than 24 hours.

A user-specific threshold band may be determined based on attributes about a user 8. The attributes may be medical history, physical history, demographics, or the like. According to an implementation, the user-specific threshold may be generated using a machine learning model trained using training module 310. The machine learning model may receive updated attributes based on user 8 and, may re-train itself via using the updated attributes through the comparison results 316 component. As an example, a change in user 8's weight may be a change in attribute that is provided to the comparison results 316 component such that the machine learning model updates a previously provided threshold band based on the updated weight. Accordingly, a user-specific threshold band may change from time to time, based on one or more attributes of the user 8. Similarly, a dynamically determined threshold band may be determined based on changes in one or more attributes related to the user 8, a cohort of users, external conditions, environmental conditions, updated recommendations, or the like.

As applied herein, a user vector (e.g., patient vector) may be any behavior, activity, good (e.g., consumable good), service, parameter, or value that is or can be associated with a given patient and that can be changed. A patient vector may be changed to improve a TIR state or a GV state of a user 8, as further disclosed herein. As examples, a patient vector may include one or more of medications, food consumption properties, exercise values, psycho-social parameters, social-determinant parameters, or the like.

As applied herein, a user attribute (e.g., patient attribute) may be an attribute or characteristic associate with a patient. As compared to a patient vector, a patient attribute may be one that cannot be easily modified or changed. As examples, patient attributes may include a social attribute, medical history or condition, patient preference, metabolic attribute, patient demographic, or the like.

Figure 4A:
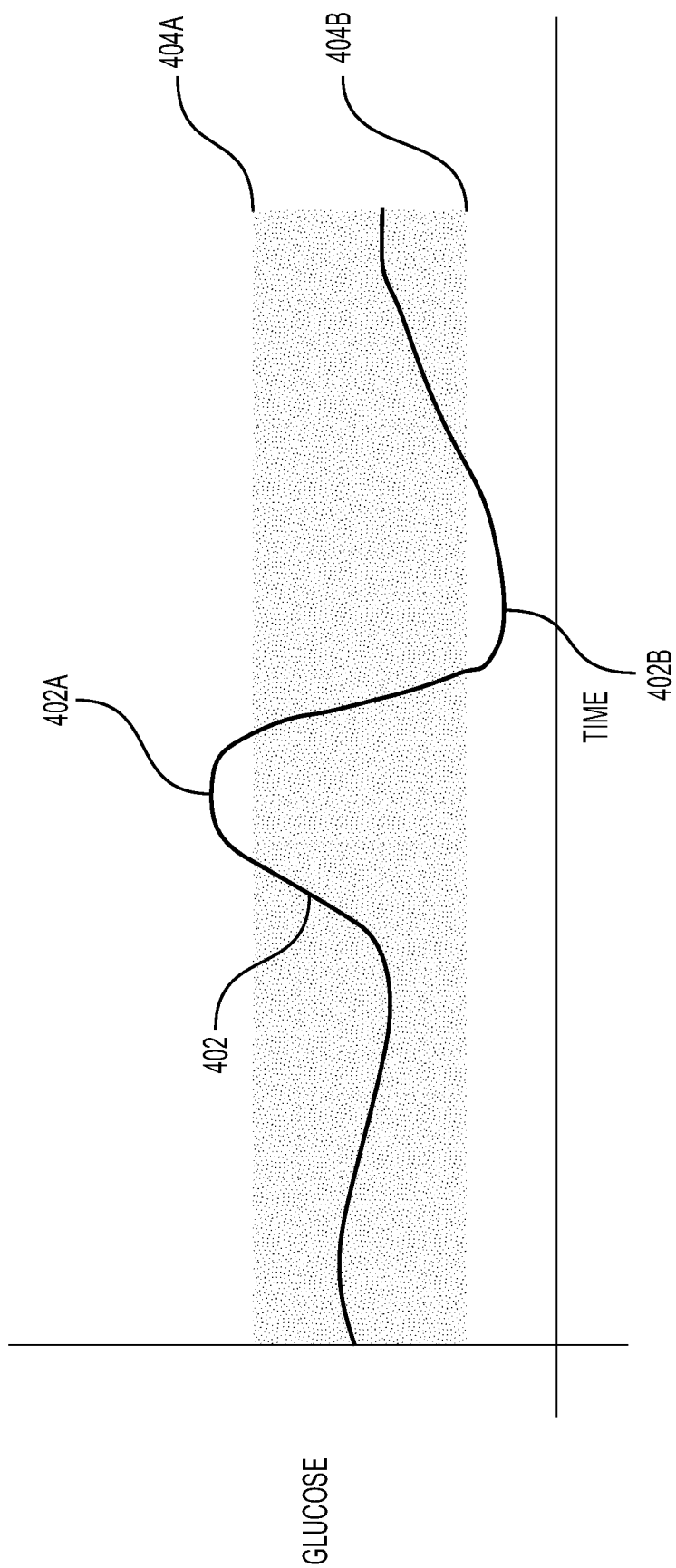
FIG. 4A is a continuous glucose monitoring (CGM) chart, according to an example of the present disclosure.

FIG. 4A shows an example CGM based glucose level trace 402 for a user 8. The time period shown via FIG. 4A may be a full day (i.e., 24 hour period). As shown, the user 8's glucose level may have a TIR by being within a threshold range represented by an upper threshold 404A and a lower threshold 404B for a portion of the day except for during TAR duration 402A and a TBR duration 402B. User 8 may be provided such a graphical display during the day or after the completion of the day. Accordingly, the CGM data may be provided to user 8 and inform user 8 of her current glucose levels and/or trends associated with her current glucose levels.

FIG. 4B shows an example CGM based report 406 which may be provided to user 8 or a healthcare provider 7. The report may be in an Ambulatory Glucose Profile (AGP) format and may include a number of metrics (e.g., 10 metrics) as well as graphical data. The report may include glucose statistics and targets 408, an AGP profile 410, daily glucose profiles 412, time ranges 414, and the like. However, most patients with diabetes may not be able to interpret such CGM data and/or AGP information to affect change in glucose levels. Similarly, healthcare providers 7 may require multiple patient consultations to interpret the data provided via CGM monitoring and/or AGP information to even temporarily optimize glucose levels. Techniques disclosed herein provide tracking of essential parameters to manage user 8's health.

According to implementations disclosed herein, the CGM data may be used to recommend changes based on one or more patient vectors, as further disclosed herein. A CGM event (e.g., a change in CGM state, a portion of a CGM trace, etc.) may be defined as a discernable region of a CGM tracing that is correlated to a diabetes self-management activity (DSMA). A CGM trace may be used to identify a CGM trend or may be a CGM trend, as further applied herein. A DSMA may be a change in or addition of a medication, a change in or addition of a food, a change in or addition of an exercise, or the like. The CGM may drive automated coaching to a user 8. Similarly, the CGM based outcome (e.g., an outcome in glucose properties based on the automated coaching and/or DSMA) may drive coaching for future DSMA and/or provide tailored and specific decision-support for healthcare providers 7.

Figure 5A:
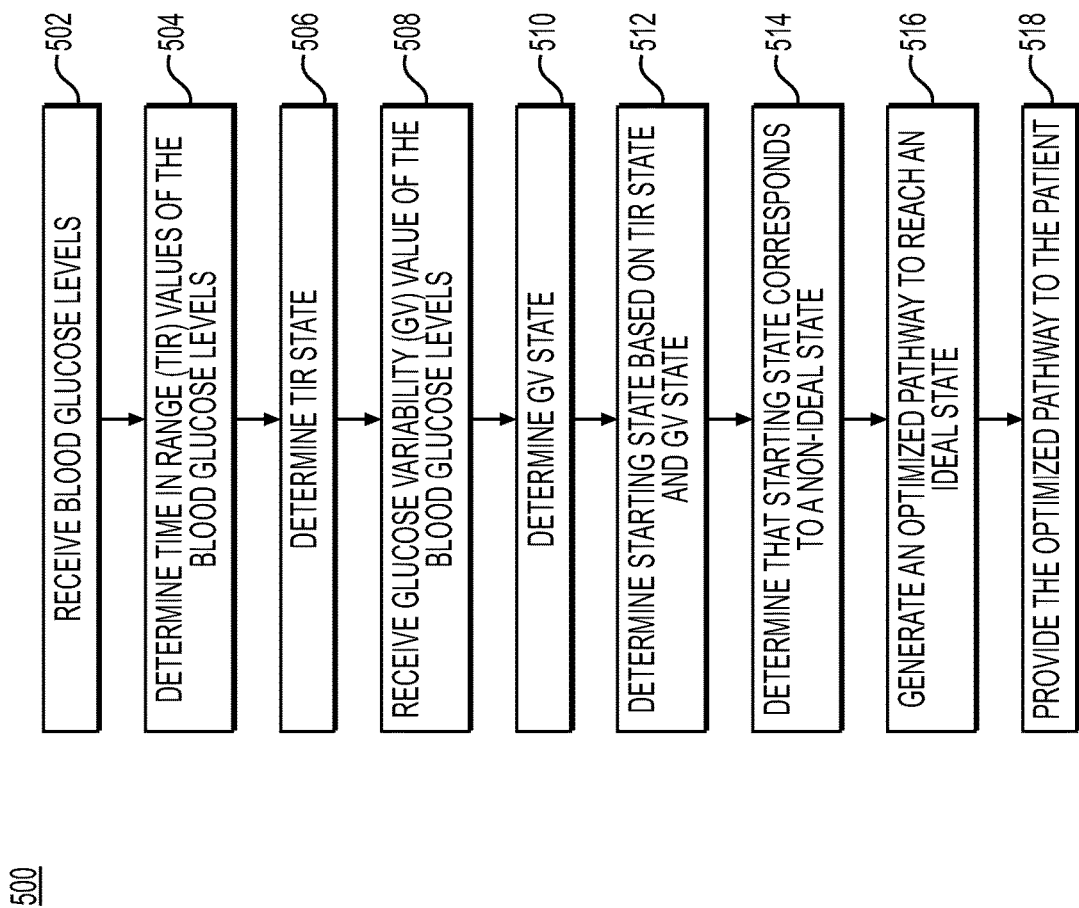
FIG. 5A is a flowchart of a health management method, according to an example of the present disclosure.

According to implementations, a detect, inform, classify, and engage (DICE) framework may outline techniques to detect various diabetes related events from a CGM trace, inform a healthcare provider 7 and/or user 8 about the progress along an optimized pathway via one or more visualizations, classify a detected event into one or more classes and/or 2D CGM quadrant starting states for additional intervention, and/or engage and coach patients towards improved outcomes. The techniques associated with the DICE framework synthesize data from multiple domains such as metabolic data, lifestyle data, socioeconomic data, clinical data, and the like to enhance patient care. The automated CGM event detection and classifications techniques disclosed herein allow enhanced quality of care by increasing accuracy and reducing errors. Automated coaching based on various quantitative methodologies allows scalability and increased reach of every patient in need of care and/or support. The visualizations provided herein reduce the data burden on a user 8 and/or healthcare provider 7 by distilling dense CGM data and other applicable data into easy to consume charts, graphs, and/or other visualizations. FIG. 5A shows a method 500 for providing optimized pathways for improving the glucose state of a user 8. At 502, a user 8's glucose levels may be received. The glucose levels may be provided on a continuous or semi-continuous basis by a CGM monitor, as disclosed herein. The glucose levels may be received at a component of the CGM monitor itself or may be received at a local or remote component such as an electronic device 19, mHealth application 1, one or more servers 29, or the like. The glucose levels may be provided automatically from the CGM monitor to one or more components, may be pushed upon collection of glucose levels, or the CGM monitor may be pinged to transmit one or more collected glucose levels.

As an example, a user 8 may attach a CGM monitor to her body and the CGM monitor may collect glucose level readings every five minutes. The CGM monitor may be connected to the user 8's mobile device (e.g., via a network connection, local area network connection, wide area network connection, WiFi connection, Bluetooth® connection, etc.). According to a first example implementation, the CGM monitor may automatically transmit a glucose level reading to user 8's mobile device each time a reading is collected (e.g., every 5 minutes). Alternatively, or in addition, the CGM monitor may store one or more glucose level readings such that they are sent to the user 8's mobile device as a group of multiple readings and/or when the user 8's mobile device or another component requests that the one or more glucose level readings are transmitted.

At 504 of FIG. 5A, time in range (TIR) values associated with the glucose level readings are determined. In range glucose values may correspond to the amount of time glucose level readings are within a given range, ratio of glucose level readings within range to out of range, count of glucose level readings in range to out of range or the like. The TIR values may distinguish the user 8's glucose levels from the times when they are within the range to the times when they are outside of the range. As shown in FIG. 4A, the glucose levels may be considered in range when within an upper threshold 404A and a lower threshold 404B. The upper threshold 404A may be 180 mg/dL and the lower threshold 404B may be 70 mg/dL such that a TIR value for a given patient may correspond to the amount of time that the patient's glucose levels are between 70 mg/dL and 180 mg/dL.

The TIR value determined at 504 of FIG. 5A may be based on an amount of time user 8's glucose level is within a threshold band over a base period of time. The base period of time may be a single 24 hour day or may be a different base period. The base period may be pre-determined (e.g., by user 8, by a healthcare provider 7, pre-programmed, etc.), or may be dynamically determined based on one or more factors. The one or more factors may be patient vectors, patient attributes, a current or previous TIR state, or the like.

According to an implementation, the TIR value may be for the base period or may be a TIR value associated with the patient over a number of base periods. For example, a TIR value for user 8 may be determined for each day for a total of ten days. The TIR value from each of the 10 days may be combined using any applicable technique (e.g., an average) such that the TIR associated with the user 8 over the ten days is the combined TIR value.

According to an implementation, the TIR value may be filtered such that anomalies in glucose levels are removed or weighted less then glucose level readings that are not flagged as anomalies. As an example, a glucose level reading of 65 mg/dL during a first reading may increase to 200 mg/dL in the very next second reading five minutes after the first reading. A third reading five minutes after the second reading may indicate a glucose level of 68 mg/dL. A filter such as one using a density-based techniques (e.g., k-nearest neighbor, local outlier factor, isolation forests, etc.), one using subspace, correlation-based, and/or tensor-based outlier detection for high-dimensional data, one using one-class support vector machines, one using replicator neural networks, autoencoders, variational autoencoders, long short-term memory neural networks, one using Bayesian networks, one using Hidden Markov models (HMMs), one using cluster analysis-based outlier detection, one using deviations from association rules and frequent item sets, one using fuzzy logic-based outlier detection, one using ensemble techniques, using feature bagging, score normalization and different sources of diversity, one using convolutional LSTM with mixtures of probabilistic principal component analyzers, and/or the like may be used to identify anomalies and/or glucose level reading that may be read in error, may be insignificant outliers, or the like. One or more of such filtering techniques may also be using with machine learning models disclosed herein. According to this implementation, a TIR value associated with user 8 may be in view of the glucose level readings being filtered through such one or more filters. Such filtering may prevent providing optimized pathways, as further disclosed, that are tainted due to anomalies, outlier data, and/or irregular readings.

At 506 of FIG. 5A, a TIR state for the user 8 may be determined based on the one or more TIR values associated with the user 8. The TIR state may be a state associated with the TIR value alone or may be based on one or more other factors (e.g., frequency of glucose readings, quality of glucose readings, another sensed reading, a patient-based factor, etc.). For simplicity, this disclosure will discuss a TIR binary state based on TIR values alone (i.e., a good TIR state and a bad TIR state). However, it will be understood that the TIR state may be a multi-dimensional state based on the TIR value and one or more other factors. As applied herein a good TIR state (e.g., a first TIR state) corresponds to a TIR ratio greater than a TIR cutoff and a bad TIR state (e.g., a second TIR state) corresponds to a TIR ratio less than the TIR cutoff.

Figure 6A:
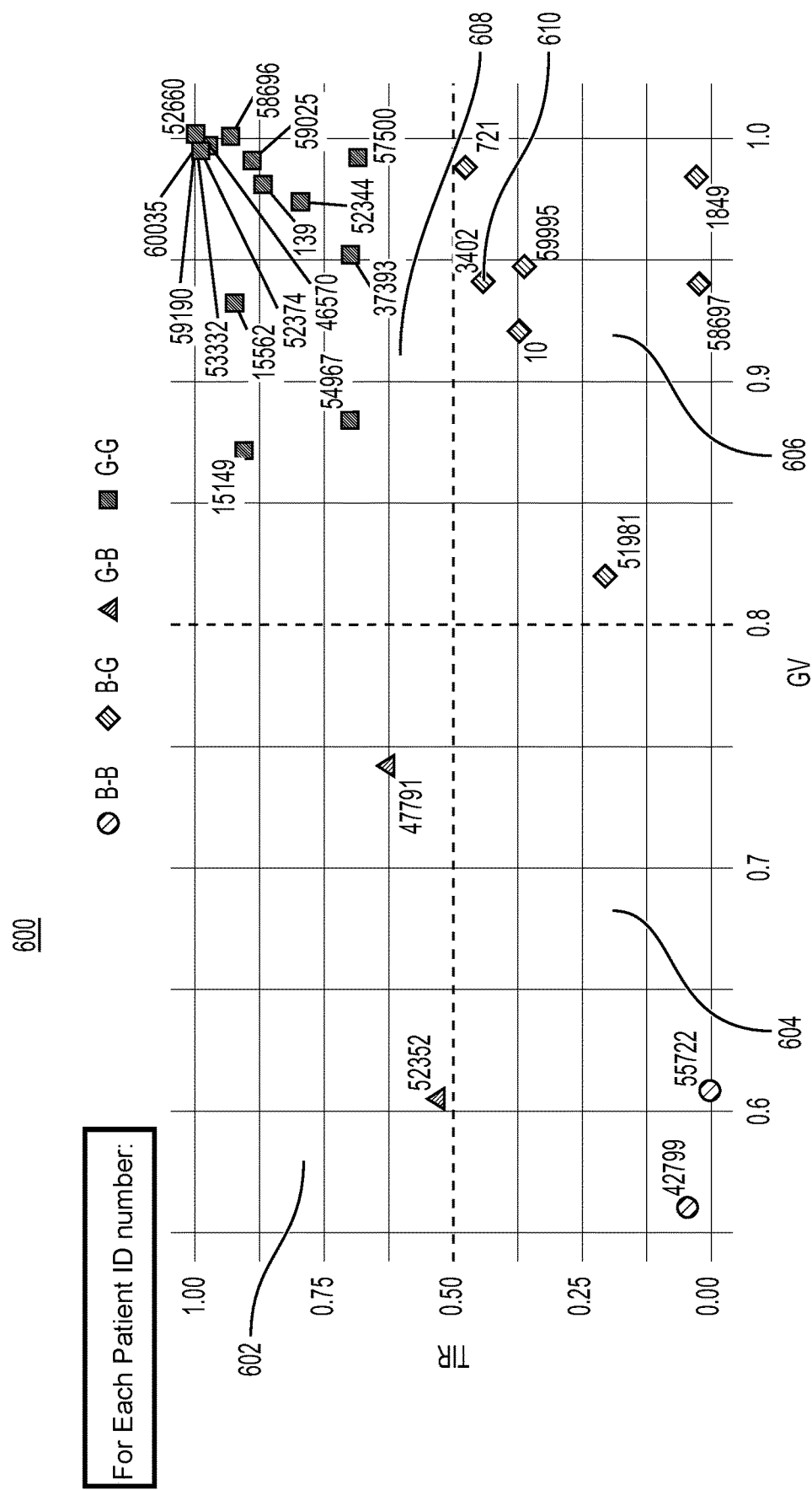
FIG. 6A is a patient state graph, according to another example of the present disclosure.

FIG. 6A shows a chart 600 of TIR states for a plurality of different patients. The chart includes four quadrants based on a TIR ratio and a GV ratio, as further disclosed herein. The TIR state is based on the TIR axis which corresponds to the Y access in the chart 600. The TIR ratio is the percentage of time over the base time period that the glucose levels of a patient are within the threshold band. Alternatively, the TIR ratio may be the percentage of time over the base time period that the glucose levels of a patient are within the threshold band for multiple base time periods, such that the TIR ratio is a computed (e.g., averaged) value over the multiple base time periods.

A TIR ratio value may be designated as a cutoff for a good TIR state versus a bad TIR state. Chart 600 of FIG. 6A includes a cutoff of 0.5 such that a TIR ratio above 0.5 is considered a good TIR state (e.g., where a user 8's glucose level is within a threshold band for over 50% of the time or calculated readings) and a TIR ratio below 0.5 is considered a bad TIR state (e.g., where a user 8's glucose level is outside the threshold band for over 50% of the time or calculated readings). The cutoff may be pre-determined or dynamically determined. A pre-determined cutoff may be based on a medical standard or may be designated by a healthcare provider 7 for a cohort or a user 8. A dynamically determined cutoff may be based on a cohort or a given user 8 and may be determined by a machine learning model. The machine learning model may receive, as inputs, patient vectors, patient attributes, past patient TIR or GV values or changes, or the like and may output a cutoff specifically for a user 8 or cohort that the inputs are associated with. Accordingly, the cutoff may be tailored to a value that is considered optimal for the corresponding user 8 or cohort that the input data was based on.

As shown in chart 600, patients with a TIR value above the cutoff of 0.5 are considered to have good TIR state and patients with a TIR value below the cutoff of 0.5 are considered to be in a bad TIR state. It will be understood that if the cutoff was shifted, the number of patients with good or bad TIR states would change accordingly. For example, if the TIR ratio was adjusted to 0.9 instead of 0.5, most patients would be in a bad TIR state.

At 508, of FIG. 5A, glucose variability (GV) values associated with the glucose level readings for a given user 8 are determined. Glucose variability values may measure the amount of change in glucose over a time period to utilize the fluctuations in glucose values to improve diabetes management. A GV value may be a standard deviation (SD) value, a coefficient of variance (CV) or any other applicable fluctuation measurement value.

The SD may be a measure of the amount of variation or dispersion of a set of glucose values (e.g., collected over an hour, over a day, or any other applicable period of time). A low SD may indicate that the glucose values tend to be close to a mean of the set of glucose values. A high SD may indicate that the values are spread out over a wider range. The SD of glucose values may be the square root of the variance of the glucose values. The SD of glucose values may be calculated as shown in Equation 1:

$$\sigma = \sqrt{\frac{\Sigma |x - \mu|^2}{N}} \qquad \text{(Equation 1)}$$

Where x is each of a glucose value in a set of glucose values associated with the patient, μ is the mean of the glucose values in the set of glucose values associated with the patient, and N is the number of data points in the set of glucose values associated with the patient.

A CV may be a standardized measure of dispersion of a probability distribution or frequency distribution. The CV for a patient's glucose levels may be calculated by determining the ratio of the standard deviation of the glucose levels to the mean of the glucose levels. The CV may shows the extent of variability in relation to the mean of the glucose levels over a period of time. The CV may be calculated as shown in Equation 2:

$$Cv = \frac{\sigma}{\mu} \quad \text{(Equation 2)}$$

As stated, the GV value may be a SD value or a CV value. According to an implementation, the type of GV value (e.g., SD value, CV value, etc.) may be based on a user 8 or may be based on current or historical patent vectors, patient attributes, or other information related to user 8. According to another implementation, the type of GV value may be determined by a healthcare provider 7 or by a machine learning model configured to output the optimal type of GV value based on one or more inputs such as patient vectors, patient attributes, historical analysis, or the like.

At 510 of FIG. 5A, a GV state for the user 8 may be determined based on the one or more GV values associated with the user 8. The GV state may be a state associated with the GV value alone or may be based on one or more other factors (e.g., frequency of glucose readings, quality of glucose readings, another sensed reading, a patient-based factor, etc.). For simplicity, this disclosure will discuss a GV binary state based on GV values alone (i.e., a good GV state and a bad GV state). However, it will be understood that the GV state may be a multi-dimensional state based on the GV value and one or more other factors. As applied herein a good GV state (e.g., a first GV state) corresponds to a GV value greater than a GV cutoff and a bad GV state (e.g., a second GV state) corresponds to a GV value less than the GV cutoff.

FIG. 6A shows a chart 600 of GV states for a plurality of different patients. The chart includes four quadrants based on a TIR ratio and a GV, as disclosed herein. The GV state is based on the GV axis which corresponds to the X access in the chart 600. The GV may be the SD or CV associated with the glucose level of a patient over a period of time. Alternatively, the GV may be the SD or CV associated with the glucose level of a patient over multiple periods of time, such that the GV is a computed (e.g., averaged) value over the multiple time periods.

A GV value may be designated as a cutoff for a good GV state versus a bad GV state. Chart 600 of FIG. 6A includes a cutoff of 0.8 such that a GV value above 0.8 is considered a good GV state and a GV value below 0.8 is considered a bad GV state. The cutoff may be pre-determined or dynamically determined. A pre-determined cutoff may be based on a medical standard or may be designated by a healthcare provider 7 for a cohort or a user 8. A dynamically determined cutoff may be based on a cohort or a given user 8 and may be determined by a machine learning model. The machine learning model may receive, as inputs, patient vectors, patient attributes, past patient TIR or GV values or changes, or the like and may output a cutoff specifically for a user 8 or cohort that the inputs are associated with. Accordingly, the cutoff may be tailored to a value that is considered optimal for the corresponding user 8 or cohort that the input data was based on.

As shown in chart 600, patients with a GV value above the cutoff of 0.8 are considered to have good GV state and patients with a GV value below the cutoff of 0.8 are considered to be in a bad GV state. It will be understood that if the cutoff was shifted, the number of patients with good or bad GV states would change accordingly. For example, if the GV value was adjusted to 0.9 instead of 0.8, more patients would be in a bad GV state than when compared to when the cutoff is 0.8. According to an implementation, an optimal cutoff value for distinguishing between a good state and a bad state may be 0.7.

As shown in FIG. 6A, four quadrants are created based on the Y axis (TIR ratios) and X axis (GV values) segregated based on a TIR cutoff value (i.e. 0.5 in the example shown in FIG. 6A) and GV cutoff value (i.e., 0.8 in the example shown in FIG. 6A). Patients in the top left quadrant 602 correspond to those within a good TIR state (i.e., above a TIR cutoff) and a bad GV state (i.e., lower than a cutoff GV). This state may be considered a Good-Bad (G-B) state where the first characterization (i.e., Good) corresponds to a TIR state and the second characterization (i.e., Bad) corresponds to a GV state. Patients in the bottom left quadrant 604 correspond to those within a bad TIR state (i.e., below a TIR cutoff) and a bad GV state (i.e., lower than a cutoff GV). This state may be considered a Bad-Bad (B-B) state. Patients in the bottom right quadrant 606 correspond to those within a bad TIR state (i.e., below a TIR cutoff) and a good GV state (i.e., higher than a cutoff GV). This state may be considered a Bad-Good (B-G) state. Patients in the bottom left quadrant 604 correspond to those within a bad TIR state (i.e., below a TIR cutoff) and a bad GV state (i.e., lower than a cutoff GV). This state may be considered a Bad-Bad (B-B) state. Patients in each of the quadrants 602, 604, and 606 may be considered patients having non-ideal states such that at least one of the TIR state or the GV state is a non-optimal state (e.g., a "bad" state). Patients in the top right quadrant 606 correspond to those within a good TIR state (i.e., above a TIR cutoff) and a good GV state (i.e., higher than a cutoff GV). This state may be considered a Good-Good (G-G) state. Patients in quadrant 608 may be considered patients in an ideal state such that both of the TIR state and the GV state is an optimal state (e.g., a "good" state).

As shown at 512 of FIG. 5A, the starting state for a given patient may be based on the patient's TIR state and GV state. The starting state for a user 8 may correspond to the quadrant that the user 8's TIR state and GV state falls into, as shown in FIG. 6A. For example, a user 610, as shown in FIG. 6A, may have a TIR ratio that does not meet the TIR cutoff and, thus, is in a Bad TIR state and a GV that is higher than the GV cutoff and, thus, is in a Good GV state. Accordingly, the user 610 may be in a non-ideal starting Bad-Good state, represented by the bottom right quadrant 606 in the example shown in FIG. 6A, as determined at 514 of FIG. 5A. The non-ideal starting Bad-Good overall state of user 610 may be the user 610's state at a point in time and may change over time, as further disclosed herein.

A non-ideal starting state, as determined at 514 of FIG. 5A may indicate that a user 8's diabetes management is not optimal. For example, a non-ideal starting state may indicate a low TIR and/or a non-optimal GV. Accordingly, a non-ideal starting state may require an adjustment to the corresponding user 8's diabetes management such that the user 8's state can change from the non-ideal state to an ideal-state.

According to an implementation, the two dimensional framework described herein and as shown in FIG. 6A may be implemented into a production system via a novel data integration Extract, Transform, Load (ETL) process. The process may extract the CGM data obtained by a CGM monitor and analyzed by either the CGM monitor, an electronic device 19, and/or any other applicable component. The extracted data may be transformed and/or loaded into a production database that may include one or more machine learning models and may determine a starting state (e.g., at 512 of FIG. 5A).

Accordingly, in a macro view of the state based data of a user 8 (e.g., a starting state) can be represented by two orthogonal parameters, the TIR state and the GV state. As disclosed herein, the corresponding state may be visualized and reported to the user 8, healthcare provider 7, or the like, to assess an overall glucose health status (e.g., as shown in FIG. 6A). The state based data may be used to provide overall glucose health recommendations (e.g., via an optimized pathway, as further disclosed herein).

At 516 of FIG. 5A, an optimized pathway to reach an ideal state may be generated. The optimized pathway may be one or more adjustments to one or more patient vectors and may be determined based on the non-ideal state (i.e., Good-Bad, Bad-Bad, or Bad-Good states), patient vectors, and/or patient attributes. The optimized pathway may be adjustments to one or more patient vectors including, but not limited to, medications, food consumption properties, exercise values, psycho-social parameters, and/or social-determinant parameters.

An adjustment to medication may be provided based on a user 8's current medications or may be based on new medications that the user 8 may be provided. The adjustment may be made by adjusting a dose of a medicine, by adding or removing a medicine, by changing the time or frequency a medicine is consumed, by changing the environment (e.g., the type of food consumed with the medication) associated with the medication, or the like. For example, consumption of a specific medication that user 8 is currently consuming may be adjusted to a higher dose.

An adjustment to food consumption properties may including changing, removing, adding, or otherwise modifying one or more foods, food groups, food types, food consumption times, food pairings, food and medication pairings, or the like. For example, based on a patient attribute indicating that the glucose level of a patient increases beyond the threshold band after consuming food, the patient may be provided an alert to consume food during times when a current glucose level is low.

An adjustment to exercise values may include changing, removing, adding, or otherwise modifying one or more exercises, exercise types, exercise durations, exercise times, or the like. For example, the GV for a given patient may be more stable if the patient exercise earlier in the day and, thus, an adjustment may be made to prioritize exercising in the morning.

Psycho-social parameters and/or social-determinant parameters may also be adjusted or modified and may include changing, removing, adding, or otherwise modifying meditation schedules or types, social activities, interactions, and/or durations or frequencies of the same.

An optimized pathway may be generated at 516 using a machine learning model. The machine learning model may be trained as shown in FIG. 3B. The machine learning model may receive, as inputs, one or more of patient vectors, the starting state (e.g., TIR state, GV state, Good-Bad state, Bad-Bad state, Bad-Good state, etc.), patient attributes, and CGM properties. The machine learning model may produce an output of an optimized pathway based on such inputs. The optimized pathway may be an adjustment to one or multiple patient vectors, as disclosed herein.

At 518 of FIG. 5A, the optimized pathway may be provided to the patient directly (e.g., to a user 8 via mHealth application 1, using an electronic device 19, etc.), may be provided a healthcare provider 7, or to both. The optimized pathway may be an outline of changes to one or more patient vectors, may be an automatic adjustment to one or more patient vectors, or may be provided incrementally based on one or more actions, timings, levels, values, or the like. An incrementally provided optimized pathway may be provided based on the corresponding one or more patient vectors to cause change to the one or more patient vectors. As an example, if a change to a patient vector includes consuming food when the patient's glucose level is at a lower end of the threshold band, a mobile device alert may be provided when the patient's CGM monitor records such a glucose level. The mobile device alert may provide an indication to the user that the user should consume food within a given time period based on the alert.

An optimized pathway may also be provided on a periodic basis (e.g., daily, hourly, weekly, etc.) or based on triggers, where the pre-determined times are based on the changes based on the optimized pathway. For example, an optimized pathway that makes modifications to a patient's eating schedule may be provided using alerts during meal times. As another example, an optimized pathway that makes modifications to a patient's medication may be provided using alerts during medication delivery times.

The frequency, manner, and/or mode of providing an optimized pathway may be based on the primary actions or variables associated with successful implementation of the optimized pathway. A habit index may be determined for a patient or a cohort of patients with one or more like attributes. The habit index may be a categorization of the patient's behavior and may be a habit designation (e.g., frequent communication, in-frequent communication, technological communication, telephonic communication, human communication, graphic communication, time of day communication, etc.), may be a value or score, or may be any other applicable designation that provides an indication of a patient's behavior to properly tailor providing an optimized pathway.

A habit index may be determined based on habit or preferences including frequency-based factors, time-cue based factors, context-cue based factors, and/or the like. The habit index may be used to provide a patient's optimized pathway to the patient such that the optimized pathway may be provided in accordance with the habit index. As an example, a habit index may indicate that a user 8 prefers minimal communication and prefers any communication to be conducted via mHealth application. Accordingly, the patient vector changes via an optimized pathway may be provided to user 8 via the mHealth application once a day. Accordingly, a habit index may be used to provide an optimized pathway to a patient in a personalized manner based on the patients individual behavior preferences.

Figure 5B:
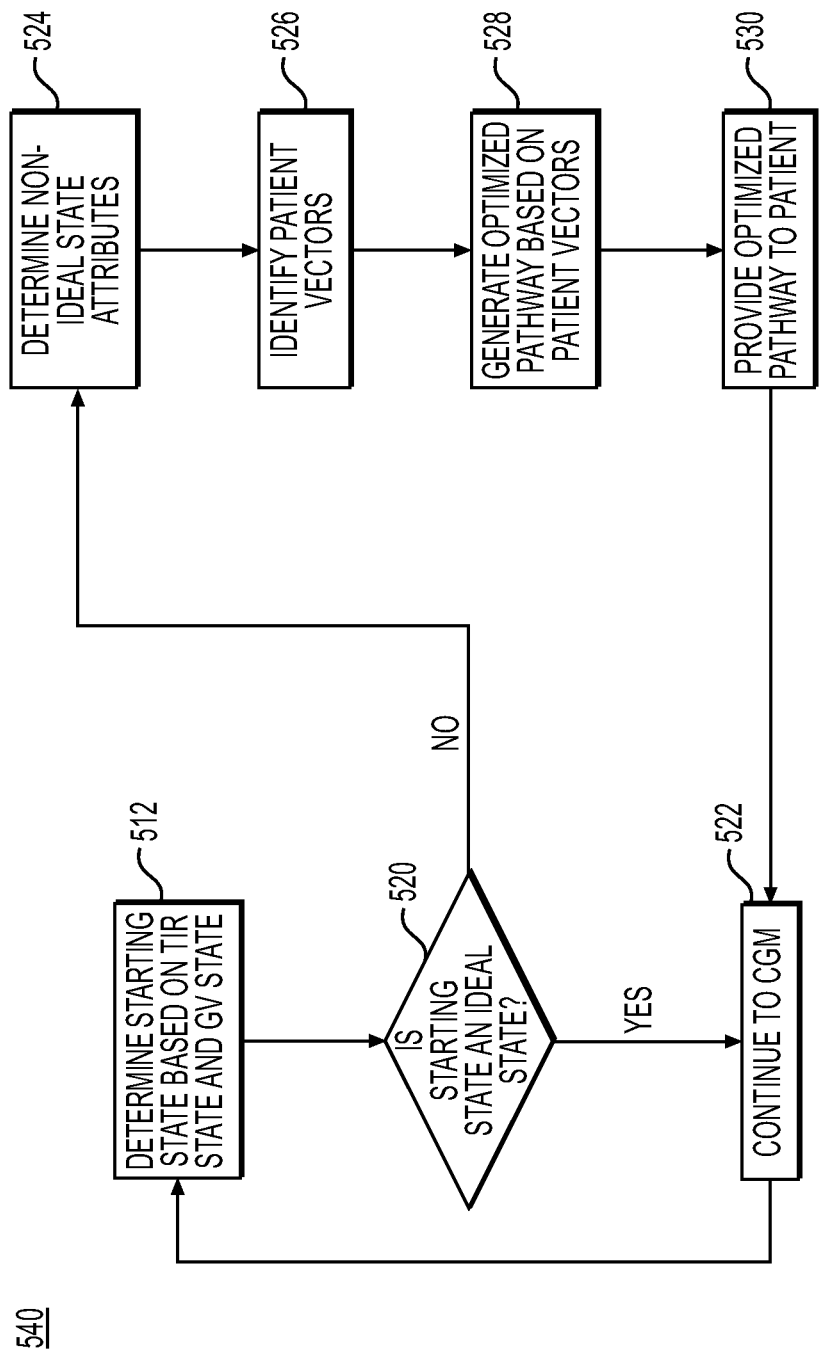
FIG. 5B is a flowchart of an exemplary health management method, according to another example of the present disclosure.

FIG. 5B shows an example implementation flowchart 540 based on CGM. Step 512 of FIG. 5B corresponds to step 512 of FIG. 5A and includes determining a starting state for a given patient based on the patient's TIR state and GV state, as disclosed herein. At 520, a determination regarding whether the starting state determined at 512 is an ideal state. If the starting state is an ideal state, at 522, a CGM monitor may continue to perform CGM. If the starting state is not an ideal state (i.e., a non-ideal state such as a Good-Bad, Bad-Bad, or Bad-Good state), then, at 524, one or more non-ideal state attributes may be determined. The non-ideal state attributes may be the values of TIR or GV, changes in TIR or GV, or the like. At 526, patient vectors associated with the patient may be identified. The patient vectors may be provided by a user 8, by a healthcare provider 7, obtained via electronic device 19, via servers 29, or any other applicable means.

At 528, an optimized pathway to transition the patient from the non-ideal state to an ideal state may be generated. It will be understood that a reaching an intermediate non-ideal state may be part of reaching an ideal state. For example, a patient with a starting non-ideal state of Bad-Bad (i.e., a bad TIR state and a bad GV state) may be provided an optimized pathway that first transitions the patient to a Good-Bad or a Bad-Good state before reaching a Good-Good state. A machine learning model may output the optimized pathway including one or more patient vector changes based on inputs that include one or more of a TIR state or value, GV state or value, one or more patient vectors, one or more patient properties, a CGM event, and/or the like. At 530, the optimized pathway may be provided to the patient. The optimized pathway may be provided based on a habit index associated with the patient to increase the probability that the patient follows the optimized pathway. In addition to providing the optimized pathway at 530 and/or after providing the optimized pathway at 530, the CGM monitor may continue CGM at 522 and the flowchart 540 may iteratively repeat itself by starting at 512 based on continuing CGM at 522. The flowchart 540 may occur at any applicable time period that is predetermined or that is dynamically determined for a given patient or a cohort of patients.

Figure 6B:
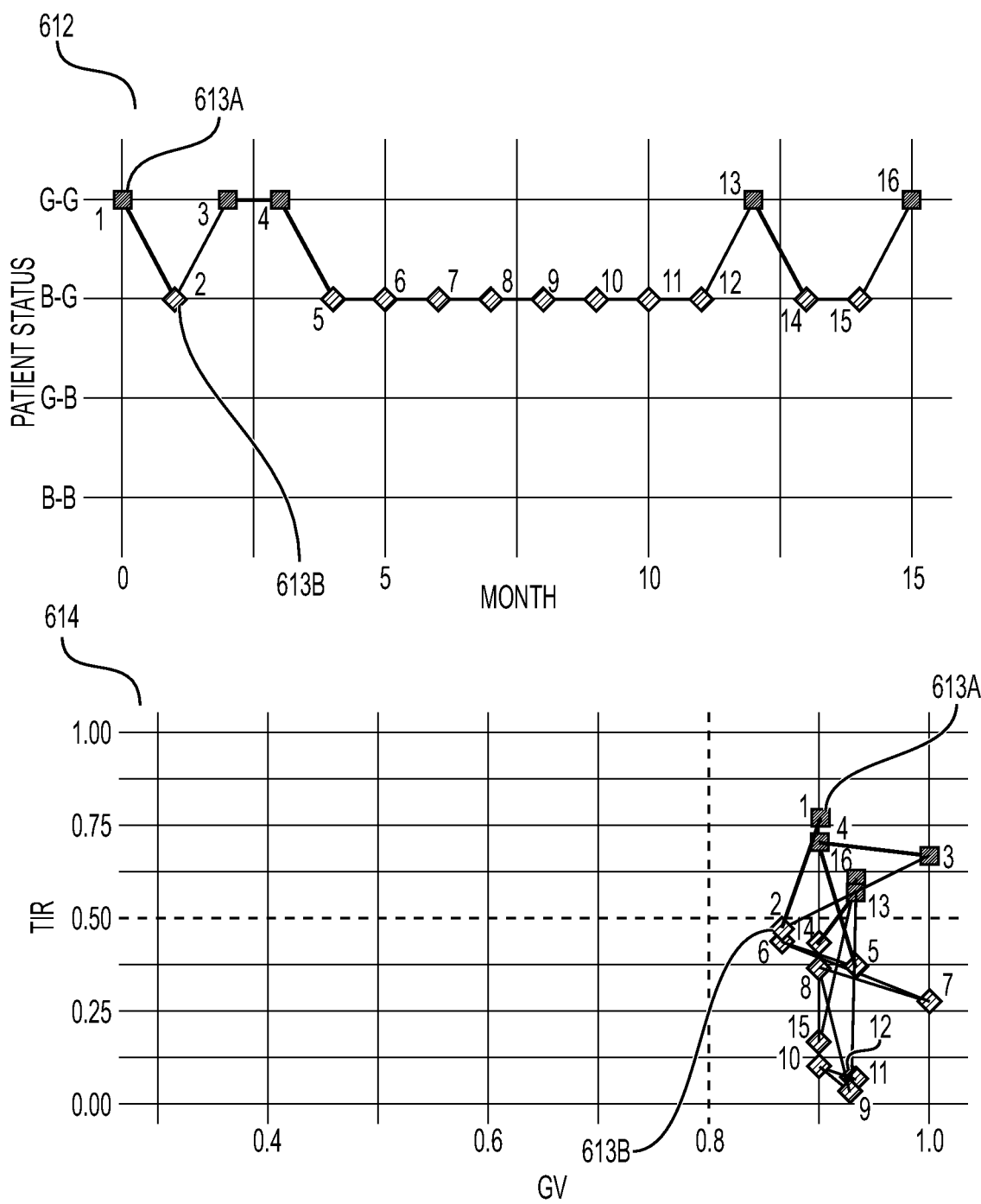
FIG. 6B is a patent state over time correlated to a patient state change graph, according to another example of the present disclosure.

FIG. 6B shows a chart 612 and chart 614. The first chart 612 shows multiple states for a given patient over the course of a number of months. For example, an initial state of the patient shown by 613A is a Good-Good state (i.e., Good TIR state and Good GV state) and the subsequent state after the initial state, shown by 613B, is a Bad-Good state (i.e., a Bad TIR state and a Good GV state). Chart 612 shows the various states for the patient over the course of the months. Each state (e.g., 613A, 613B, etc.) may be a representative state for that period of time. For example, the initial state shown by 613A may be the average of all states during the first month or may be the state for a given day such that the same day of the month is used for each of the months shown in chart 612. Chart 614 of FIG. 6B shows the same states as chart 612. However, chart 614 shows the two-dimensional state-based quadrants that enable a viewer to see the distribution of states as they relate to corresponding TIR states and GV states. Chart 612 and/or chart 614 may be provided to a user 8 or a healthcare provider 7 to enable a viewer to better understand the status of the user 8's state statuses.

Figure 6C:
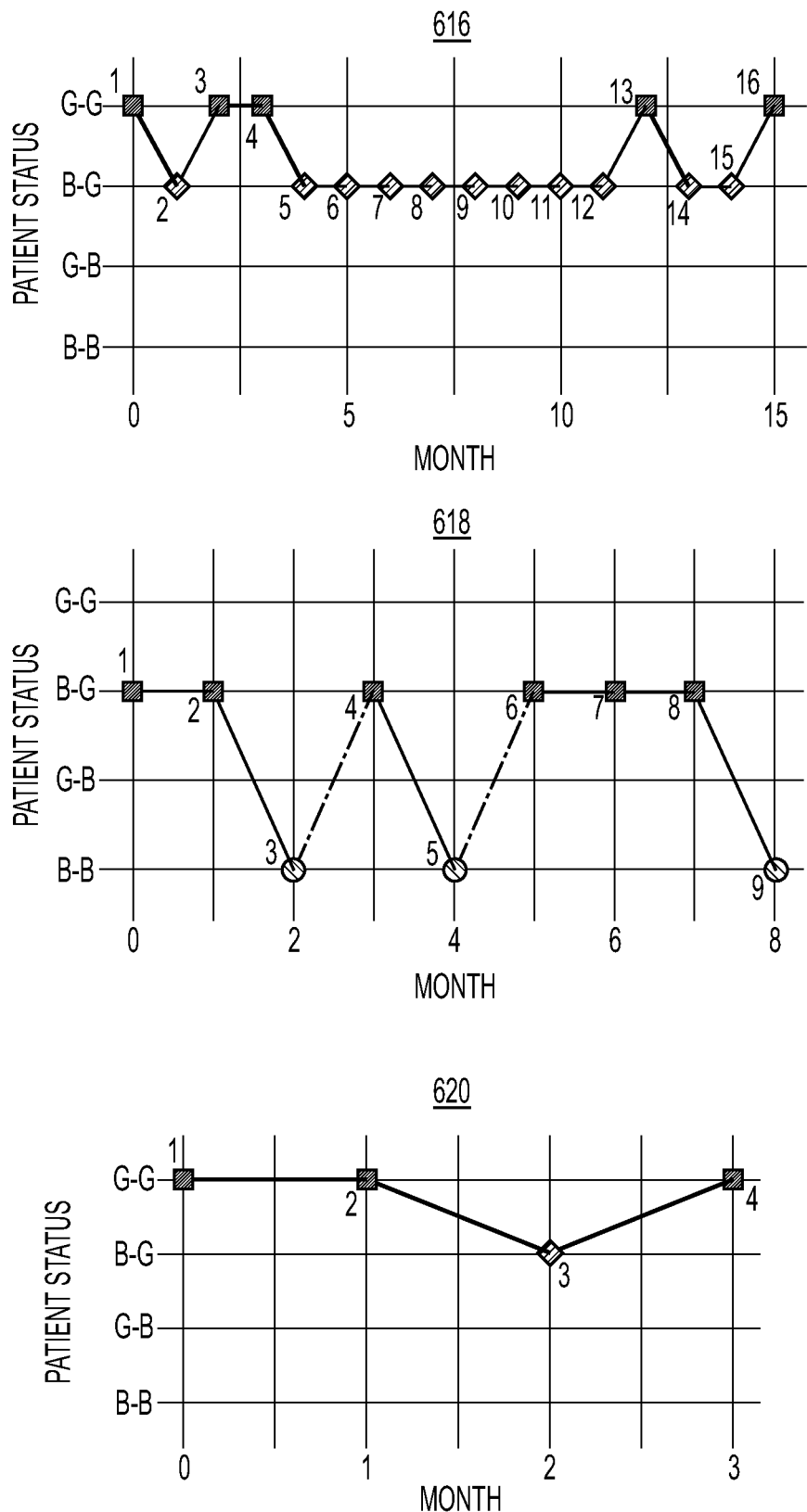
FIG. 6C shows three graphs of patient states over time, according to another example of the present disclosure.

FIG. 6C shows chart 616, 618, and 620, each with a varying amount of data. Chart 616 includes the most data with 15 months of CGM based state information. Chart 618 shows 8 months of CGM based state information, and chart 620 shows 3 months of CGM based state information. A greater number of data points may allow a viewer to understand a patient's glucose level based history more holistically then less data points.

Figure 6D:
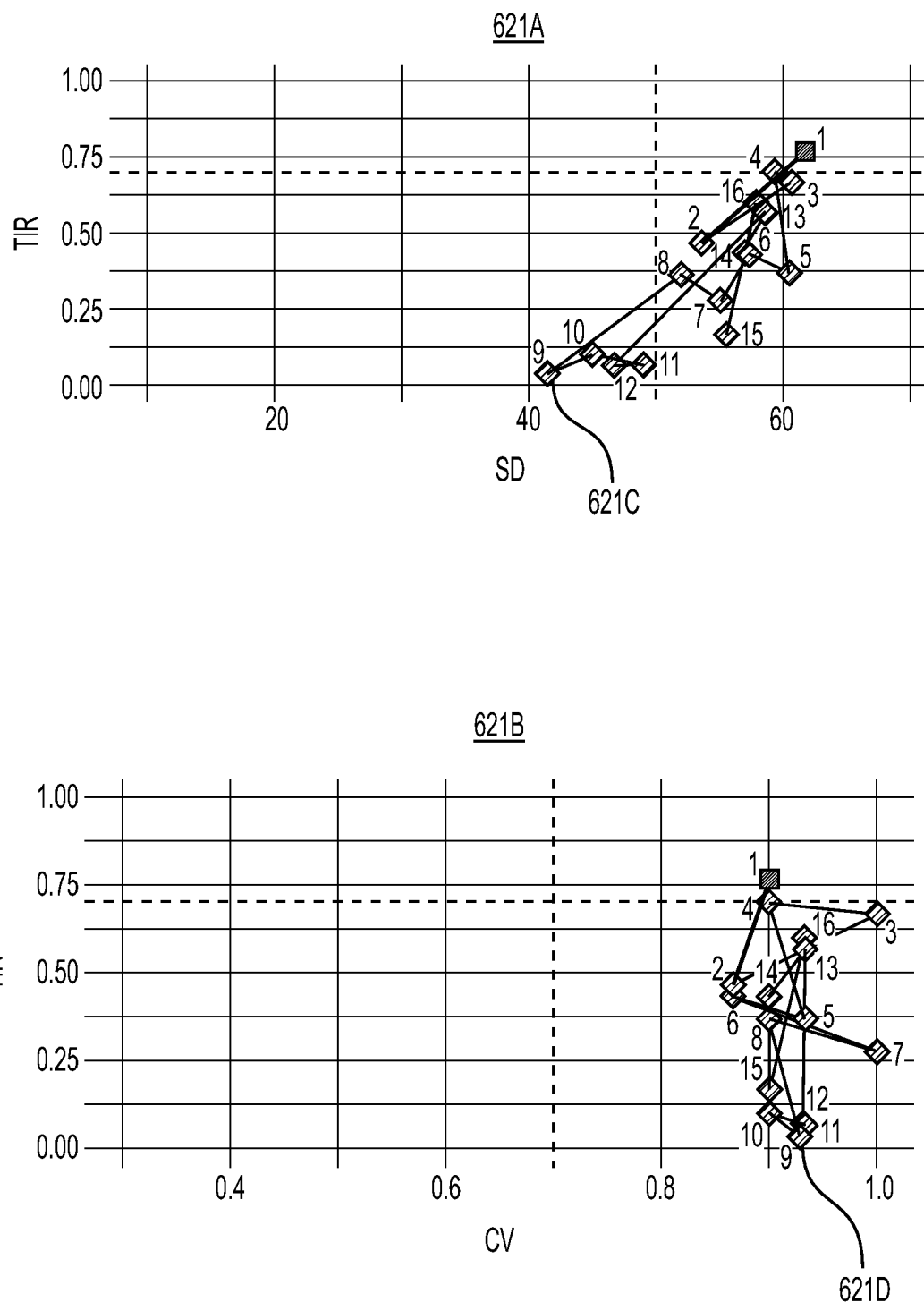
FIG. 6D shows a standard deviation graph and a coefficient of variance graph, according to another example of the present disclosure.

FIG. 6D shows chart 621A and 621B each showing GV values for a given patient over fifteen months. Chart 621A shows the standard deviation (SD) of the glucose level readings whereas chart 621B shows the coefficient of variance (CV) of the glucose level readings. As shown, the type of GV (e.g., SD, CV, etc.) applied may change GV state at a given time. For example, 621C of chart 621A shows a SD based GV value for the ninth reading. As shown, 621C corresponds to a Bad GV state. However, the same corresponding ninth reading's CV based GV value, represented by 621D in chart 621B corresponds to a Good GV state. The type of GV (e.g., SD, CV, etc.) to be applied may be selected based on one or more factors such as, but not limited to, patient vectors, historical glucose information, patient properties, or the like. It will be understood that the Respective Event numbers in FIGS. 6B-6D (i.e., Respective Events 1-16 in FIGS. 6B and 6D, Respective Events 1-16 in 616 of 6C, Respective Events 1-9 in 618 of 6C, and Respective Events 1-4 in 620 of FIG. 6C) are chronological indications relative to each other and not reference numbers.

Figure 6E:
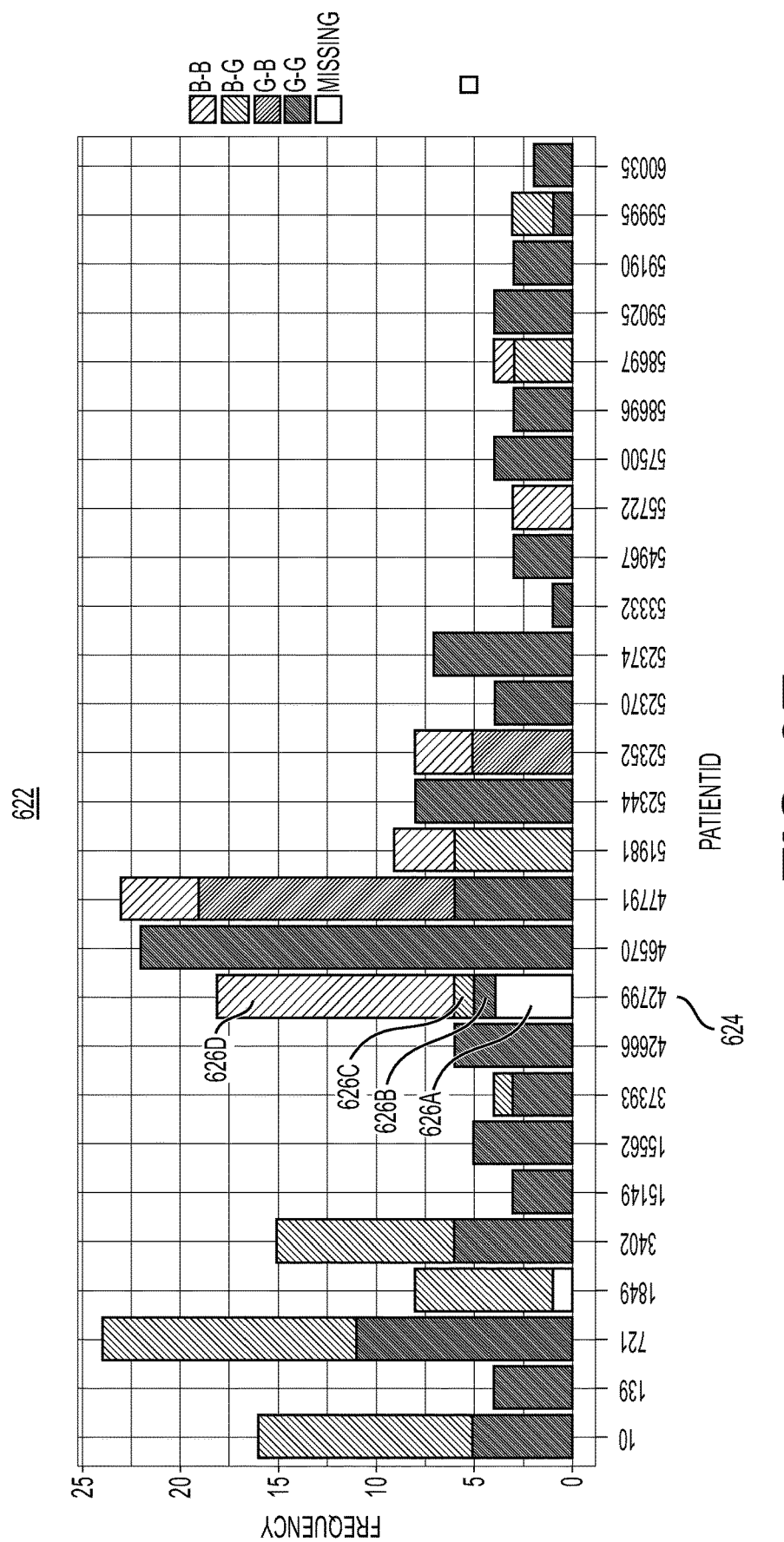
FIG. 6E shows state distributions for a plurality of patents, according to another example of the present disclosure.

FIG. 6E shows a chart 622 of the various states of each of a plurality of patients represented by anonymized patient IDs. For example, patient 624 (i.e., patient ID 42799) may have a number of missing states (e.g., due to missing CGM data) represented by bar 626A, a number of Good-Good (i.e., a Good TIR state and a Good GV state) states represented by bar 626B, a number of Bad-Good states represented by bar 626C, and a number of Bad-Bad states represented by bar 626D. A healthcare institution or a healthcare provider 7 monitoring a given cohort of patients may be provided chart 622 on a periodic basis. By reviewing visual changes in the states shown in chart 622, a viewer may be able to easily determine a trend of state changes for all or a subset of users implementing the techniques disclosed herein.

Figure 6F:
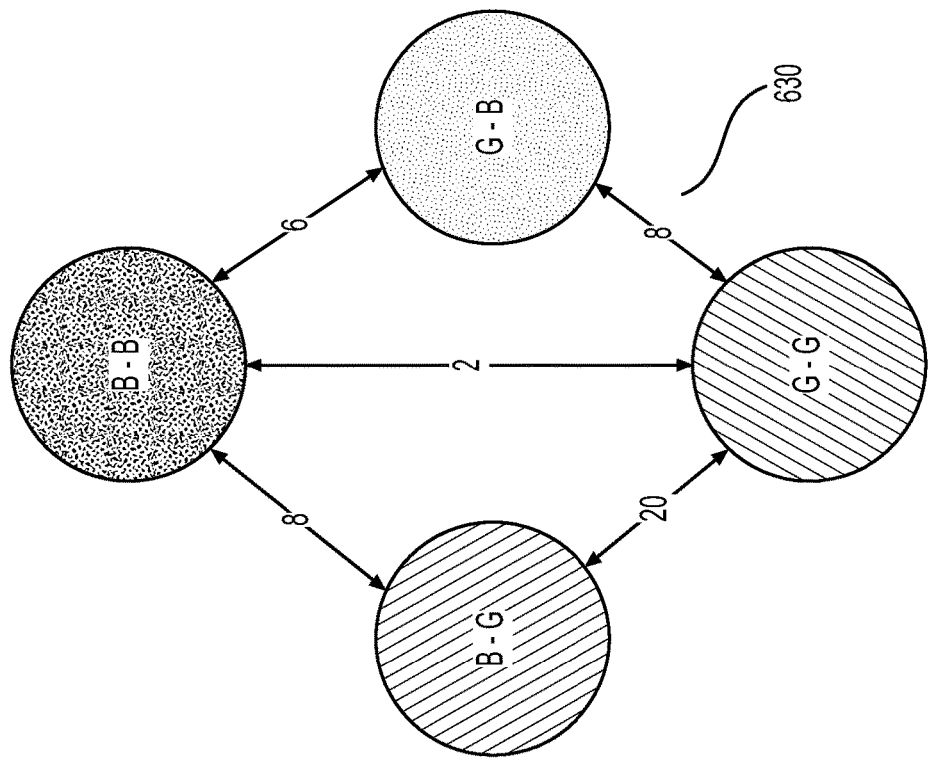
FIG. 6F shows changes in state distributions for a plurality of patents, according to another example of the present disclosure.

A healthcare institution or a healthcare provider 7 may also be provided chart 628 and/or diagram 630 of FIG. 6F. The healthcare institution or a healthcare provider 7 may use chart 628 to review the trends in change of statuses for a patient population. For example, a viewer provided chart 628 may be able to determine that there are more counts of patient statuses changing from Good-Good to Bad-Good (i.e., 11) then there are in the opposite direction (i.e., 9). Such data may be used to updated machine learning algorithms (e.g., to improve network layers, weights, etc. to provide improved optimized pathways), to improve how optimized pathways are provided/implemented (e.g., based on changes made to habit indexes, etc.), or the like.

Similarly, diagram 630 may be utilized by a healthcare institution or a healthcare provider 7 to review the trends in change of statuses for a patient population. By using diagram 630, a viewer may quickly see trends in status changes and may compare such trends over multiple periods of time. For example, a viewer provided with diagram 630 may easily compare the number of status changes that changed from Bad-Good to Good-Good (i.e., 20) and compare that to a previous month's changes. Although chart 628 and diagram 630 are shown with a number of status changes, it will be understood that the status changes may be represented in any applicable manner such as using a percentage of change.

Figure 6G:
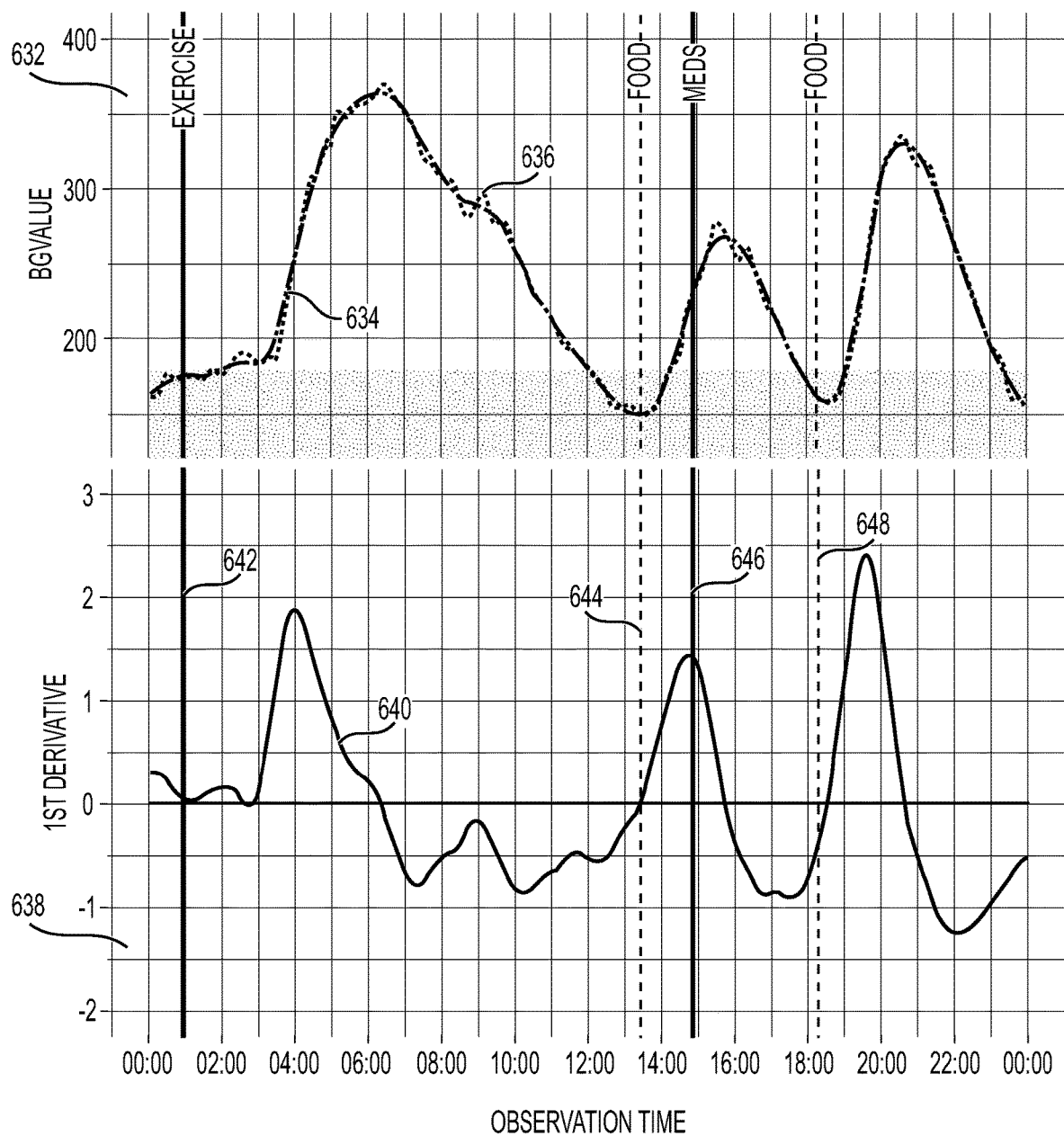
FIG. 6G shows glucose value changes over time and a corresponding first derivate graph, according to another example of the present disclosure.

As disclosed herein, the optimized pathway generated at 516 of FIG. 5A may be generated based on one or more patient vectors. FIG. 6G shows chart 632 of a patient's glucose level readings 634 (e.g., as collected using a CGM monitor) over the course of a day. A filter or other smoothing mechanism may be used to generate the corresponding trend line 636. Chart 638 shows a first derivative 640 of the chart which represents the rate of change of the glucose level readings 634 or the smoothed trend line 636 of chart 632. Both charts 632 and 638 include patient vectors including an exercise vector 642, a food vector 644, a medication vector 646, and another food vector 648 such that a machine learning model may receive such vectors and their associated attributes (e.g., time of each given vector, properties of the vector such as duration of exercise, type of food, medication type and/or dosage, etc.). A patient's glucose level readings 634 may be used as inputs to the machine learning model along with the first derivative 640 of the patient's glucose level readings 634 or either the a patient's glucose level readings 634 or the first derivative 640 may be used individually. Accordingly, an output optimized pathway provided by the machine learning model may be based on a patient's glucose level readings 634, patient vectors (e.g., exercise vector 642, a food vector 644, a medication vector 646, and another food vector 648), and/or the first derivative 640.

Figure 7B:
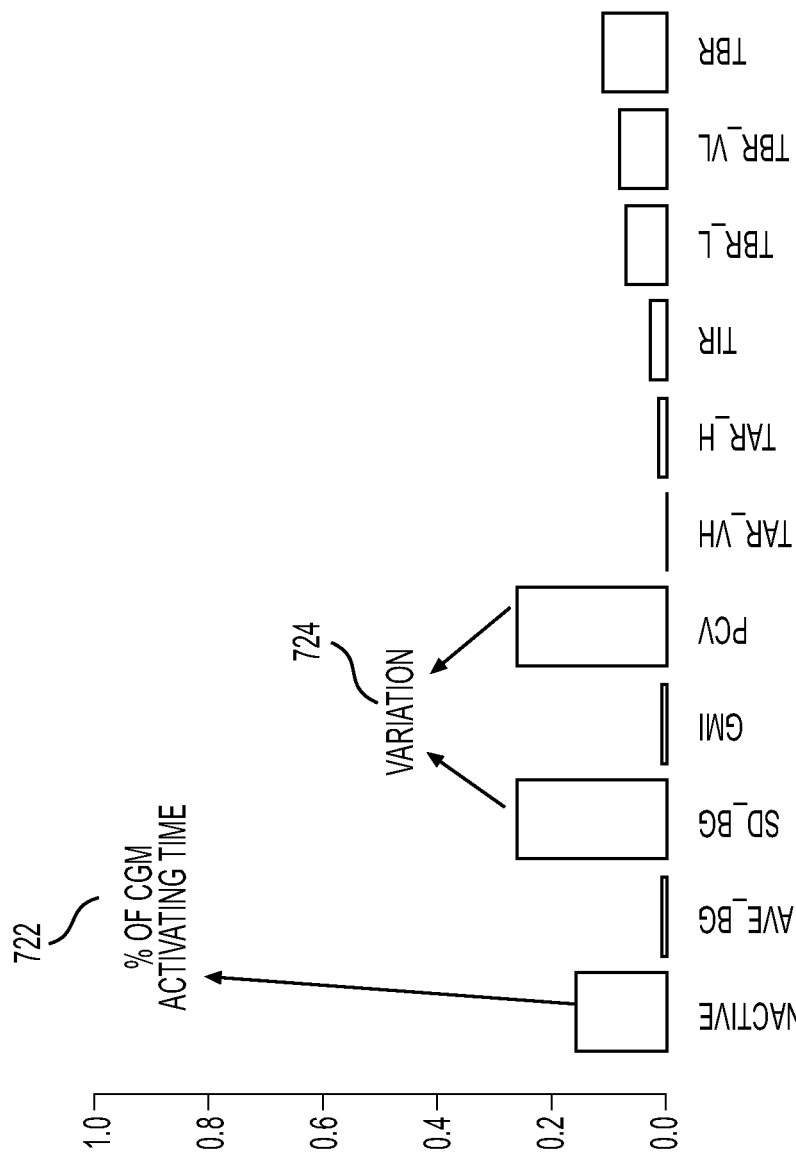
FIG. 7B shows a continuous glucose monitoring activating time and variation chart, according to another example of the present disclosure.

As shown in FIG. 4B, an AGP report and may include a number of metrics (e.g., 10 metrics) as well as graphical data. These metric may be are numerous and difficult to understand, both for patients and healthcare providers 7. Techniques disclosed herein are, in part, based on minimizing the number of metrics as components of one metric of the AGP report are determined by other measures such that not all 10 measures are necessary since they don't give unique and independent information. FIG. 7A and FIG. 7B show that techniques disclosed herein may be implemented using the mean glucose 704, Time Above Range (TAR) and TIR 706, the variation in glucose 710, the time below range (TBR), the percent of CGM activating time 722, and/or the variation in the standard deviation and principal component value (PCV) of glucose 724. The mean glucose 704 may be based on the average glucose and a Glucose Management Indicator (GMI), where the GMI is a predicted indication of a glucose level. The TAR and TIR 706 may be based on a very high TAR indication (TAR_VH), a high TAR indication (TAR_H), and/or a TIR indication. The variation in glucose 710 may be based on the standard deviation of glucose and the PCV. The TBR 712 may be based on the low TBR (TBR_L), very low TBR (TBR_VL), and TBR indications.

Figure 8A:
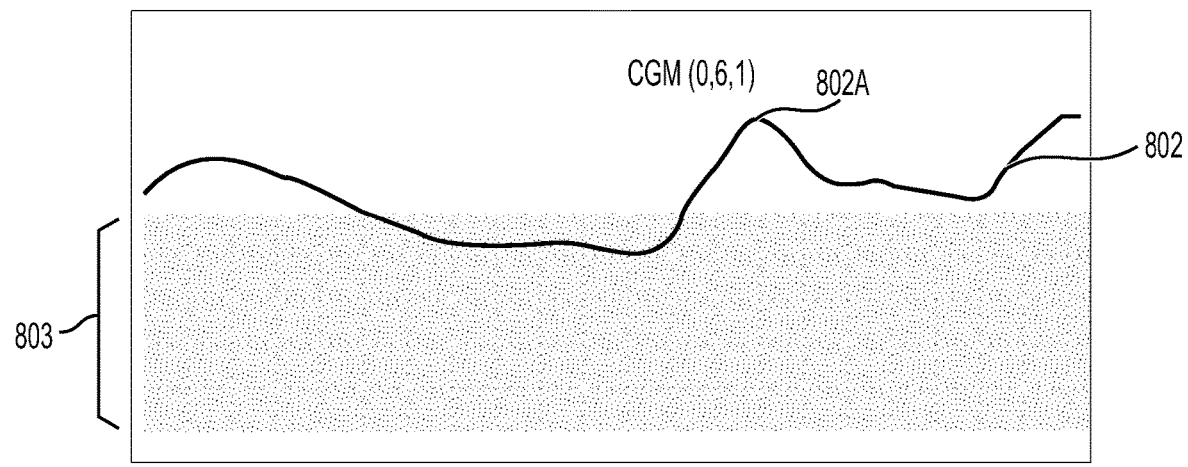
FIG. 8A shows a continuous glucose monitoring chart, according to another example of the present disclosure.
Figure 8B:
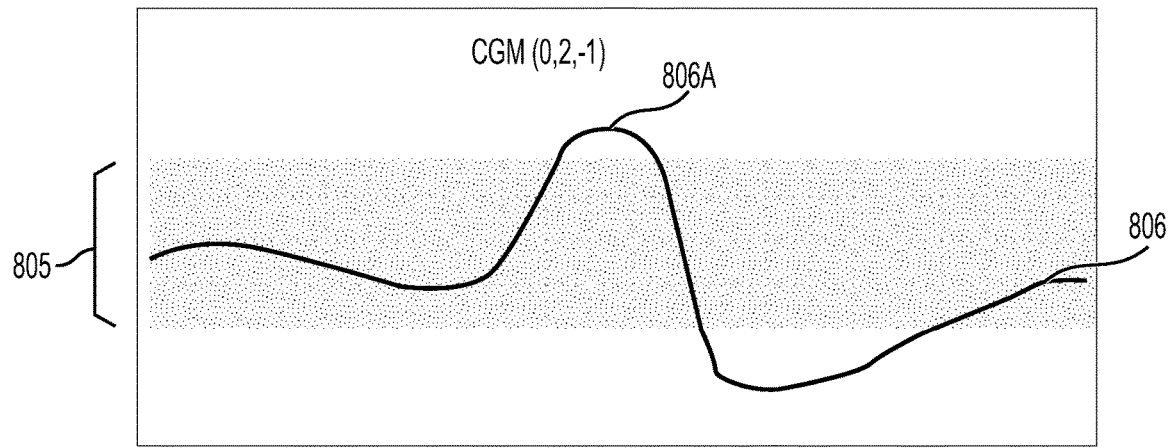
FIG. 8B shows another continuous glucose monitoring chart, according to another example of the present disclosure.
Figures 8C, 8D:
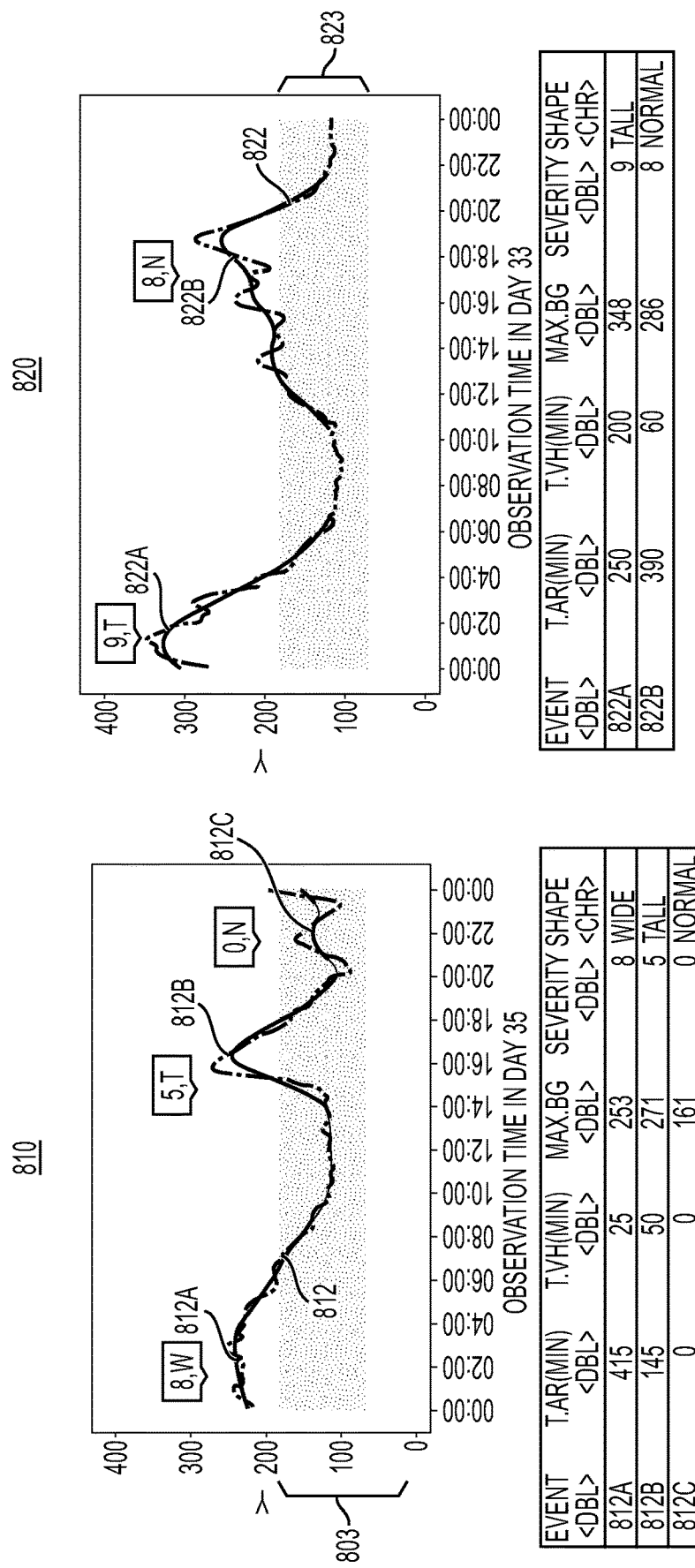
FIG. 8C shows another continuous glucose monitoring chart, according to another example of the present disclosure.
FIG. 8D shows another continuous glucose monitoring chart, according to another example of the present disclosure.

According to an implementation of the disclosed subject matter, one or more CGM events may be classified based on the patient's glucose levels. The classifying may be based at least on a severity score associated with each of the one or more CGM events and/or based on one more properties of a curve associated with the glucose levels of a patient. FIGS. 8A, 8B, and 8C show example classifications of CGM events. The optimized pathway generated at 516 of FIG. 5A may be based, in part, based on the one or more classified CGM events. For example, the severity or other property of a CGM event may be provided to a machine learning model and the optimized pathway may be output based, at least in part, on the one or more classified CGM events. As a an example, the severity score may indicate the presence of sharp peaks or the frequency of a high severity score may indicate a high amount of volatility in a patient's glucose levels. Such CGM based event information may be helpful especially if, for example, the patient has a high TIR as the TIR would not indicate an unhealthy amount of fluctuation in the patient's glucose levels.

Applying CGM events to determine an optimized pathway may include detection of events from a CGM trace (e.g., a series of glucose value readings), and classifying the events into one or more classes. The classification may include severity score based classifications and/or glucose categories. Severity scores may be determined using the time and shape characteristics of a CGM trace.

The severity score and/or CGM events may be determined for individual fluctuations in CGM data and may be part of a micro view of the CGM. The severity score and/or CGM events may be used for real-time coaching or behavior outputs (e.g., in the moment coaching regarding medications, diet, exercise, etc.). Accordingly, techniques disclosed herein provide both a macro view of the CGM data (e.g., using state data as described in FIG. 5A) and a micro view of the CGM data (e.g., using the severity scores and/or CGM events) to provide both real-time and overall health improvement feedback.

FIG. 8A shows a chart 800 with a CGM trace 802 including a CGM event 802A. FIG. 8B shows a chart 804 with a CGM trace 806 including a CGM event 806A. The CGM event 802A may be detected based on one or more mathematical methods. In the example provided in FIG. 8A, the CGM event 802A may be classified based on the clinical significance multi-parameter CGM classification such as three parameters: glucose at the beginning, severity, glucose at the end (b, s, d).

The parameter b may correspond to the glucose category at or near the beginning of a given CGM event. The glucose category b may be a scale such as a very high (e.g., +2), high (e.g., +1), in range (e.g., 0), low (e.g., −1), or very low (e.g., −2). In the example of CGM event 802A, b corresponds to 0 as the glucose level indicated by trace 802 is within the threshold range 803 at the beginning of the CGM event 802A, as shown via the trace 802 being within the threshold range indicated by 803 at the start of the CGM trace 802 when the trace 802 curves up towards the peak of the CGM event 802A. In the example of CGM event 806A of FIG. 8B, b corresponds to 0 as the glucose level indicated by trace 806 is within the threshold range 805 at the beginning of the CGM event 806A, as shown via the trace 806 being within the threshold range 805 at the start of the CGM event 806A when the trace 806 curves up towards the peak of the CGM event 806A.

The parameters may correspond to a severity score that encompasses both the height of the curve of a CGM event and how long the curve stays above target. The severity score s may be expressed as a value (e.g., 0 through 9) that indicates the height of the curve of a CGM event and the duration that the curve stays above target. The severity score may be calculated via any applicable technique that provides a severity score based on the combination of the height of a CGM curve and the duration of the corresponding trace being outside threshold range. As a simplified example, a value associated with the height of the curve may be multiplied by a value associated with the duration of the trace being outside a threshold range. One or both of the height and duration values may be greater than one. According to an implementation, the height and the duration may be allocated different weights such that severity score is based more heavily on one of the height or the duration. A higher severity score may indicate a higher combination of the height and duration above target. A lower severity score may indicate a lower combination of the height and duration above target. Accordingly, a lower severity score may be more desirable than a higher severity score.

In the example of CGM event 802A, the parameters corresponds to a severity score of 6 determined based on the height of the curve associated with CGM event 802A and the duration that the trace 802 is outside the threshold range 803. In the example of CGM event 806A, the parameter s corresponds to a severity score of 2 determined based on the height of the curve associated with CGM event 806A and the duration that the trace 806 is outside the threshold range 805. The height of the curve and the duration of time outside a target threshold range for the CGM event 802A is greater than the height of the curve and the duration of time outside a target threshold range for the CGM event 806A, as shown in FIGS. 8A and 8B. Accordingly, the severity score for CGM event 802A is higher (i.e., 6) when compared to the CGM event 806A (i.e., 2).

The parameter e may correspond to the glucose category at or near the end of a given CGM event. The glucose category b may be a scale such as a very high (e.g., +2), high (e.g., +1), in range (e.g., 0), low (e.g., −1), or very low (e.g., −2). In the example of CGM event 802A, e corresponds to 1 as the glucose level indicated by trace 802 is higher than the range 803 at the end of the CGM event 802A, as shown via the trace 802 being approximately outside the threshold range indicated by 803 at the end of the CGM trace 802 when the trace 802 flattens out after the peak of the CGM event 802A. In the example of CGM event 806A of FIG. 8B, e corresponds to −1 as the glucose level indicated by trace 806 is below the threshold range 805 at the end of the CGM event 806A, as shown via the trace 806 being within the threshold range 805 at the end of the CGM event 806A when the trace 806 flattens and changes direction below the threshold range 805.

According to another implementation, CGM events may be characterized using one more other techniques. For example, CGM events may be characterized based on a severity score and shape of the CGM event. FIGS. 8C and 8D show example CGM events characterized by a severity score and CGM event trace shape. The severity score may be calculated based on the height of a CGM trace and the duration of the trace being outside a threshold glucose range, as disclosed herein. The shape of a CGM event may be categorized in any applicable manner such as, for example, a wide category, a tall category, and a normal category. Such categories may be based on the start, peak, and ending of a given CGM event and the parameters associated with classifying a CGM trace as a given category may be pre-determined or may be determined based on a given patient, a plurality of CGM traces, or the like. For example, a ratio of the area outlined by a given CGM trace and the height of the trace may be used to classify a CGM trace.

FIG. 8C shows a chart 810 with a CGM trace 812, threshold range 803, and three CGM events 812A, 812B, and 812C. The first CGM event 812A has a severity score of 8 and a CGM trace shape that is characterized as Wide. The second CGM event 8128 has a severity score of 5 and a CGM trace shape that is characterized as Tall. The third CGM event 812C has a severity score of 0 and a CGM trace shape that is characterized as Normal. The severity score of the third CGM event 812C is 0 as the trace 812 at the peak of the CGM event 812C is within a threshold range 813.

According to implementations, a CGM trace shape may also be characterized as short. Additionally, a machine learning model may be used to identify a CGM trace shape based on, for example, past CGM trace shapes. The machine learning model may be updated based on updated CGM traces. For example, updated glucose values may be calculated by a CGM monitor after an optimized pathway is provided based on a severity score, a CGM trace shape, or the like. The updated glucose values may encompass the effect that the optimized pathway has on the user. The updated glucose values may be used to generate an updated CGM trace that is provide to the machine learning model to update the model. For example, if the optimized pathway did not improve a user's condition, the machine learning model may be updated to improve its output during a subsequent or future iteration.

FIG. 8D shows a chart 820 with a CGM trace 822, threshold range 823, and two CGM events 822A and 822B.

The first CGM event 822A has a severity score of 9 and a CGM trace shape that is characterized as Tall. The second CGM event 822B has a severity score of 8 and a CGM trace shape that is characterized as Normal.

One or more clinically significant CGM events for a given user 8 may be categorized using CGM categorization (e.g., b, s, e of FIGS. 8A and 8B, or the severity score and shape characterization of FIGS. 8C and 8D, or any other applicable characterization). An optimized pathway (e.g., via automated coaching messages, DSMA, etc.) may then be sent to a user 8 further based on the CGM event characterization.

FIG. 9 includes a flowchart 900 for an implementation of the disclosed subject matter. At 902, a plurality of optimization profiles for reaching an ideal state from a non-ideal state may be generated. The plurality of optimization profiles may not be patient specific but may be each be generated for combinations of a plurality of patient vectors and patient attributes. The plurality of optimization profiles may be generated using a machine learning model trained as provided in FIG. 5B as disclosed herein. The plurality of optimization profiles may be provided as outputs to the machine learning model and may be based on a cohort of past patients and may further be based on successful or unsuccessful attempts to reach an ideal state from a non-ideal state.

The plurality of optimization profiles may be each be associated with one or more patient attributes and/or patient vectors. For example, for a given set of patient vectors and patient attributes, a specific optimization profile may be generated for each possible non-ideal state (e.g., Good-Bad, Bad-Bad, Bad-Good, etc.).

At 904, a TIR state for a given patient may be determined and at 906, a GV state for a given patient may be determined, in accordance with techniques disclosed herein. At 908, one or more patient vectors and one or more patient attributes for the given patient may be received. The patient vectors and/or patient attributes may be provided by the given patient, by a healthcare provider 7, obtained via electronic device 19, via servers 29, or any other applicable means.

At 910, an optimization profile based on the patient vectors and the patient attributes may be identified. Optimization profile may include a limited number of optimized pathways, where each optimized pathway may correspond to a given combination of TIR states and GV states. For example, an optimization profile may include an optimized pathway for a Good-Bad starting state, a Bad-Bad starting state, and a Bad-Good starting state. Accordingly, a given optimization profile may be identified based on a patient's attributes and vectors, and may include a limited number of optimization profiles based on the patient's starting states.

At 912, an optimized pathway may be identified from the optimization profile and based on the given patient's TIR state and GV state. The optimized pathway may be different at different for the same patient even if all of the patient's vectors and attributes remain the same. For example, during a first iteration, a given patient's optimization profile may be identified based on the patient's attributes and vectors at the time of the first iteration. Based on the patient's TIR state and GV state during the first iteration (e.g., a Good-Bad state), a first optimized pathway may be identified. However, during a second iteration, even if the given' patient's vectors are the same (i.e., such that the same optimization profile is identified), a different optimized pathway may be identified based on a change in state (e.g., a Bad-Good state). At 914, the identified optimized pathway may be provided to the given patient and/or healthcare provider 7, in accordance with the techniques disclosed herein.

While steps 502-518 of FIG. 5A, 512-530 of FIG. 5B, and 902-914 of FIG. 9 are depicted in a particular order, the principles of the present disclosure are not limited to the orders depicted therein.

Figure 10A:
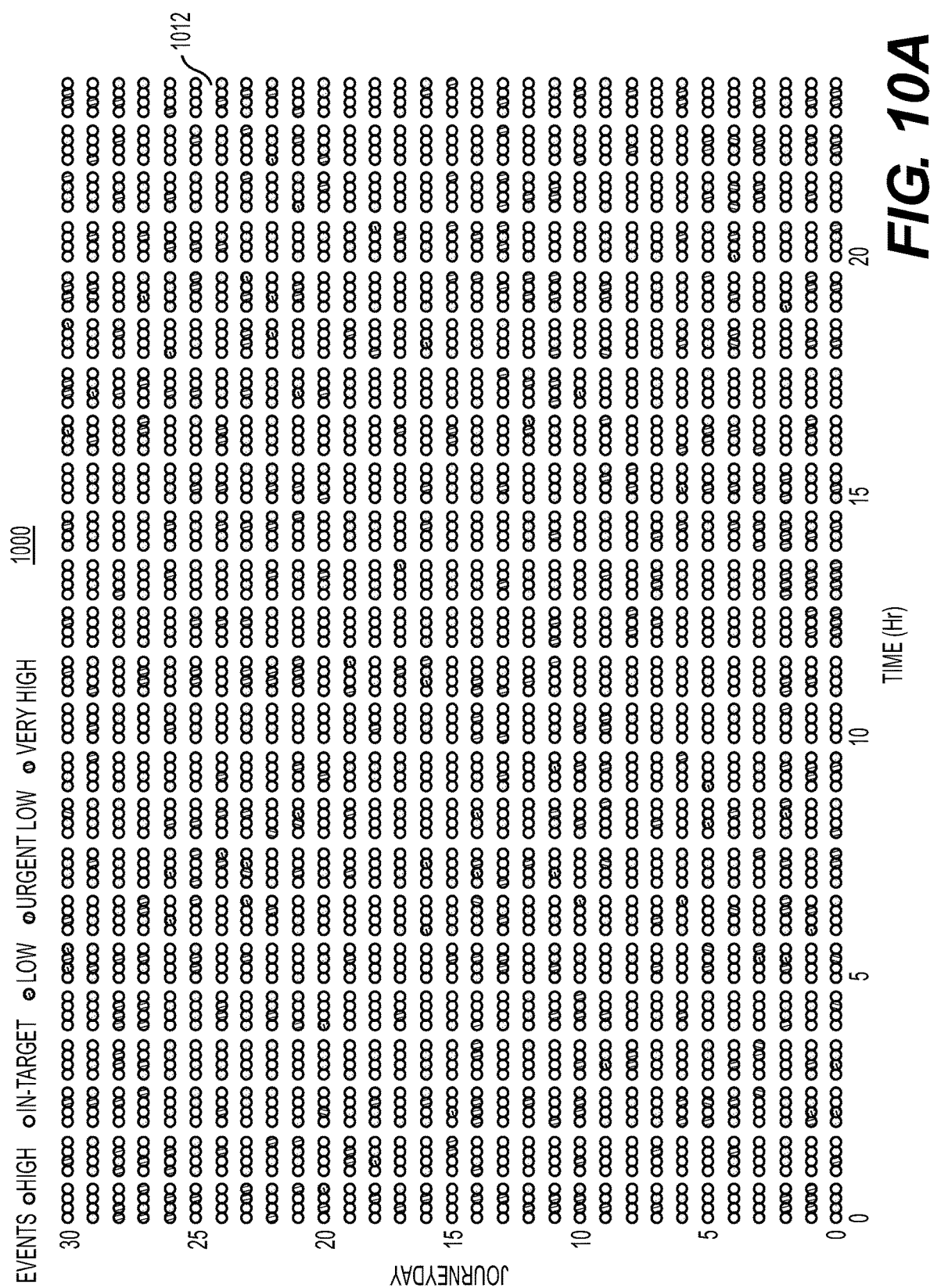
FIG. 10A is a continuous glucose monitoring event visualization, according to an example of the present disclosure.

FIG. 10A shows a diagram 1000 that includes a chart 1002 of CGM events by time and day. Such a diagram or other visual output may be provided to a healthcare provider 7 or a user 8 via an application (e.g., mHealth application 1) to more easily understand their CGM journey for a given time period. Diagram 1000 includes a number of Journey days as the Y access and a time of day as the X axis. A viewer may receive diagram 1000 and easily determine patterns on given days, times of days, and/or over a number of days or times.

Figure 10B:
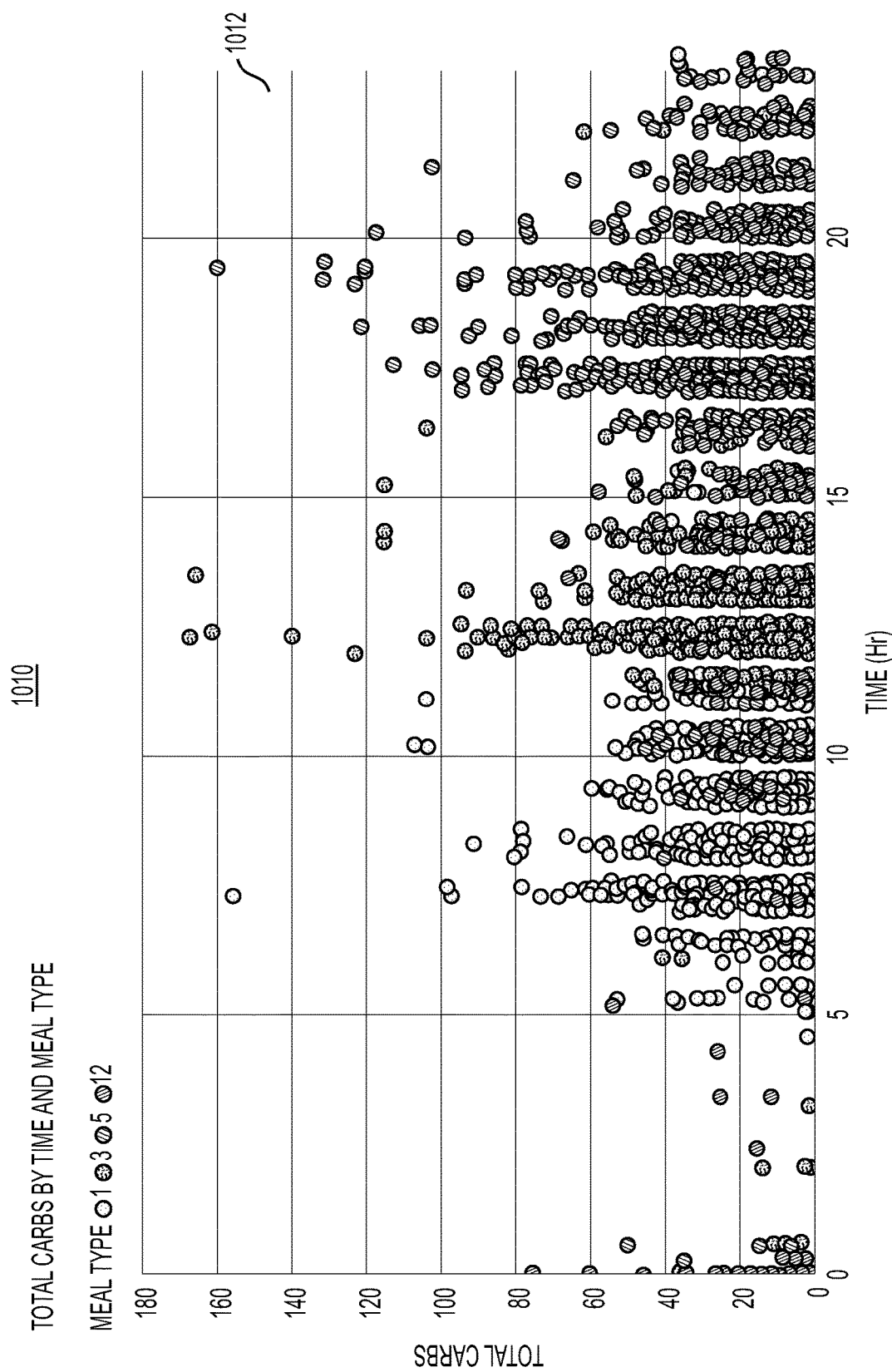
FIG. 10B is diet monitoring event visualization, according to an example of the present disclosure.

FIG. 10B shows a diagram 1010 that includes a chart 1012 of total carbs consumed by time and meal type. Such a diagram or other visual output may be provided to a healthcare provider 7 or a user 8 via an application (e.g., mHealth application 1) to more easily understand their dietary habits for a given time period. Diagram 1010 includes a number of total carbs as the Y access and a time of day as the X axis. A viewer may receive diagram 1010 and easily determine patterns on given days, times of days, and/or over a number of days or times. For example, the user may easily see the meal types consumed over the course of a day and the calories associated with the meal type.

Figure 11:
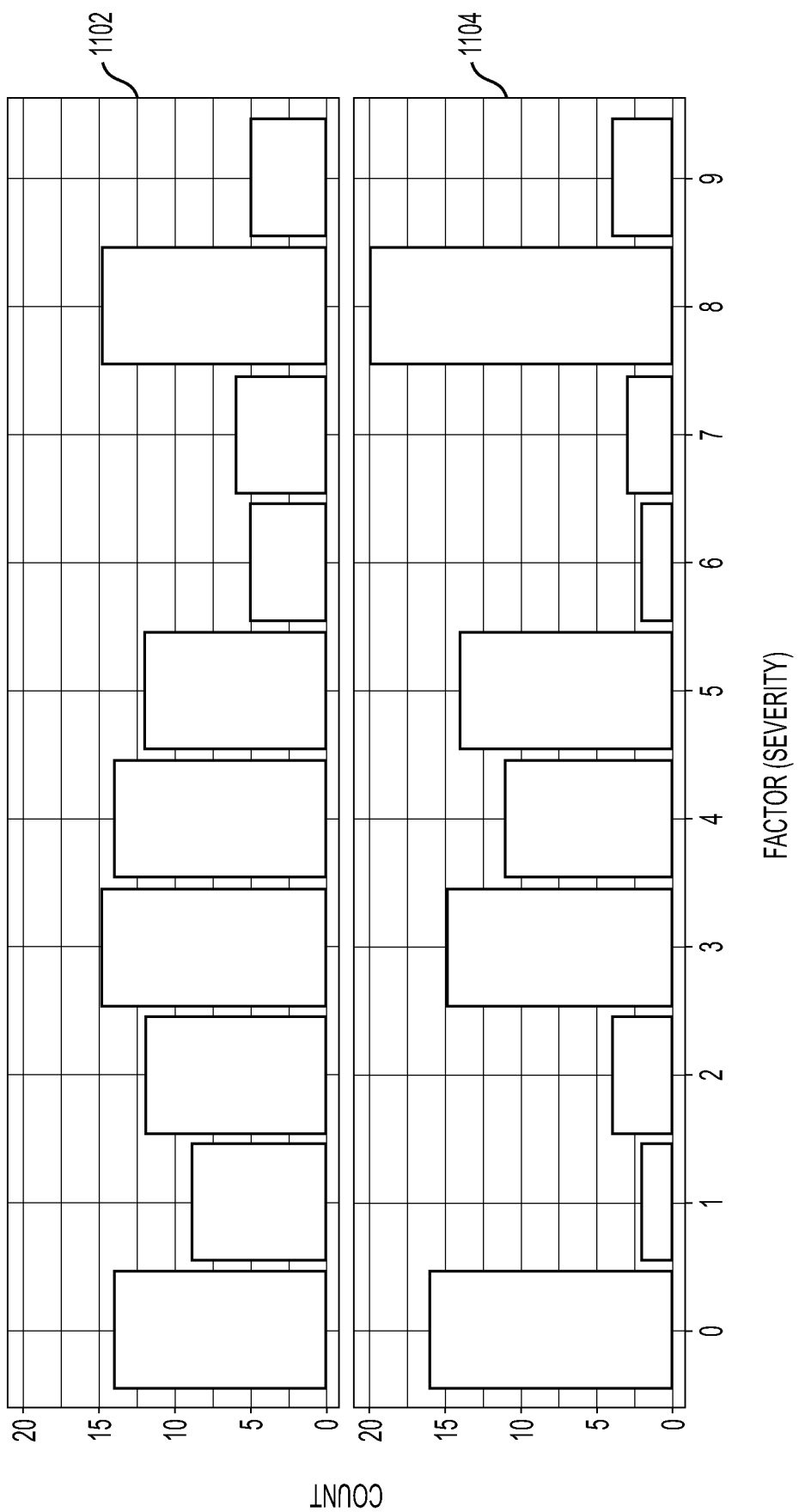
FIG. 11 is severity count visualization, according to an example of the present disclosure.

FIG. 11 shows a count of severity scores for a first patient, as shown via chart 1102 and a second patient, as shown via chart 1104. Each bar in the chart 1102 and chart 1104 represents the number of times a given severity score was exhibited in the respective first and second patient's CGM data. Generally, a higher count for a lower severity score may be preferable as such a distribution may indicate better diabetes management. A healthcare institution or healthcare provider 7 may receive distribution charts (e.g., chart 1102 and chart 1104) for one or multiple patients over one or more time periods and may use the distribution charts to monitor overall patient group progress. Alternatively, or in addition, distribution charts may be generated for a specific patient group (e.g., based on time of treatment, based on healthcare team, patient attributes, patient vectors, etc.) and may analyze trends for the specific patient groups or compare trends between multiple patient groups.

Figure 12:
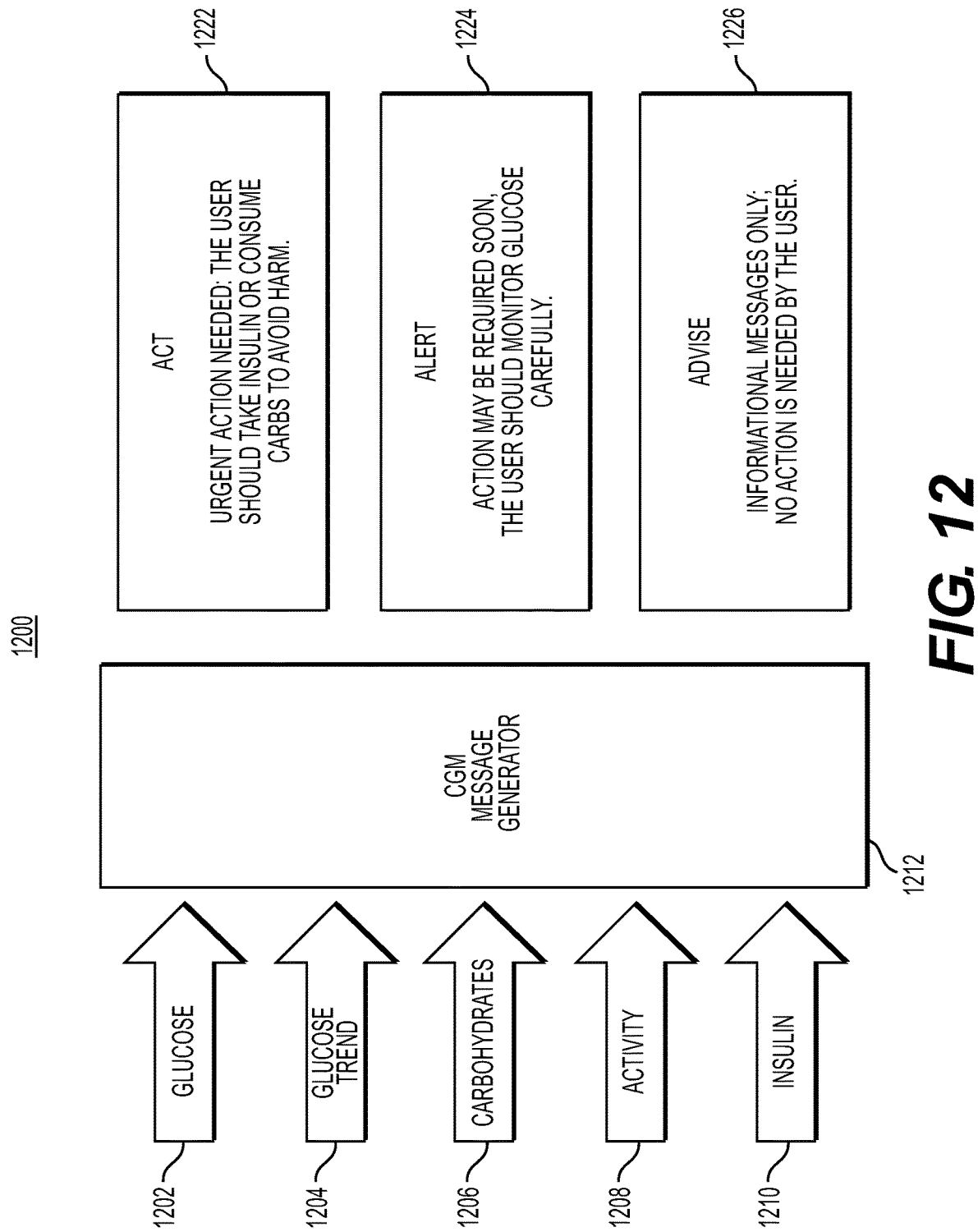
FIG. 12 is an automated alert generation chart, according to an example of the present disclosure.

FIG. 12 shows a diagram 1200 of a CGM based implementation for providing coaching to a patient based on CGM data. As shown, one or more attributes may be provided to a CGM message generator 1212. The attributes may include, but are not limited to, glucose values 1202, glucose trends 1204 (e.g., CGM trends, CGM event data, etc.), carbohydrate information 1206, activity information 1208, insulin information 1210, and the like or a combination thereof. Based on the attributes, a message level may be determined. For example, the message level may be an Act level 1222 where urgent action is needed (e.g., a user should take insulin or consume carbohydrates to avoid harm), an Alert level 1224 where action may be required soon, but is not urgent (e.g., a user should monitor glucose carefully), or an Advise level 1226 where an information message is provided (e.g., no action needed by the user).

The CGM message generator 1212 may be applied at 518 of FIG. 5A or 914 of FIG. 9 as the CGM message generator 1212 may be used to provide an optimized pathway based on a patient vector (e.g., the attributes 1202-1210). For example, an optimized pathway may be determined based at least in part on the attributes 1202-1210 and may be provided to a corresponding patient via the CGM message generator 1212.

Figure 13A:
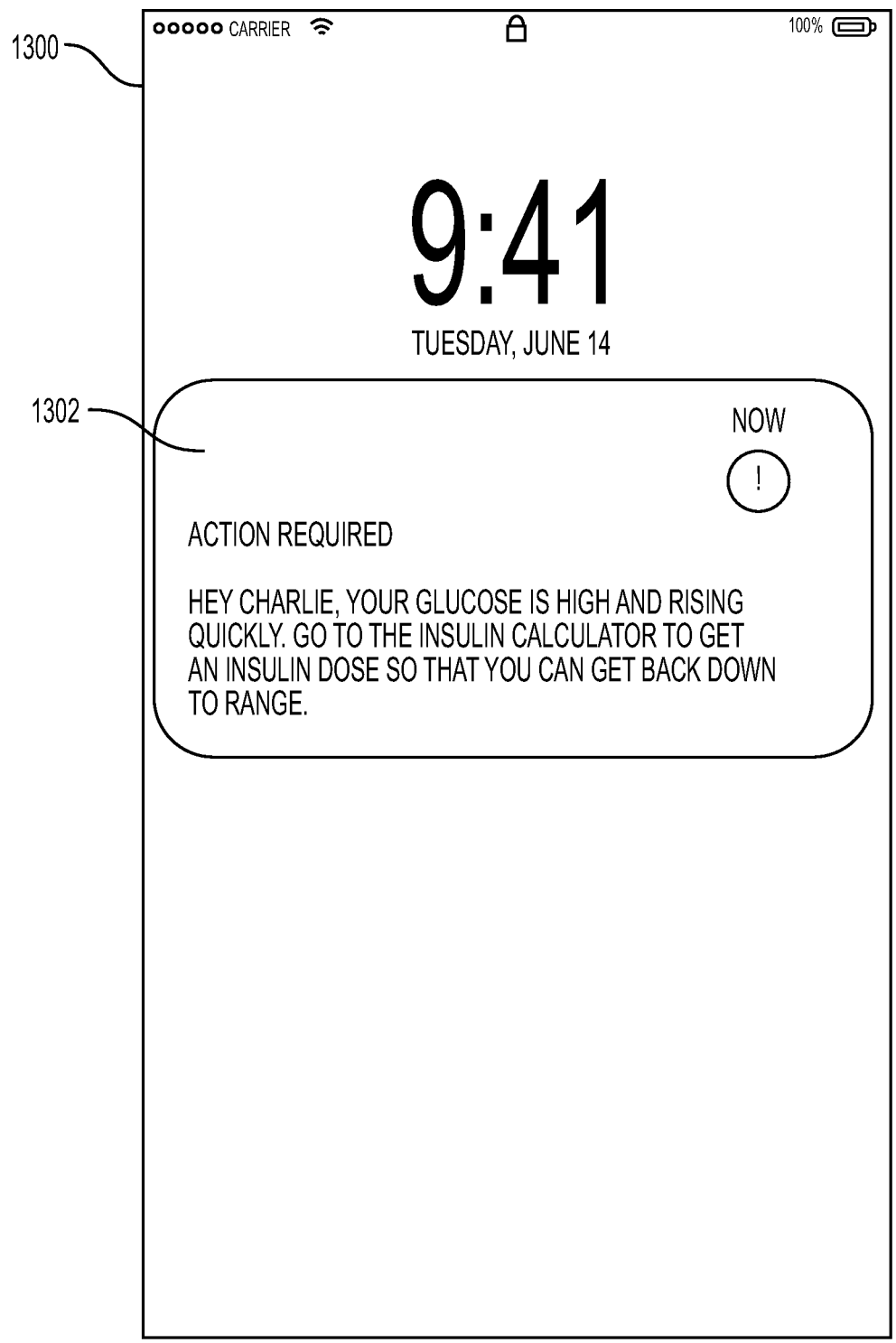
FIG. 13A is a screenshot of an exemplary message, in accordance with an example of the present disclosure.

FIG. 13A shows an example message 1302 provided using the CGM message generator 1212. The message 1302 may be provided via a user 8's electronic device 19. In the example provided in FIG. 13A, the message is an Act level 1222 message and may include a required action. As shown, the example message 1302 is, "Action Required: Hey Charlie, your glucose is high and rising quickly. Go to the insulin computer go get an insulin dose so that you can get back down to range." The message 1302 may be provided to the user 8 via mobile phone 1300 such that it is sent with high importance. The high importance may result in the electronic device 19 providing an audible alert, a haptic alert, visual alert, or the like, in addition to the message 1302.

Figure 13B:
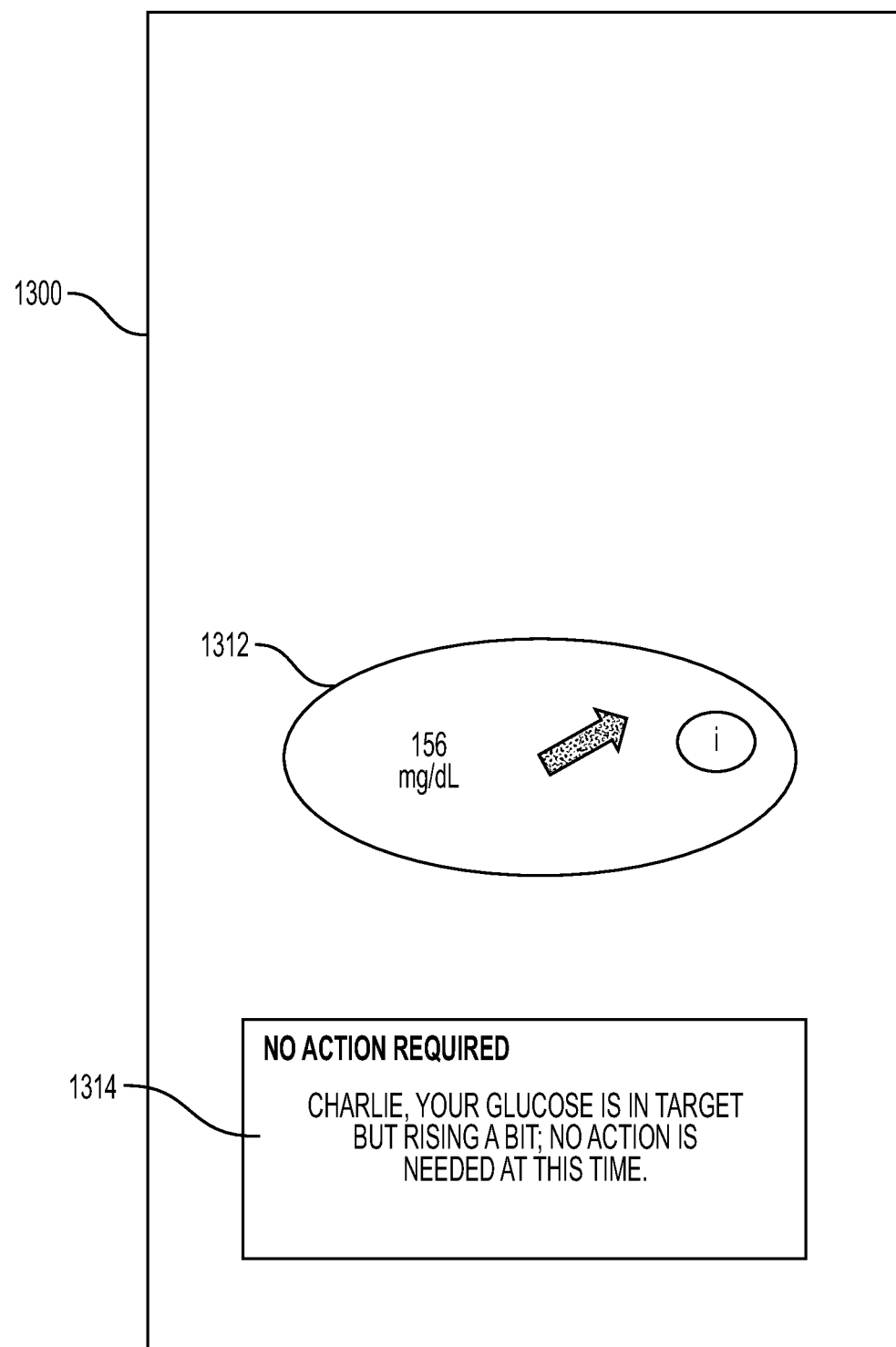
FIG. 13B is another screenshot of an exemplary message, in accordance with an example of the present disclosure.

FIG. 13B shows another example message 1314 provided using the CGM message generator 1212 via the mobile phone 1300. Message 1314 is an Alert level 1224 message and may not include an immediate action. As shown, the example message 1314 is, "No Action Required: Charlie, your glucose is in target but rising a bit; no action is required at this time." Additionally, additional information such as glucose level 1312 may also be provided via mobile phone 1300 and may be provided in proximity to the related message 1314.

Figure 13C:
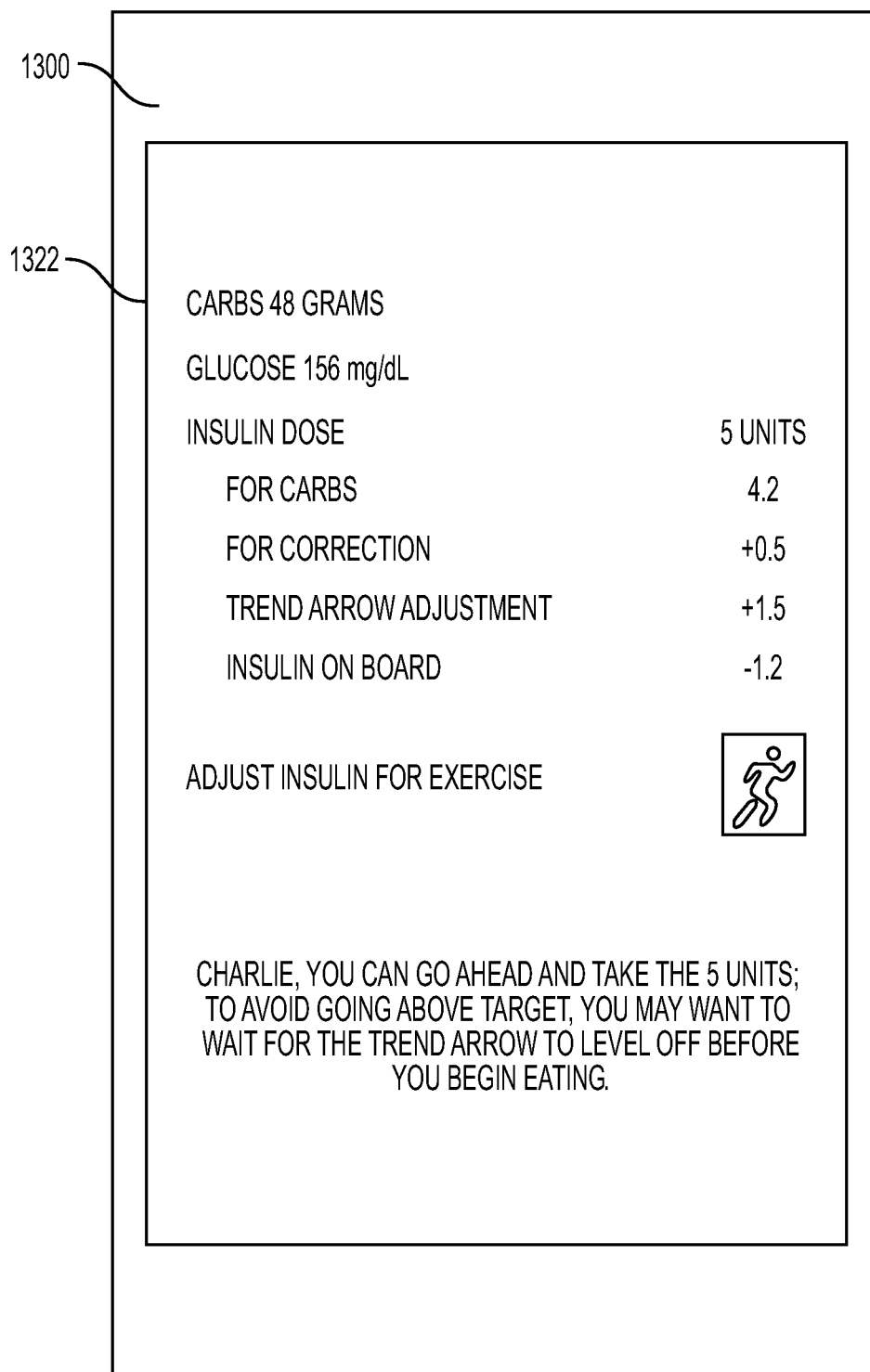
FIG. 13C is another screenshot of an exemplary message, in accordance with an example of the present disclosure.

FIG. 13C shows another example message 1322 provided using CGM message generator 1212 via the mobile phone 1300. Message 1322 is an Advise level 1226 message and includes general advice for a patient. As shown in FIG. 13C, the message 1322 may also include other patient vectors such as carbohydrate information, glucose level, insulin dose, or the like.

Accordingly, as shown via the examples in FIGS. 13A-13C, machine learning driven automated user coaching or CGM feedback may be provided to a user 8. Systems and methods can be used to, for example, provide alerts when critical actions are necessary such as in the case of hypoglycemia or extreme hyperglycemia. Informative messages for less critical glucose readings may also be provided. An insulin dosing support may provide correctional insulin based on a glucose trend, as one of the patient vector corrections via an optimized pathway. According to an implementation, an insulin dose may be a patient vector that can be adjusted based on a glucose trend (e.g., CGM event). A current glucose level may also be a factor when determining an insulin adjustment amount. For example, the trend may be a key component as bolus insulin may require a time period (e.g., 30 minutes) to provide an intended result and, accordingly, a trend projection at the end of that time period may be more useful than a current glucose level alone.

According to an implementation of the disclosed subject matter, an insulin computer may be provided. The insulin computer may be a contextual computer that receives one or more factors as inputs to provide behavior outputs including, for example, an amount of insulin to consume at a given time. The insulin computer may be a part of a CGM monitor or may be external to the CGM monitor (e.g., may be part of one or more electronic device 19). An external insulin computer may be connected to the CGM monitor via a wired or wireless connection such as electronic network 32.

The insulin computer may be a software or an application that operates on the CGM monitor or an external device. For example, the insulin computer may be part of the mHealth application 1. The insulin computer may receive one or more complex inputs and may provide behavioral outputs. Behavior outputs may be instructions or numerical values with one or more behavior output categories including, but not limited to, whether insulin is needed, how much insulin is needed, whether glucose is needed, how much glucose is needed, whether food consumption is needed, how much food consumption is needed, whether exercise is needed, how much exercise is needed, or the like. The function of the insulin computer may change based on a user's state. For example, a behavior output may change to safely and effectively keep the user's glucose level in an optimal range. In this example, a CGM trend may be used as an input to determine the optimal glucose levels.

The insulin computer may receive a CGM trend as an input. A CGM trend may include or may be based on a CGM trace, CGM event, or the like as disclosed herein in detail. The CGM may be based on a change in two or more glucose readings over a period of time. The CGM trend may be based on glucose readings provided by a CGM device. The CGM trend may change over time such that additional glucose readings may result in a modified or updated trend. A past CGM trend may also be used as an input.

The insulin computer may receive dietary information as an input. The dietary information may be provided to the insulin computer in any applicable manner such as by a user input, by inputting content (e.g., an image, a video, etc.) of food prior to it being consumed or example food (e.g., an image of a pizza found online to represent food eaten), or the like. The content may be input using an electronic device 19 or may be received from a resource such as an application that track's a user 8's food consumption. The dietary information may include, or the insulin computer may calculate an insulin to carbohydrate ratio, for the user 8 at a point in time (e.g., when the computer is used to determine a behavioral output). The insulin computer may individualize the effects of the dietary consumption for the user 8 such that the behavior outputs based on the dietary information for user 8 may be different for another user with the same dietary information on a given day. The insulin computer may adjust one or more behavior outputs based on the dietary information and/or the insulin to carbohydrate ratio. Past dietary information may also be used as an input.

The insulin computer may receive exercise (e.g., any activity) information as an input. The exercise information may be provided to the insulin computer in any applicable manner such as by a user input (e.g., past or planned exercise), by an exercise or health tracker (e.g., from an electronic device 19), by one or more components of the CGM monitor, one or more sensors, or the like. The exercise information may include caloric information, heart rate information, duration of exercise, intensity of exercise, strain on body, or the like. The insulin computer may individualize the effects of the exercise for the user 8 such that the behavior outputs based on the exercise information for user 8 may be different for another user with the same exercise information on a given day. The insulin computer may adjust one or more behavior outputs, based on the exercise information. Past exercise information may also be used as an input.

The insulin computer may receive information regarding a previous insulin dose as an input. As further discussed herein in reference to FIG. 13D, the insulin computer may determine a behavior output based on the amount of the previous dose, the time of the previous dose in view of one or more factors associated with user 8 (e.g., diet, exercise, individual body characteristics, CGM trend, historical data, etc.), or the like. For example, when determining whether user 8 should consume additional insulin, based on the half-life of insulin consumed, the insulin computer may determine how much insulin from a previous dose is still in user 8's body.

The insulin computer may receive information regarding a current glucose level as an input. Additionally, the insulin computer may receive information regarding a CGM trend (e.g., the rate of change of glucose in user 8's body) as an input. The current glucose level and/or the CGM trend may enable the insulin computer to determine the direction of the glucose level in user 8's body (e.g., increasing, decreasing, stable, etc.) as well as the speed of change. Based on such information, the insulin computer may adjust one or more behavior outputs. Past glucose levels may also be used as an input.

The insulin computer may receive user 8's sensitivity to insulin as an input. The sensitivity to insulin may be based on a pre-determined value or may be based on historical data received at the insulin computer, CGM monitor, or the like. According to an implementation, the sensitivity may be adjusted overtime based on user 8's use of insulin. Accordingly, the insulin computer may update the sensitivity to insulin periodically or each time a user a behavior output is calculated.

The insulin computer may receive user 8's hypoglycemia history as an input. The insulin computer may consider the time period between a hypoglycemia event and calculation of a behavior output when providing a behavior output. The insulin computer may also consider the degree of severity of the hypoglycemia event when providing the behavior output. As examples, if user 8's history indicates a hypoglycemia event within the past two days from the calculation of a behavior output or if the user 8 experiences hypoglycemia greater than 4% for three consecutive days, then an insulin recommendation by the insulin computer may be more conservative than if there was no hypoglycemia event.

Figure 13D:
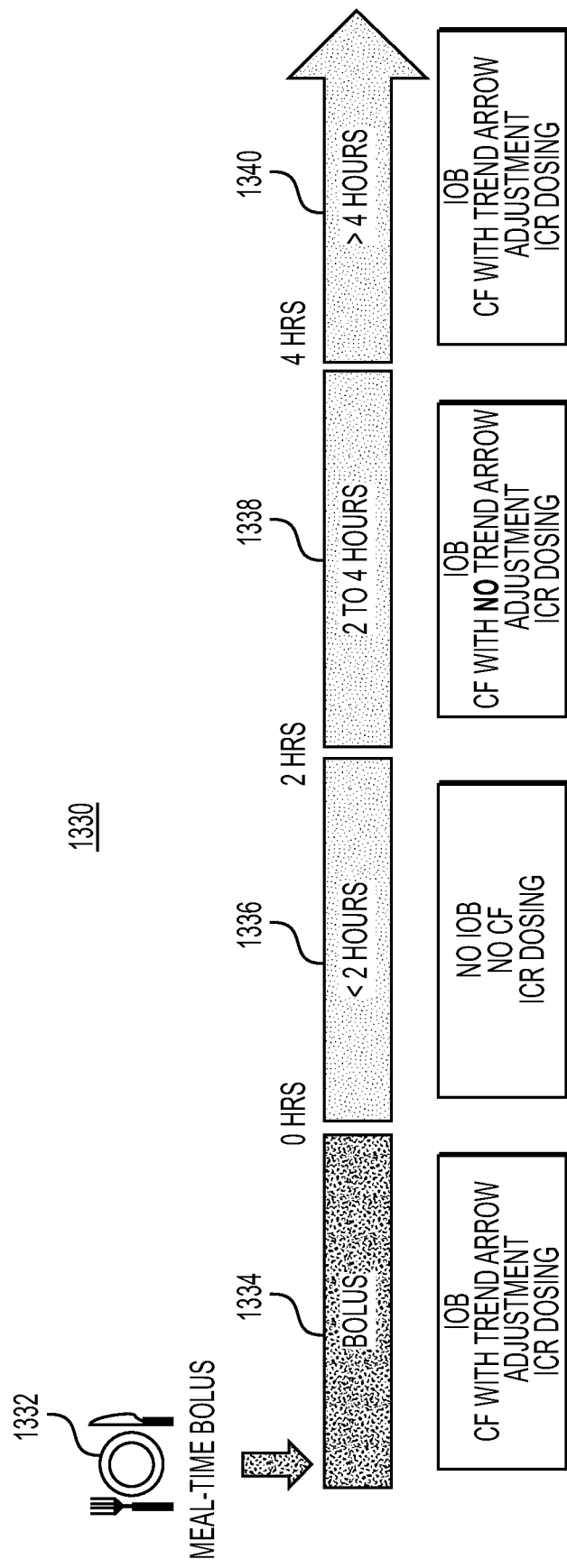
FIG. 13D is a glucose computer, in accordance with an example of the present disclosure.

FIG. 13D provides an example insulin computer 1330 in accordance with an implementation of the disclosed subject matter. As shown, a time zone of the four time zones provided in FIG. 13D may be provided as an input to the insulin computer 1330 such that a behavior output provided by the insulin computer 1330 may be modified based on the time zone at the time of providing the behavior output. Each time zone may be determined based on the previous time that user 8 received insulin (e.g., a bolus injection). The first zone 1334 may be a meal-time bolus from the time of an insulin meal-time bolus administration 1332. The second zone 1336 may be within two hours from the meal-time bolus administration 1332. The third zone 1338 may be from two to four hours from the meal-time bolus administration 1332. The fourth zone 1340 may be over four hours from the meal-time bolus administration 1332. Each zone of the four zones may have associated attributes as provided in FIG. 13D, including insulin on board (10B), correction factor (CF), insulin-to-carbohydrate ratio (ICR), or the like. If within the first zone 1334, then IOB, CF adjusted based on a CGM trend, and ICR dosing may all be considered. If within the second zone 1336, then IOB and CF may not be considered but the ICR dosing may be considered. If within the third time zone 1338 then the IOB CF without a CGM adjustment, and ICR dosing may be considered. If within the fourth zone 1340 then IOB, CF adjusted based on a CGM trend, and ICR dosing may all be considered.

Accordingly, based on the factors discussed herein, the insulin computer may provide a behavior output which may be, but is not limited to whether insulin is needed, how much insulin is needed, whether glucose is needed, how much glucose is needed, whether food consumption is needed, how much food consumption is needed, whether exercise is needed, how much exercise is needed, or the like or a combination thereof. The insulin computer may provide individualized contextual behavior outputs such that a first user with inputs may receive different behavior outputs than a second user with similar inputs, as a result of one or more factors such as the different histories of each respective patient.

According to an implementation, one or more behavior outputs may be determined using a machine learning model that is part of or associated with the insulin computer. The machine learning model may be a supervised model trained to provide behavior outputs based known good outputs and/or based on past behavior outputs provided by the machine learning model and a corresponding change in a past CGM trend after providing the past behavior output. For example, a machine learning model may be configured to provide a behavior output based on one or more inputs, as discussed herein. The machine learning mode may receive an updated CGM trend after providing the behavior outputs. The machine learning model may analyze the CGM trend and update the model (e.g., update weights, a neural network, a layer, etc.) based on the CGM trend to improve future behavior outputs provided by the machine learning model. The machine learning model may update its model for an individual (e.g., based on behavior output provided to the user and the user's CGM trend thereafter) or for multiple users based on feedback (i.e., CGM trends) from one or more users.

Figure 14:
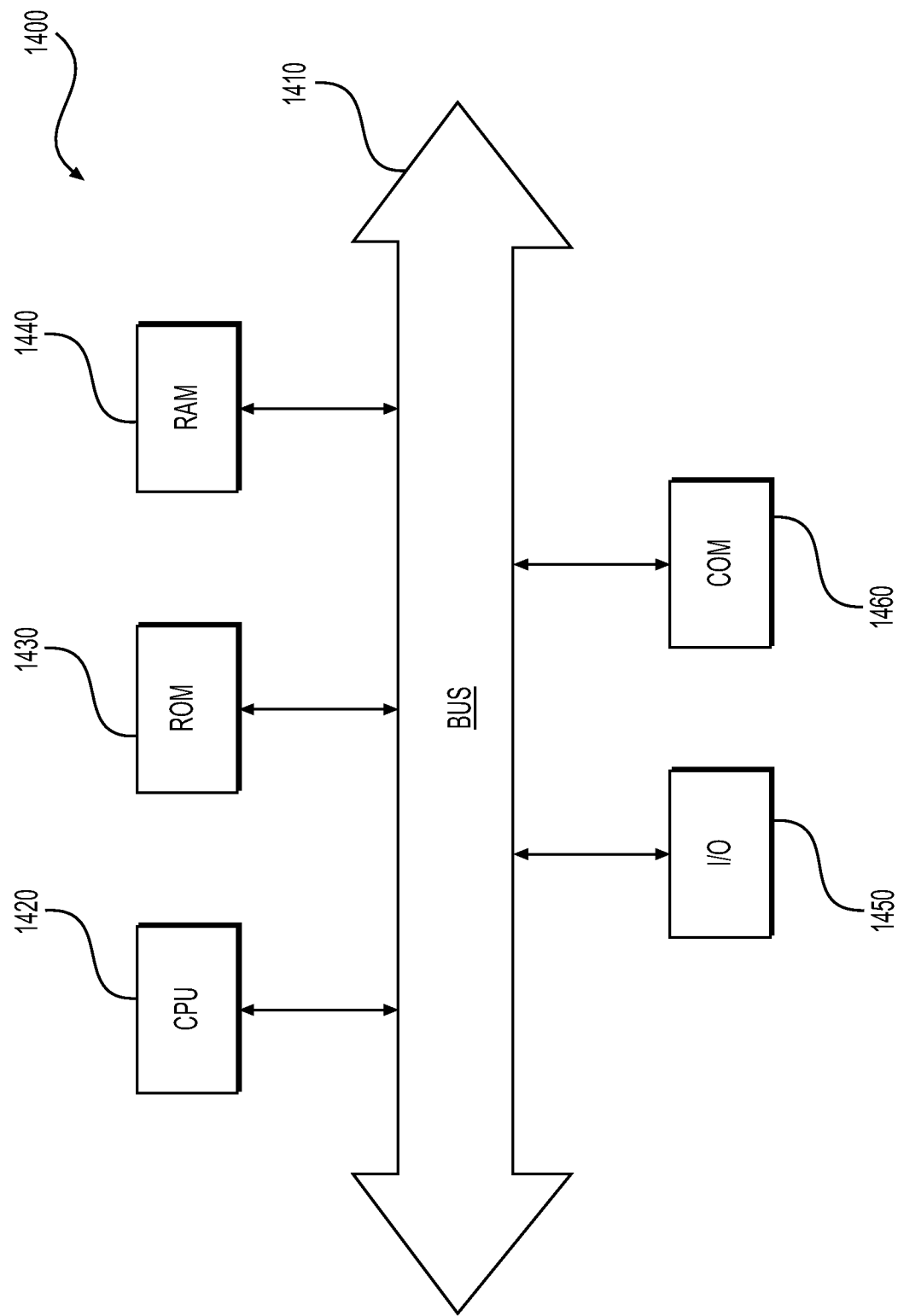
FIG. 14 is a simplified functional block diagram of a computer that may be configured as a host server, for example, to function as healthcare provider decision-making server, according to an example of the present disclosure.

FIG. 14 is a simplified functional block diagram of a computer that may be configured as a host server, for example, to function as healthcare provider decision-making server. FIG. 14 illustrates a network or host computer platform 1400. It is believed that those skilled in the art are familiar with the structure, programming, and general operation of such computer equipment and as a result, the drawings should be self-explanatory.

A platform 1400 for a server or the like, for example, may include a data communication interface 1460 for packet data communication. The platform also may include a central processing unit (CPU) 1420, in the form of one or more processors, for executing program instructions. The platform typically includes an internal communication bus 1410, program storage, and data storage for various data files to be processed and/or communicated by the platform such as ROM 1430 and RAM 1440 or the like. The hardware elements, operating systems, and programming languages of such equipment are conventional in nature, and it is presumed that those skilled in the art are adequately familiar therewith. The platform 1400 also may include input and output ports 1450 to connect with input and output devices such as keyboards, mice, touchscreens, monitors, displays, etc., and communication ports 1460. Of course, the various server functions may be implemented in a distributed fashion on a number of similar platforms to distribute the processing load. Alternatively, the servers may be implemented by appropriate programming of one computer hardware platform.

It would be apparent to one of skill in the relevant art that the present disclosure, as described herein, can be implemented in many different examples of software, hardware, firmware, and/or the entities illustrated in the figures. Any actual software code with the specialized control of hardware to implement examples is not limiting of the detailed description. Thus, examples are described herein with the understanding that modifications and variations of the examples are possible, given the level of detail presented herein. Aspects of the described subject matter may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

It is to be understood that both the foregoing general description and the following detailed description are exemplary and explanatory only and are not restrictive of the disclosed examples, as claimed.

Other examples of the disclosure will be apparent to those skilled in the art from consideration of the specification and practice of the invention disclosed herein. It is intended that the specification and examples be considered as exemplary only, with a true scope and spirit of the invention being indicated by the following claims.

As is evident from the figures, text, and examples presented above, a variety of embodiments may be contemplated including, but not limited to:

1. A computer-implemented method for managing glucose states of a user, the method comprising:

receiving the user's glucose levels using a continuous glucose monitoring (CGM) device;

determining a time in range (TIR) value of the user's glucose level, wherein the TIR value is based on an amount of time the user's glucose level is within a threshold band over a base time period;

determining a TIR state based on the TIR value;

receiving a glucose variability (GV) value based at least on the user's glucose level, wherein the GV value is one of a standard deviation or a coefficient of variance (CV), wherein a CV indicates a variability of the user's glucose level in view of a standard deviation of the glucose level over the base time period;

determining a GV state based on the GV value;

determining a starting state based on the TIR state and the GV state;

determining that the starting state corresponds to a non-ideal state;

generating an optimized pathway to reach an ideal state based on one or more user vectors and the starting state, the optimized pathway comprising one or more adjustments to the one or more user vectors; and providing the optimized pathway to the user.

2. The method of embodiment 1, wherein the threshold band is between approximately 70 mg/dL and 180 mg/dL.

3. The method of embodiment 1, wherein the base time period is 24 hours.

4. The method of embodiment 1, wherein the CV value is determined by dividing the standard deviation of the glucose level by a mean of the glucose level over the base time period.

5. The method of embodiment 1, wherein the TIR state is a binary state selected form one of a good TIR state or a bad TIR state.

6. The method of embodiment 5, wherein the good TIR state corresponds to a TIR value of greater than a TIR cutoff.

7. The method of embodiment 1, wherein the GV state is a binary state selected form one of a good GV state or a bad GV state.

8. The method of embodiment 7, wherein the good GV state corresponds to a GV value of greater than a GV cutoff.

9. The method of embodiment 1, wherein the user vectors comprise one or more of medications, food consumption, exercise value, psycho-social parameters, or social-determinant parameters.

10. The method of embodiment 1, further comprising:
classifying one or more CGM events based on the user's glucose levels, wherein the classifying is based at least on a severity score associated with each of the one or more CGM events; and
generating the optimized pathway further based on the classifying one or more CGM events.

11. The method of embodiment 1, wherein the optimized pathway is further based on a user attribute, the user attribute selected from one or more of a social attribute, medical attribute, user preference, metabolic attribute, or user demographic.

12. The method of embodiment 1, wherein the optimized pathway comprises an increase in one or more state improving habits and/or a decrease in one or more state worsening habits.

13. A computer-implemented method for managing glucose states of a user, the method comprising:
receiving a plurality of optimization profiles for reaching an ideal state from a non-ideal state, the ideal state corresponding to a good time in range (TIR) state and good a glucose variability (GV) state and the non-ideal state comprising at least one of a bad TIR state or a bad GV state;
determining a current TIR state based on a TIR value of the user's glucose level, wherein the TIR value is based on an amount of time the user's glucose level is within a threshold band over a base time period and the current TIR state is one of a good TIR state or a bad TIR state;
determining a current GV state being based on a GV value associated with the user's glucose level, wherein the GV value indicates a standard deviation (SD) of glucose levels or a coefficient of variance (CV), wherein the CV is variability of the user's glucose level in view of a standard deviation of the glucose level over the base time period;
receiving one or more user vectors for the user;
identifying one of the optimization profiles based on the one or more user vectors and one or more user attributes;
identifying an optimized pathway based on the identified optimization profile, the TIR state, and the GV state, the optimized pathway comprising one or more adjustments to the one or more user vectors; and
providing the optimized pathway to the user.

14. The method of embodiment 13, wherein each of the plurality of optimization profiles comprise a different combination of a plurality of user vectors and a plurality of user attributes.

15. The method of embodiment 14, wherein the plurality of optimization profiles are each associated with a plurality of optimized pathways, each of the plurality of optimized pathways being identified based on one or more of a potential TIR state or a potential GV state.

16. The method of embodiment 13, wherein a machine learning model receives, as input, the optimization profile, the TIR state, and the GV state to output the optimized pathway.

17. The method of embodiment 13, further comprising receiving one or more user attribute and identifying one of the optimization profiles further based on the one or more user attributes.

18. The method of embodiment 13, wherein the CV value is determined by dividing the standard deviation of the glucose level by a mean of the glucose level over the base time period.

19. A system for managing glucose levels of a user, the system comprising:
a memory having processor-readable instructions stored therein; and
a processor configured to access the memory and execute the processor-readable instructions, which, when executed by the processor configures the processor to perform a method, the method comprising:
electronically receiving the user's glucose levels using a continuous glucose monitoring (CGM) device configured to obtain glucose values using a component that penetrates a skin of the user;
determining a time in range (TIR) value of the user's glucose level, wherein the TIR value is based on an amount of time the user's glucose level is within a threshold band over a base time period wherein the threshold band is between approximately 70 mg/dL and 180 mg/dL and the base time period is 24 hours;
determining a TIR state based on the TIR value, wherein the TIR state is selected form a good TIR state or a bad TIR state;
receiving a glucose variability (GV) value based at least on the user's glucose level, wherein the GV value is one of a standard deviation or a coefficient of variance (CV), wherein a CV indicates a variability of the user's glucose level in view of a standard deviation of the glucose level over the base time period;
determining a GV state based on the GV value, wherein the GV state is one of a good GV state or a bad GV state;
determining a starting state based on the TIR state and the GV state;
determining that the starting state corresponds to a non-ideal state;
detecting a CGM event based on the user's glucose levels;
characterizing the CGM event based on one or more of a multi-parameter CGM classification or a severity and CGM event trace shape characterization, wherein the multi-parameter CGM classification comprises a glucose level at a beginning of the CGM event, a severity, and a glucose at an end of the CGM event;
generating an optimized pathway to reach an ideal state based on one or more account vectors and the characterizing the CGM event, the optimized pathway comprising one or more adjustments to the one or more account vectors; and
providing the optimized pathway to the user.

20. The system of embodiment 19, wherein providing the optimized pathway to the user comprises providing context based instructions to the user based on the optimized pathway.

Additional embodiments include:
1. A system for providing glucose trend based behavior outputs, the system comprising:

a continuous glucose monitoring (CGM) device configured to output a plurality of glucose readings based on analyzing a bodily fluid over a period of time;

a memory configured to store the plurality of glucose readings; and a processor configured to:

determine a CGM trend based on a change in the plurality of glucose readings output by the CGM device and/or stored in the memory;

determine at least one behavior output based on the CGM trend and at least one additional factor; and provide the at least one behavior output to a user.

2. The system of embodiment 1, wherein the CGM device is further configured to output a subsequent glucose reading, based on the bodily fluid, after the period of time and wherein the processor is further configured to determine an updated CGM trend based on the subsequent glucose reading.

3. The system of embodiment 1, wherein the at least one behavior output corresponds to at least one behavior category selected from whether insulin is needed, how much insulin is needed, whether glucose is needed, how much glucose is needed, whether food consumption is needed, how much food consumption is needed, whether exercise is needed, or how much exercise is needed.

4. The system of embodiment 3, wherein the at least one behavior output categories is selected based on a type of the one additional factor.

5. The system of embodiment 1, wherein the at least one additional factor comprises dietary information.

6. The system of embodiment 5, wherein the dietary information comprises an insulin to carbohydrate ratio.

7. The system of embodiment 1, wherein the at least one additional factor comprises exercise information.

8. The system of embodiment 7, wherein the exercise information may comprise at least one of caloric information, heart rate information, duration of exercise, intensity of exercise, or strain on body.

9. The system of embodiment 1, wherein the at least one additional factor comprises information regarding a previous insulin dose.

10. The system of embodiment 1, wherein the at least one additional factor comprises a glucose level.

11. The system of embodiment 1, wherein the at least one additional factor comprises information regarding a hypoglycemia history.

12. The system of embodiment 11, wherein a hypoglycemia episode within a threshold amount of time causes a behavior output in an insulin recommendation behavior category to be more conservative in comparison to the behavior output in the insulin recommendation behavior category without the hypoglycemia episode within the threshold amount of time.

13. The system of embodiment 1, wherein the processor comprises a machine learning model configured to output the at least one behavior output based on one or more past behavior outputs and a corresponding change in a past CGM trend.

14. The system of embodiment 1, wherein the at least one behavior output is provided to the user using at least one of the CGM monitor, an electronic device, or an application.

15. A computer-implemented method for providing glucose trend based behavior outputs, the method comprising:

receiving, from a continuous glucose monitor (CGM) device, a plurality of glucose readings based on the CGM device analyzing a bodily fluid over a period of time;

determining a CGM trend based on a change in the plurality of glucose readings output by the CGM device;

determining at least one behavior output based on the CGM trend; and providing the at least one behavior output to a user.

16. The method of embodiment 15, wherein the at least one behavior output corresponds to at least one behavior category selected from whether insulin is needed, how much insulin is needed, whether glucose is needed, how much glucose is needed, whether food consumption is needed, how much food consumption is needed, whether exercise is needed, or how much exercise is needed.

17. The method of embodiment 15, wherein the CGM device is further configured to output a subsequent glucose reading, based on the bodily fluid, after the period of time and further comprising determining an updated CGM trend based on the subsequent glucose reading.

18. The method of embodiment 17, further comprising:

receiving the updated CGM trend at the processor;

determining at least one updated behavior output based on the updated CGM trend; and providing the at least one updated behavior output to a user.

19. A system for providing glucose trend based behavior outputs, the system comprising:

a continuous glucose monitoring (CGM) device configured to output a plurality of glucose readings based on analyzing a bodily fluid over a period of time, wherein the CGM device access the bodily fluid via a user's skin and wherein the CGM device is configured to obtain a glucose reading in increments of five minutes or less;

a memory configured to store the plurality of glucose readings; and a processor configured to:

determine a CGM trend based on a change in the plurality of glucose readings output by the CGM device and/or stored in the memory, wherein the CGM trend is determined using a CGM trace mapping the glucose readings over a period of time, and wherein the CGM trend is further based on at least one of a CGM event or a severity score;

receiving at least one additional factor, wherein the at least one additional factor comprises one or more of dietary information, exercise information, an insulin to carbohydrate ratio, information regarding a previous insulin dose, a glucose level, and information regarding a hypoglycemia history;

identifying at least one behavior category selected from whether insulin is needed, how much insulin is needed, whether glucose is needed, how much glucose is needed, whether food consumption is needed, how much food consumption is needed, whether exercise is needed, or how much exercise is needed, based on the CGM trend and the at least one additional factor;

determine at least one behavior output based on the CGM trend and the at least one additional factor, wherein the at least one behavior output is from the at least one identified behavior category and wherein the at least one behavior output is determined using a machine learning model configured to output the at least one behavior output based on one or more past behavior outputs and a corresponding change in a past CGM trend;

generating a graphical user interface (GUI) based on the at least one identified behavior category;

providing the at least one behavior output to a user via the generated GUI;

receiving an updated CGM trend after providing the at least one behavior output to the user, wherein the update CGM trend is based on glucose readings after providing the at least one behavior output to the user; and updating the machine learning model based on the updated CGM trend.

20. The system of embodiment 19, further comprising:

providing the updated CGM trend as an input to the insulin computer;

determining, by the insulin computer, at least one updated behavior output based on the updated CGM trend; and providing the at least one updated behavior output to a user.

Additional embodiments include:

1. A system for managing glucose states of a user, the system comprising:

a continuous glucose monitoring (CGM) device configured to output a plurality of glucose readings based on analyzing a bodily fluid over a period of time;

a memory configured to store the plurality of glucose readings; and a processor configured to:

generate a CGM trace based on the plurality of glucose readings over the period of time;

identify a severity score of the CGM trace, wherein the severity score is based on a height of the CGM trace and a duration of time that the CGM trace stays above a target value;

identify a starting state based on the severity score, the starting state being indicative of a glucose health of the user;

generate an optimized pathway to reach an ideal state based on one or more user vectors and the starting state, the optimized pathway comprising one or more adjustments to the one or more user vectors; and provide the optimized pathway to the user.

2. The system of embodiment 1, further comprising:

identifying a beginning parameter, wherein the beginning parameter is a scaled value determined based on a beginning point of the CGM trace in comparison to a target range; and generating the optimized pathway based further on the beginning parameter.

3. The system of embodiment 2, wherein the beginning parameter is selected form one of a very high parameter, a high parameter, an in range parameter, a low parameter, and a very low parameter.

4. The system of embodiment 1, further comprising:

identifying an ending parameter, wherein the ending parameter is a scaled value determined based on an ending point of the CGM trace in comparison to a target range; and generating the optimized pathway based further on the ending parameter.

5. The system of embodiment 1, wherein the severity score is determined by multiplying a height of the CGM trace by a duration that the CGM trace is above the target value.

6. The system of embodiment 5, wherein the height of the CGM trace is given a first weight and the duration that the CGM trace is above the target value is given a second weight different than the first weight.

7. The system of embodiment 1, wherein a lower severity score corresponds to a starting state closer to the ideal state when compared to a higher severity score.

8. The system of embodiment 1, wherein the user vectors comprise one or more of medications, food consumption, exercise value, psycho-social parameters, or social-determinant parameters.

9. The system of embodiment 1, wherein the optimized pathway is selected from an optimization profile and wherein the optimization profile is identified based on the severity score and one or more user characteristics.

10. The system of embodiment 1, further comprising:

determining a time in range (TIR) value of the CGM trace, wherein the TIR value is based on an amount of time the CGM trace is within a threshold band over a base time period;

determining a TIR state based on the TIR value;

receiving a glucose variability (GV) value based at least on the CGM trace, wherein the GV value is one of a standard deviation or a coefficient of variance (CV), wherein a CV indicates a variability of the glucose readings in view of a standard deviation of the glucose readings over the base time period;

determining a GV state based on the GV value; and determining the starting state further based on the TIR state and the GV state.

11. A computer-implemented method for managing glucose states of a user, the method comprising:

receiving glucose readings of the user, over a period of time, from a continuous glucose monitoring (CGM) device;

generating a CGM trace based on the received glucose readings;

identifying a severity score of the CGM trace, wherein the severity score is based on a height of the CGM trace and a duration of time that the CGM trace stays above a target value;

identifying a CGM trace shape of the CGM trace, wherein the CGM trace shape is based on at least one of a height or a width of a CGM trace;

identifying a starting state based on the severity score and the CGM trace shape, the starting state being indicative of a glucose health of the user;

generating an optimized pathway to reach an ideal state based on one or more user vectors and the starting state, the optimized pathway comprising one or more adjustments to the one or more user vectors; and providing the optimized pathway to the user.

12. The method of embodiment 11, wherein the CGM trace shape is one of a wide shape, a narrow shape, a short shape, and a tall shape.

13. The method of embodiment 12, wherein the CGM trace shape is identified by a machine learning model configured to output CGM trace shapes based on the CGM trace.

14. The method of embodiment 13, wherein the machine learning model may be configured to output CGM trace shapes based on past CGM trace shapes.

15. A system for managing glucose states of a user, the system comprising:

a continuous glucose monitoring (CGM) device configured to output a plurality of glucose readings based on analyzing a bodily fluid over a period of time, wherein the CGM device access the bodily fluid via a user's skin and wherein the CGM device is configured to obtain a glucose reading in increments of five minutes or less;

a memory configured to store the plurality of glucose readings; and a processor configured to:

generate a CGM trace mapping the glucose readings over a period of time;

identify a severity score of the CGM trace, wherein the severity score is based on a height of the CGM trace and a duration of time that the CGM trace stays above a target value;

identifying a CGM trace shape of the CGM trace using a machine learning model, wherein the CGM trace shape is based on at least one of a height or a width of a CGM trace;

identify a starting state based on the severity score and the CGM trace shape, the starting state being indicative of a glucose health of the user;

generate an optimized pathway to reach an ideal state based on one or more user vectors and the starting state, the optimized pathway comprising one or more adjustments to the one or more user vectors;

generating a graphical user interface (GUI) based on the optimized pathway;

providing the at least one optimized pathway to a user via the generated GUI;

receiving an updated CGM trace after providing the optimized pathway to the user, wherein the update CGM trace is based on glucose readings after providing the optimized pathway to the user; and updating the machine learning model based on the updated CGM trace.

16. The system of embodiment 15, further comprising:
identifying a beginning parameter, wherein the beginning parameter is a scaled value determined based on a beginning point of the CGM trace in comparison to a target range; and
generating the optimized pathway based further on the beginning parameter.

17. The system of embodiment 16, wherein the beginning parameter is selected form one of a very high parameter, a high parameter, an in range parameter, a low parameter, and a very low parameter.

18. The system of embodiment 15, further comprising:
identifying an ending parameter, wherein the ending parameter is a scaled value determined based on an ending point of the CGM trace in comparison to a target range; and
generating the optimized pathway based further on the ending parameter.

19. The system of embodiment 15, wherein the CGM trace shape is one of a wide shape, a narrow shape, a short shape, and a tall shape.

20. The system of embodiment 15, wherein the user vectors comprise one or more of medications, food consumption, exercise value, psycho-social parameters, or social-determinant parameters.

What is claimed is:

1. A computer-implemented method for managing glucose states of a user, the method comprising:
receiving a plurality of optimization profiles for reaching an ideal state from a non-ideal state, the ideal state corresponding to a good time in range (TIR) state and a good glucose variability (GV) state and the non-ideal state comprising at least one of a bad TIR state or a bad GV state, wherein the good TIR state is above a threshold TIR state and a bad TIR state is below the threshold TIR state;
determining a current TIR state based on a TIR value of the user's glucose level over a first period of time, wherein the TIR value is based on an amount of time the user's glucose level is within a threshold band over a base time period and the current TIR state is one of a good current TIR state or a bad current TIR state;
determining a current GV state being based on a GV value associated with the user's glucose level, wherein the GV value indicates a standard deviation (SD) of glucose levels or a coefficient of variance (CV), wherein the CV is variability of the user's glucose level in view of a standard deviation of the glucose level over the base time period;
receiving one or more user vectors for the user;
identifying one of the optimization profiles based on the one or more user vectors and one or more user attributes;
identifying an optimized pathway based on the identified optimization profile, the TIR state, and the GV state, the optimized pathway comprising one or more adjustments to the one or more user vectors, wherein the one or more adjustments comprise a medication adjustment, a food consumption adjustment, and an exercise value, wherein:
the optimized pathway is provided as a machine learning model output, the machine learning model output comprising a user vector change based on machine learning inputs comprising the TIR state and the GV state;
the machine learning model inputs further comprising user attributes, wherein the user attributes comprise a medical attribute, a user preference, a metabolic attribute, and a user demographic;
the optimized pathway is further based on a habit index score of the user, determined based on a cohort of users with one or more user attributes in common with the user; and
providing the optimized pathway to the user.

2. The method of claim 1, wherein each of the plurality of optimization profiles comprise a different combination of a plurality of user vectors and a plurality of user attributes.

3. The method of claim 2, wherein the plurality of optimization profiles are each associated with a plurality of optimized pathways, each of the plurality of optimized pathways being identified based on one or more of a potential TIR state or a potential GV state.

4. The method of claim 1, further comprising:
receiving updated glucose levels over a second period of time;
identifying an updated optimized pathway to reach the ideal state based on the updated glucose levels, the updated optimized pathway comprising insulin intake information; and
providing the updated optimized pathway to the user.

5. The method of claim 1, wherein the optimized pathway is provided to the user via a graphical user interface.

6. The method of claim 1, wherein the machine learning model is trained using one of a supervised learning, unsupervised learning, or semi-supervised learning.

7. The method of claim 1, further comprising receiving one or more user attribute and identifying one of the optimization profiles further based on the one or more user attributes.

8. The method of claim 1, wherein the CV value is determined by dividing the standard deviation of the glucose level by a mean of the glucose level over the base time period.

9. The method of claim 1, wherein the user's glucose levels are determined by a continuous glucose monitoring (CGM) device configured to obtain bodily fluid via a skin penetrating component.

10. The method of claim 9, wherein the CGM device is configured to determine the user's glucose levels by sensing a concentration of analytes within the obtained bodily fluid.

11. A system for managing glucose states of a user, the system comprising:
at least one memory storing instructions;

a continuous glucose monitoring (CGM) device configured to obtain bodily fluid via a skin penetrating component; and at least one processor executing the instructions to perform operations, the operations comprising:

receiving a plurality of optimization profiles for reaching an ideal state from a non-ideal state, the ideal state corresponding to a good time in range (TIR) state and a good glucose variability (GV) state and the non-ideal state comprising at least one of a bad TIR state or a bad GV state, wherein the good TIR state is above a threshold TIR state and a bad TIR state is below the threshold TIR state;

determining a current TIR state based on a TIR value of the user's glucose level over a first period of time, wherein the TIR value is based on an amount of time the user's glucose level is within a threshold band over a base time period and the current TIR state is one of a good current TIR state or a bad current TIR state;

determining a current GV state being based on a GV value associated with the user's glucose level, wherein the GV value indicates a standard deviation (SD) of glucose levels or a coefficient of variance (CV), wherein the CV is variability of the user's glucose level in view of a standard deviation of the glucose level over the base time period;

receiving one or more user vectors for the user;

identifying one of the optimization profiles based on the one or more user vectors and one or more user attributes;

identifying an optimized pathway based on the identified optimization profile, the TIR state, and the GV state, the optimized pathway comprising one or more adjustments to the one or more user vectors, wherein the one or more adjustments comprise a medication adjustment, a food consumption adjustment, and an exercise value, wherein:

the optimized pathway is provided as a machine learning model output, the machine learning model output comprising a user vector change based on machine learning inputs comprising the TIR state and the GV state;

the machine learning model inputs further comprising user attributes, wherein the user attributes comprise a medical attribute, a user preference, a metabolic attribute, and a user demographic;

the optimized pathway is further based on a habit index score of the user, determined based on a cohort of users with one or more user attributes in common with the user; and providing the optimized pathway to the user.

12. The system of claim 11, wherein each of the plurality of optimization profiles comprise a different combination of a plurality of user vectors and a plurality of user attributes.

13. The system of claim 12, wherein the plurality of optimization profiles are each associated with a plurality of optimized pathways, each of the plurality of optimized pathways being identified based on one or more of a potential TIR state or a potential GV state.

14. The system of claim 11, wherein the processor is further configured to:

receiving updated glucose levels over a second period of time;

identifying an updated optimized pathway to reach the ideal state based on the updated glucose levels, the updated optimized pathway comprising insulin intake information; and providing the updated optimized pathway to the user.

15. The system of claim 11, wherein the optimized pathway is provided to the user via a graphical user interface.

16. The system of claim 11, wherein the machine learning model is trained using one of a supervised learning, unsupervised learning, or semi-supervised learning.

17. The system of claim 11, further comprising receiving one or more user attribute and identifying one of the optimization profiles further based on the one or more user attributes.

18. The system of claim 11, wherein the CV value is determined by dividing the standard deviation of the glucose level by a mean of the glucose level over the base time period.

19. The system of claim 18, wherein the CGM device is configured to determine the user's glucose levels by sensing a concentration of analytes within the obtained bodily fluid.

20. A non-transitory computer-readable medium storing instructions that, when executed by a processor, cause the processor to perform operations, the operations comprising:

receiving a plurality of optimization profiles for reaching an ideal state from a non-ideal state, the ideal state corresponding to a good time in range (TIR) state and good glucose variability (GV) state and the non-ideal state comprising at least one of a bad TIR state or a bad GV state, wherein the good TIR state is above a threshold TIR state and a bad TIR state is below the threshold TIR state;

determining a current TIR state based on a TIR value of the user's glucose level over a first period of time, wherein the TIR value is based on an amount of time the user's glucose level is within a threshold band over a base time period and the current TIR state is one of a good current TIR state or a bad current TIR state;

determining a current GV state being based on a GV value associated with the user's glucose level, wherein the GV value indicates a standard deviation (SD) of glucose levels or a coefficient of variance (CV), wherein the CV is variability of the user's glucose level in view of a standard deviation of the glucose level over the base time period;

receiving one or more user vectors for the user;

identifying one of the optimization profiles based on the one or more user vectors and one or more user attributes;

identifying an optimized pathway based on the identified optimization profile, the TIR state, and the GV state, the optimized pathway comprising one or more adjustments to the one or more user vectors, wherein the one or more adjustments comprise a medication adjustment, a food consumption adjustment, and an exercise value, wherein:

the optimized pathway is provided as a machine learning model output, the machine learning model output comprising a user vector change based on machine learning inputs comprising the TIR state and the GV state;

the machine learning model inputs further comprising user attributes, wherein the user attributes comprise a medical attribute, a user preference, a metabolic attribute, and a user demographic;

the optimized pathway is further based on a habit index score of the user, determined based on a cohort of users with one or more user attributes in common with the user; and providing the optimized pathway to the user.

\* \* \* \* \*